United States Patent
Hipskind et al.

(10) Patent No.: US 10,184,134 B2
(45) Date of Patent: Jan. 22, 2019

(54) SOYBEAN EVENT SYHT0H2 AND COMPOSITIONS AND METHODS FOR DETECTION THEREOF

(75) Inventors: John Daniel Hipskind, Durham, NC (US); Kristina Burgin, Durham, NC (US); Rakesh Jain, Vero Beach, FL (US); Karolyn Terpstra, Highland, IL (US); Marina Sigareva, Sudbury, MA (US); Annick Jeanne De Framond, Durham, NC (US); Becky Breitinger, Durham, NC (US); Vance Cary Kramer, Durham, NC (US); Weining Gu, Durham, NC (US)

(73) Assignee: Syngenta Participations AG, Basel (CH)

( * ) Notice: Subject to any disclaimer, the term of this patent is extended or adjusted under 35 U.S.C. 154(b) by 1265 days.

(21) Appl. No.: 13/994,145

(22) PCT Filed: Dec. 9, 2011

(86) PCT No.: PCT/US2011/064143
§ 371 (c)(1),
(2), (4) Date: Dec. 12, 2013

(87) PCT Pub. No.: WO2012/082548
PCT Pub. Date: Jun. 21, 2012

(65) Prior Publication Data
US 2014/0201860 A1 Jul. 17, 2014

Related U.S. Application Data

(60) Provisional application No. 61/467,621, filed on Mar. 25, 2011, provisional application No. 61/423,131, filed on Dec. 15, 2010.

(51) Int. Cl.
| | |
|---|---|
| *A01H 5/10* | (2018.01) |
| *C12N 15/82* | (2006.01) |
| *A01N 41/10* | (2006.01) |
| *A01N 57/20* | (2006.01) |
| *C12Q 1/6895* | (2018.01) |
| *A01N 37/40* | (2006.01) |
| *A01N 39/04* | (2006.01) |

(52) U.S. Cl.
CPC ......... *C12N 15/8274* (2013.01); *A01H 5/10* (2013.01); *A01N 37/40* (2013.01); *A01N 39/04* (2013.01); *A01N 41/10* (2013.01); *A01N 57/20* (2013.01); *C12N 15/8281* (2013.01); *C12N 15/8282* (2013.01); *C12N 15/8283* (2013.01); *C12N 15/8286* (2013.01); *C12Q 1/6895* (2013.01)

(58) Field of Classification Search
CPC ...................................................... C12N 15/82
See application file for complete search history.

(56) References Cited

U.S. PATENT DOCUMENTS

| | | | |
|---|---|---|---|
| 6,268,549 B1 | 7/2001 | Sailland et al. | |
| 7,312,379 B2 | 12/2007 | Andrews et al. | |
| 8,269,068 B2 | 9/2012 | Hawkes et al. | |
| 2003/0176284 A1 | 9/2003 | Hacker et al. | |
| 2003/0187029 A1* | 10/2003 | Valdez | A01N 53/00 514/341 |
| 2006/0282915 A1* | 12/2006 | Malven | A01H 1/02 800/278 |
| 2010/0099859 A1 | 4/2010 | Malven et al. | |
| 2010/0197503 A1* | 8/2010 | Hawkes | C12N 9/0069 504/348 |

FOREIGN PATENT DOCUMENTS

| | | | | |
|---|---|---|---|---|
| WO | 2008150473 A2 | 12/2008 | | |
| WO | WO 2011/063413 | * | 5/2011 | ............... A01H 5/00 |
| WO | WO2011063413 | * | 5/2011 | ............... A01H 5/00 |

OTHER PUBLICATIONS

Olhoft, P. M., et al. 2004. Plant biotechnology journal 2(4): 289-300.*
Siminszky, B., et al. 1999. Proceedings of the National Academy of Sciences 96(4): 1750-1755.*
Argôlo-Filho, R.C., et al, Insects 2014, 5:62-91.*
Padgette, Stephen R., et al. "Development, identification, and characterization of a glyphosate-tolerant soybean line." Crop science 35.5 (1995): 1451-1461. (Year: 1995).*
Dufourmantel et al. Generation and characterization of soybean and marker-free tobacco plastid transformants over-expressing a bacterial 4-hydroxyphenylpyruvate dioxygenase which provides strong herbicide tolerance. Plant Biotech J. 5:118-133 (2007).
Liu et al. Single-site mutations in the carboxyltransferase domain of plastic acetyl-CoA carboxylase confer resistance to grass-specific herbicides. Proceedings of the National Academy of Sciences. 104(9):3627-3632 (Feb. 27, 2007).

* cited by examiner

Primary Examiner — Weihua Fan
(74) Attorney, Agent, or Firm — S. Matthew Edwards

(57) ABSTRACT

Soybean plants comprising event SYHT0H2, methods of detecting and using the same, and soybean plants comprising a heterologous insert at the same site as SYHT0H2.

19 Claims, 1 Drawing Sheet

Specification includes a Sequence Listing.

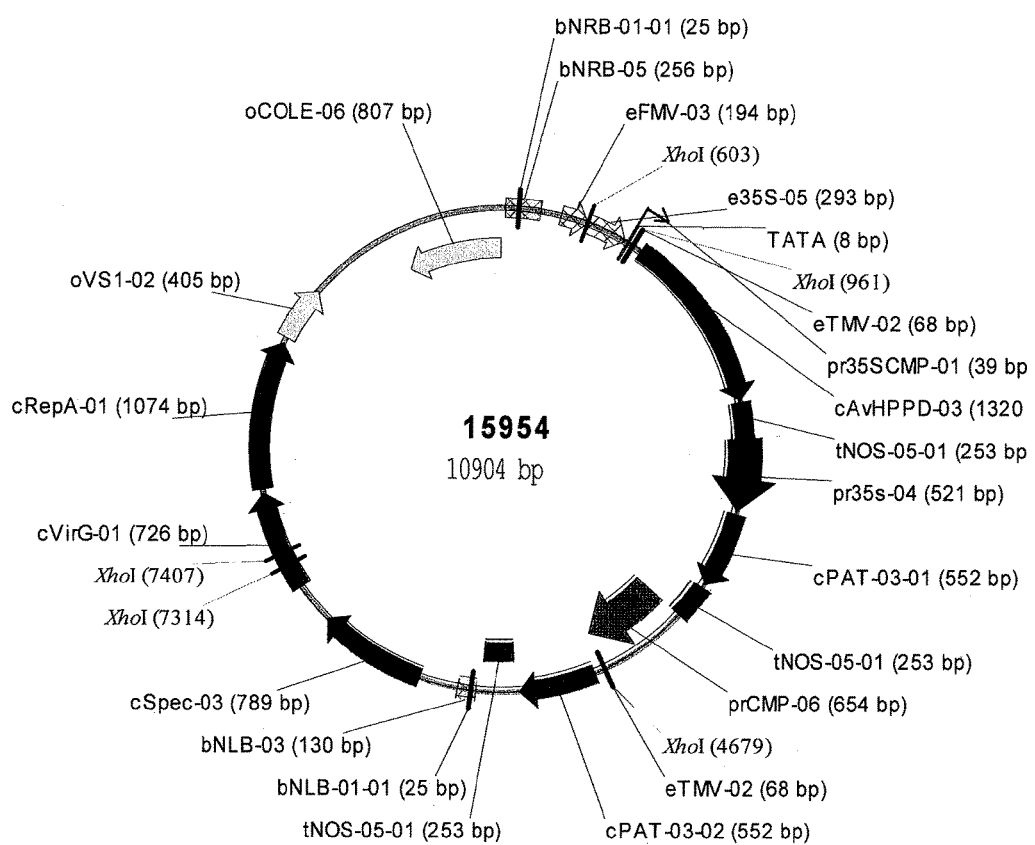

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Derived from Glycine max and Avena sativa

<400> SEQUENCE: 1
accatcacag aattgacgct                                               20

<210> SEQ ID NO 2

```
<211> LENGTH: 20
<212> TYPE: DNA
<213> ORGANISM: Artificial Sequence
<220> FEATURE:
<223> OTHER INFORMATION: Derived from Glycine max and Avena sativa

<400> SEQUENCE: 2
taaaccctaa accaatggca                                                   20

<210> SEQ ID NO 3
<211> LENGTH: 40
<212> TYPE: DNA
<213> ORGANISM: Artificial Sequence
<220> FEATURE:
<223> OTHER INFORMATION: Derived from Glycine max and Avena sativa

<400> SEQUENCE: 3
agatgagaga accatcacag aattgacgct tagacaactt                             40

<210> SEQ ID NO 4
<211> LENGTH: 40
<212> TYPE: DNA
<213> ORGANISM: Artificial Sequence
<220> FEATURE:
<223> OTHER INFORMATION: Derived from Glycine max and Avena sativa

<400> SEQUENCE: 4
ttaagttgtc taaaccctaa accaatggca cacaaaaatt                             40

<210> SEQ ID NO 5
<211> LENGTH: 60
<212> TYPE: DNA
<213> ORGANISM: Artificial Sequence
<220> FEATURE:
<223> OTHER INFORMATION: Derived from Glycine max and Avena sativa

<400> SEQUENCE: 5
taggatgaag agatgagaga accatcacag aattgacgct tagacaactt aataacacat       60

<210> SEQ ID NO 6
<211> LENGTH: 60
<212> TYPE: DNA
<213> ORGANISM: Artificial Sequence
<220> FEATURE:
<223> OTHER INFORMATION: Derived from Glycine max and Avena sativa

<400> SEQUENCE: 6
caatgtgtta ttaagttgtc taaaccctaa accaatggca cacaaaaatt cccatcctag       60

<210> SEQ ID NO 7
<211> LENGTH: 99
<212> TYPE: DNA
<213> ORGANISM: Glycine max

<400> SEQUENCE: 7
acatatacta cataagaagg aggtggagaa agtgtatgta accgacaaca aaaaactaat       60
aggaatatat aggatgaaga gatgagagaa ccatcacag                              99

<210> SEQ ID NO 8
<211> LENGTH: 462
<212> TYPE: DNA
<213> ORGANISM: Glycine max

<400> SEQUENCE: 8
accaatggca cacaaaaatt cccatcctag tttttggagt aattaatgaa ctagcaatta       60
```

| | |
|---|---|
| tataataagc tctgtatctg ttatattctg cattaatttt gttgaataaa aaacactgta | 120 |
| aattaattgg tcatgtgtta tattttgcac actaattttt tttttaaaaa aggtgggaga | 180 |
| gcgtgatatt tttagttgtc cagaaaataa agattgaaaa atttgaatgt atttggcacg | 240 |
| tgggatactt taaaaattag aaggcacctt attgttact tcgatcggag aaaaataata | 300 |
| aaatccttta tatgttaatt tatttcaatt tgtatgtctg tagtaggaat attaaagtag | 360 |
| acatttatca ttaatctcat tattagtctt tccttttgta gaatctcgtt aattttatta | 420 |
| actaacttt aaataactct ctagaggaat gaacaaaata at | 462 |

<210> SEQ ID NO 9
<211> LENGTH: 7914
<212> TYPE: DNA
<213> ORGANISM: Artificial Sequence
<220> FEATURE:
<223> OTHER INFORMATION: Avena sativa sequence optimized for expression
      in Glycine max

<400> SEQUENCE: 9

| | |
|---|---|
| aattgacgct tagacaactt aataacacat tgcggatacg gccatgctgg ccgcccgggc | 60 |
| atggtaccca attcccgatc tagtaacata gatgacaccg cgcgcgataa tttatcctag | 120 |
| tttgcgcgct atattttgtt ttctatcgcg tattaaatgt ataattgcgg gactctaatc | 180 |
| ataaaaaccc atctcataaa taacgtcatg cattacatgt taattattac atgcttaacg | 240 |
| taattcaaca gaaattatat gataatcatc gcaagaccgg caacaggatt caatcttaag | 300 |
| aaactttatt gccaaatgtt tgaacgatcg gggaaattcg gggatctaga gctcgactca | 360 |
| tatctgggta actggcctaa ctggccttgg aggagctggc aactcaaaat ccctttgcca | 420 |
| aaaaccaaca tcatgccatc caccatgctt gtatccagct gcgcgcaatg taccccgggc | 480 |
| tgtgtatccc aaagcctcat gcaacctaac agatggatcg tttggaaggc ctataacagc | 540 |
| aaccacagac ttaaaacctt gcgcctccat agacttaagc aaatgtgtgt acaatgtaga | 600 |
| tcctaggccc aacctttgat gcctatgtga cacgtaaaca gtactctcaa ctgtccaatc | 660 |
| gtaagcgttc ctagccttcc agggcccagc gtaagcaata ccagccacaa caccctcaac | 720 |
| ctcagcaacc aaccaagggt atctatcttg caacctctct agatcatcaa tccactcttg | 780 |
| tggtgtttgt ggctctgtcc taaagttcac tgtagacgtc tcaatgtaat ggttaacgat | 840 |
| atcacaaacc gcggccatat cagctgctgt agctggccta atctcaactg gtctcctctc | 900 |
| cggagacatg gtgggatcct gtaattgtaa atagtaattg taatgttgtt tgttgtttgt | 960 |
| tgttgttggt aattgttgta aaaatactcg agggtttatg tttttacaaa cgactccaac | 1020 |
| aaagtatcaa gttttattca acagaatga tacagattta aatatcgggt tttatacaaa | 1080 |
| ccatatgata tttatcaatt cagtgatcct atacggacgg tggagacaaa aatcatcaag | 1140 |
| aatcatcttt gagatgagaa agcttagctc ttacctgttt tcgtcgtctt ggcttttctt | 1200 |
| cttcctggcc acctgcctga atacttcgcc gccttgacta cttctaggct acttgctctc | 1260 |
| tttctctctc taggactatc tctctgagat tttgctccct taacaatgag ggaggggcta | 1320 |
| agtatttata gactgacggg tgagtggaca tttcccaaac tacccttact tatttcgtaa | 1380 |
| gcccttacgt cattgctcca ttattggagt ctgaagatgc cttcacatgg tggaccccca | 1440 |
| cctgtcggcc acgaatctta tttgttcgtc agaaaaagcc aaaccgactg cacagttttt | 1500 |
| ccatcgtggt agggaccact ttggtattga ttaaaggcag ccgacctaac ctttgtcaga | 1560 |
| cgcattattt cacgcgtttt cttttacaga ttccatcttc atttgtggga cagtatgtct | 1620 |

```
gccactttgt ctgccagtaa ttaaacgcgg tccggatcta gtaacataga tgacaccgcg    1680
cgcgataatt tatcctagtt tgcgcgctat attttgtttt ctatcgcgta ttaaatgtat    1740
aattgcggga ctctaatcat aaaaacccat ctcataaata acgtcatgca ttacatgtta    1800
attattacat gcttaacgta attcaacaga aattatatga taatcatcgc aagaccggca    1860
acaggattca atcttaagaa actttattgc caaatgtttg aacgatctgc aggtcgaccc    1920
atggcgccga tatcactagt tcagatctgg gtaactggcc taactggcct tggaggagct    1980
ggcaactcaa aatcccttg ccaaaaacca acatcatgcc atccaccatg cttgtatcca    2040
gctgcgcgca atgtaccccg ggctgtgtat cccaaagcct catgcaacct aacagatgga    2100
tcgtttggaa ggcctataac agcaaccaca gacttaaaac cttgcgcctc catagactta    2160
agcaaatgtg tgtacaatgt ggatcctagg cccaaccttt gatgcctatg tgacacgtaa    2220
acagtactct caactgtcca atcgtaagcg ttcctagcct tccagggccc agcgtaagca    2280
ataccagcca caacaccctc aacctcagca accaaccaag ggtatctatc ttgcaacctc    2340
tctagatcat caatccactc ttgtggtgtt tgtggctctg tcctaaagtt cactgtagac    2400
gtctcaatgt aatggttaac gatatcacaa accgcggcca tatcagctgc tgtagctggc    2460
ctaatctcaa ctggtctcct ctccggagac atggtggact agtgatttca gcgtgtcctc    2520
tccaaatgaa atgaacttcc ttatatagag gaagggtctt gcgaaggata gtgggattgt    2580
gcgtcatccc ttacgtcagt ggagatatca catcaatcca cttgctttga agacgtggtt    2640
ggaacgtctt cttttttccac gatgctcctc gtgggtgggg gtccatcttt gggaccactg    2700
tcggcagagg catcttcaac gatggccttt cctttatcgc aatgatggca tttgtaggag    2760
ccaccttcct tttccactat cttcacaata aagtgacaga tagctgggca atggaacctt    2820
tgctgctgca catggacttg ctgtcagatc tgttggagct taatatccgg aaacctcctc    2880
ggattccatt gcccagctat ctgtcacttt attgtgaaga gagtggaaaa ggaaggtggc    2940
tcctacaaat gccatcattg cgataaagga aaggctatcg ttgaagatgc ctctgccgac    3000
agtggtccca agatggacc cccacccacg aggagcatcg tggaaaaaga agacgttcca    3060
accacgtctt caaagcaagt ggattgatgt gatatctcca ctgacgtaag ggatgacgaa    3120
caatcccact atccttctgc aggtcgactc tagaggatcc tataaatagg aagttcattt    3180
catttggaga ggaaacctcg agtattttta caacaattac caacaacaac aaacaacaaa    3240
caacattaca attactattt acaattacac atatgcctcc aacaccagct actgctactg    3300
gagctgctgc tgctgccgtt acaccagaac atgctgcaag gtcattccct agagttgttc    3360
gcgttaaccc taggtctgac agattccctg ttctgtcctt ccatcatgtg gagctttggt    3420
gtgctgatgc agctagtgct gctggtcgtt tcagctttgc acttggagca ccacttgctg    3480
caagatctga tctgtctaca gggaactcag cacatgcttc tctcctactt cgatctggag    3540
cattagcctt cctttttacc gctccttatg ctccacctcc acaagaagct gcaactgctg    3600
caactgcttc cattccctcc ttttcagcag atgctgcaag aacctttgct gctgcacatg    3660
gacttgctgt cagatctgtt ggagttaggg ttgctgatgc agctgaagca tttcgcgtta    3720
gtgttgctgg aggagcaaga cctgcttttg ctccagcaga tcttggtcac ggatttggac    3780
ttgctgaagt ggagctgtat ggagatgtgg ttctgagatt cgtgagctat cctgacgaaa    3840
ctgacctacc atttctccca ggattcgaga gggtttcaag tccaggtgca gttgactacg    3900
gtttgactcg cttttgaccac gttgttggaa acgttccaga aatggctcct gtcatcgact    3960
```

```
acatgaaggg attccttggt ttccacgagt tcgctgaatt cacagcagag gatgttggaa    4020
ccacagaatc tggactgaac agtgtggttc tagccaacaa cagtgaagct gttcttctgc    4080
cattgaacga gcctgttcat ggaaccaaga gacgatctca gatccaaacc tacctcgaat    4140
accatggtgg accaggagtt caacacatcg cattggcttc taacgatgtg cttcgaactc    4200
tcagggaaat gagagccaga actccaatgg gagggttcga atttatggct cctccacaag    4260
ccaagtacta tgaaggagtc cgtagaatcg ctggagatgt cttgtcagag gaacagatca    4320
aggagtgtca agaactgggt gttctcgttg atcgagacga tcaaggtgtg ctactccaga    4380
tcttcaccaa accagttggt gatcgtccca ctttttttcct cgaaatgatt cagcgaatag    4440
gatgcatgga gaaggatgaa gttgggcaag agtaccagaa aggtggatgt ggtgggtttg    4500
gaaaggggaa cttttccgag ttgttcaagt ccatagagga ctacgagaag tcactggaag    4560
tcaagcagtc tgtcgttgct cagaagagct aagagctctt catatgacga tcgttcaaac    4620
atttggcaat aaagtttctt aagattgaat cctgttgccg tcttgcgat gattatcata    4680
taatttctgt tgaattacgt taagcatgta ataattaaca tgtaatgcat gacgttattt    4740
atgagatggg tttttatgat tagagtcccg caattataca tttaatacgc gatagaaaac    4800
aaaatatagc gcgcaaacta ggataaaatta tcgcgcgcgg tgtcatctat gttactagat    4860
cgcggaccca gtcaaagatt caaatagagg acctaacaga actcgccgta aagactggcg    4920
aacagttcat acagagtctc ttacgactca atgacaagaa gaaaatcttc gtcaacatgg    4980
tggagcacga cacgcttgtc tactccaaaa atatcaaaga tacagtctca gaagaccaaa    5040
gggcaattga acttttcaa caaagatgac ttttcaacaa agggtaatat ccggaaacct    5100
cctcggattc cattgcccag ctatctgtca ctttattgtg aagatagtgg aaaaggaagg    5160
tggctcctac aaatgccatc attgcgataa aggaaaggcc atcgttgaag atgcctctgc    5220
cgacagtggt cccaaagatg accccccacc cacgaggagc atcgtggaaa aagaagacgt    5280
tccaaccacg tcttcaaagc aagtggattg atgtgatatc tccactgacg taagggatga    5340
cgcacaatcc cactatcctt cgcaagaccc ttcctctata taaggaagtt catttcattt    5400
ggagaggaca cgctgaaatc actagtccac catgtctccg gagaggagac cagttgagat    5460
taggccagct acagcagctg atatggccgc ggtttgtgat atcgttaacc attacattga    5520
gacgtctaca gtgaacttta ggacagagcc acaaacacca caagagtgga ttgatgatct    5580
agagaggttg caagatagat acccttggtt ggttgctgag gttgagggtg ttgtggctgg    5640
tattgcttac gctgggccct ggaaggctag gaacgcttac gattggacag ttgagagtac    5700
tgtttacgtg tcacataggc atcaaaggtt gggcctagga tccacattgt acacacattt    5760
gcttaagtct atggaggcgc aaggttttaa gtctgtggtt gctgttatag gccttccaaa    5820
cgatccatct gttaggttgc atgaggcttt gggatacaca gcccggggta cattgcgcgc    5880
agctggatac aagcatggtg gatggcatga tgttggtttt tggcaaaggg attttgagtt    5940
gccagctcct ccaaggccag ttaggccagt tacccagatc tgaactagtg atatcggcgc    6000
catgggtcga cctgcagatc gttcaaacat ttggcaataa agtttcttaa gattgaatcc    6060
tgttgccggg cttgcgatga ttatcatata atttctgttg aattacgtta agcatgtaat    6120
aattaacatg taatgcatga cgttatttat gagatgggtt tttatgatta gagtcccgca    6180
attatacatt taatacgcga tagaaaacaa atatagcgc gcaaactagg ataaattatc    6240
gcgcgcggtg tcatctatgt tactagatcc ggaccgcgtt taattactgg cagacaaagt    6300
ggcagacata ctgtcccaca aatgaagatg gaatctgtaa aagaaaacgc gtgaaataat    6360
```

```
gcgtctgaca aaggttaggt cggctgcctt taatcaatac caaagtggtc cctaccacga    6420
tggaaaaact gtgcagtcgg tttggctttt tctgacgaac aaataagatt cgtggccgac    6480
aggtgggggt ccaccatgtg aaggcatctt cagactccaa taatggagca atgacgtaag    6540
ggcttacgaa ataagtaagg gtagtttggg aaatgtccac tcacccgtca gtctataaat    6600
acttagcccc tccctcattg ttaagggagc aaaatctcag agagatagtc ctagagagag    6660
aaagagagca agtagcctag aagtagtcaa ggcggcgaag tattcaggca ggtggccagg    6720
aagaagaaaa gccaagacga cgaaaacagg taagagctaa gctttctcat ctcaaagatg    6780
attcttgatg atttttgtct ccaccgtccg tataggatca ctgaattgat aaatatcata    6840
tggtttgtat aaaacccgat atttaaatct gtatcattct gtttgaataa aacttgatac    6900
tttgttggag tcgtttgtaa aaacataaac cctcgagtat ttttacaaca attaccaaca    6960
acaacaaaca acaaacaaca ttacaattac tatttacaat tacaggatcc caccatgtct    7020
ccggagagga gaccagttga gattaggcca gctacagcag ctgatatggc cgcggtttgt    7080
gatatcgtta accattacat tgagacgtct acagtgaact ttaggacaga gccacaaaca    7140
ccacaagagt ggattgatga tctagagagg ttgcaagata gatacccttg gttggttgct    7200
gaggttgagg gtgttgtggc tggtattgct tacgctgggc cctggaaggc taggaacgct    7260
tacgattgga cagttgagag tactgtttac gtgtcacata ggcatcaaag gttgggccta    7320
ggatctacat tgtacacaca tttgcttaag tctatggagg cgcaaggttt taagtctgtg    7380
gttgctgtta taggccttcc aaacgatcca tctgttaggt tgcatgaggc tttgggatac    7440
acagcccggg gtacattgcg cgcagctgga tacaagcatg gtggatggca tgatgttggt    7500
ttttggcaaa gggattttga gttgccagct cctccaaggc cagttaggcc agttaccag    7560 atatgagtcg agctctagat ccccgaattt ccccgatcgt tcaaacattt ggcaataaag    7620
tttcttaaga ttgaatcctg ttgccggtct tgcgatgatt atcatataat ttctgttgaa    7680
ttacgttaag catgtaataa ttaacatgta atgcatgacg ttatttatga gatgggtttt    7740
tatgattaga gtcccgcaat tatacattta atacgcgata gaaaacaaaa tatagcgcgc    7800
aaactaggat aaattatcgc gcgcggtgtc atctatgtta ctagatcggg aattgggtac    7860
catgcccggg cggccagcat ggccgtatcc gcaatgtgtt attaagttgt ctaa          7914
```

<210> SEQ ID NO 10
<211> LENGTH: 9206
<212> TYPE: DNA
<213> ORGANISM: Artificial Sequence
<220> FEATURE:
<223> OTHER INFORMATION: Derived from Glycine max and Avena sativa
<220> FEATURE:
<221> NAME/KEY: misc_feature
<222> LOCATION: (1)..(821)
<223> OTHER INFORMATION: genomic region called LB2
<220> FEATURE:
<221> NAME/KEY: misc_feature
<222> LOCATION: (822)..(8735)
<223> OTHER INFORMATION: heterologous inserted DNA
<220> FEATURE:
<221> NAME/KEY: misc_feature
<222> LOCATION: (8736)..(9206)
<223> OTHER INFORMATION: genomic flanking sequence called LB1

<400> SEQUENCE: 10

```
tgatcttaaa aattcaaagt ccacctaatt tgacaaggaa agcaccaggt agcgtttcat      60
ctaatgtttt ctccatatag ttgactattt acccaagttc atgacgatgt caacaatgca     120
```

```
agttgtacga ctaaacttct tccttgtgca ataaaatgcc atctattact gtcacaaagg      180 aagtgttttta ctgtcttata agttagtttg attacataag ttttatttag taaacgagct    240
tattaattta ttgcatatta ttaggtggtc caaaatagaa tagaggatcc agagttatct     300
aataatttct tatatgaatg ggtctagatt taacaaaaat gaatcaaaat catttatgta     360
tgattattct actttatata tatgaggaaa cttaaaaggt tattttttta ttattatgat    420
attgatatag aatatttatc aatttttttg aaaattattt tttgatataa aatctgattg    480 accatttta ataattttt tccttacaat gacgttttt tatatacaag atgaatttaa       540
aattttaatt atggggatcg aatttaaata tcgattaatg acttaatgat actctaagct    600
aatttagttt tacataattg agaatgaggc accaacattc ttgtggtaat attaaatttt    660
ctgttgactt ttttttacgt aaatgatact tgattagaag atgactaata aatgaaggct    720
ttacatatac tacataagaa ggaggtggag aaagtgtatg taaccgacaa caaaaaacta    780
ataggaatat ataggatgaa gagatgagag aaccatcaca gaattgacgc ttagacaact    840
taataacaca ttgcggatac ggccatgctg gccgcccggg catggtaccc aattcccgat    900
ctagtaacat agatgacacc gcgcgcgata atttatccta gtttgcgcgc tatattttgt    960
tttctatcgc gtattaaatg tataattgcg ggactctaat cataaaaacc catctcataa   1020
ataacgtcat gcattacatg ttaattatta catgcttaac gtaattcaac agaaattata   1080
tgataatcat cgcaagaccg gcaacaggat tcaatcttaa gaaactttat tgccaaatgt   1140
ttgaacgatc ggggaaattc ggggatctag agctcgactc atatctgggt aactggccta   1200
actggccttg gaggagctgg caactcaaaa tcccttttgcc aaaaaccaac atcatgccat   1260
ccaccatgct tgtatccagc tgcgcgcaat gtaccccggg ctgtgtatcc caaagcctca   1320
tgcaacctaa cagatggatc gtttggaagg cctataacag caaccacaga cttaaaacct   1380
tgcgcctcca tagacttaag caaatgtgtg tacaatgtag atcctaggcc caacctttga   1440
tgcctatgtg acacgtaaac agtactctca actgtccaat cgtaagcgtt cctagccttc   1500
cagggcccag cgtaagcaat accagccaca acaccctcaa cctcagcaac caaccaaggg   1560
tatctatctt gcaacctctc tagatcatca atccactctt gtggtgtttg tggctctgtc   1620
ctaaagttca ctgtagacgt ctcaatgtaa tggttaacga tatcacaaac cgcggccata   1680
tcagctgctg tagctggcct aatctcaact ggtctcctct ccggagacat ggtgggatcc   1740
tgtaattgta aatagtaatt gtaatgttgt ttgttgtttg ttgttgttgg taattgttgt   1800
aaaaatactc gagggtttat gttttttacaa acgactccaa caaagtatca agttttattc   1860
aaacagaatg atacagattt aaatatcggg ttttatacaa accatatgat atttatcaat   1920
tcagtgatcc tatacggacg gtggagacaa aaatcatcaa gaatcatctt tgagatgaga   1980
aagcttagct cttacctgtt ttcgtcgtct tggctttttct tcttcctggc cacctgcctg   2040
aatacttcgc cgccttgact acttctaggc tacttgctct cttttctctct ctaggactat   2100 ctctctgaga ttttgctccc ttaacaatga gggaggggct aagtatttat agactgacgg   2160
gtgagtggac atttcccaaa ctaccccttac ttatttcgta agcccttacg tcattgctcc   2220
attattggag tctgaagatg ccttcacatg gtgaccccc acctgtcggc cacgaatctt   2280
atttgttcgt cagaaaaagc caaaccgact gcacagtttt tccatcgtgg tagggaccac   2340
tttggtattg attaaaggca gccgacctaa cctttgtcag acgcattatt tcacgcgttt   2400
tcttttacag attccatctt catttgtggg acagtatgtc tgccactttg tctgccagta   2460
attaaacgcg gtccggatct agtaacatag atgacaccgc gcgcgataat ttatcctagt   2520
```

```
ttgcgcgcta tattttgttt tctatcgcgt attaaatgta taattgcggg actctaatca    2580
taaaaaccca tctcataaat aacgtcatgc attacatgtt aattattaca tgcttaacgt    2640
aattcaacag aaattatatg ataatcatcg caagaccggc aacaggattc aatcttaaga    2700
aactttattg ccaaatgttt gaacgatctg caggtcgacc catggcgccg atatcactag    2760
ttcagatctg ggtaactggc ctaactggcc ttggaggagc tggcaactca aaatccctt     2820 gccaaaaacc aacatcatgc catccaccat gcttgtatcc agctgcgcgc aatgtacccc    2880
gggctgtgta tcccaaagcc tcatgcaacc taacagatgg atcgtttgga aggcctataa    2940
cagcaaccac agacttaaaa ccttgcgcct ccatagactt aagcaaatgt gtgtacaatg    3000
tggatcctag gcccaacctt tgatgcctat gtgacacgta aacagtactc tcaactgtcc    3060
aatcgtaagc gttcctagcc ttccagggcc cagcgtaagc aataccagcc acaacaccct    3120
caacctcagc aaccaaccaa gggtatctat cttgcaacct ctctagatca tcaatccact    3180
cttgtggtgt ttgtggctct gtcctaaagt tcactgtaga cgtctcaatg taatggttaa    3240
cgatatcaca aaccgcggcc atatcagctg ctgtagctgg cctaatctca actggtctcc    3300
tctccggaga catggtggac tagtgatttc agcgtgtcct ctccaaatga aatgaacttc    3360
cttatataga ggaagggtct tgcgaaggat agtgggattg tgcgtcatcc cttacgtcag    3420
tggagatatc acatcaatcc acttgctttg aagacgtggt tggaacgtct tcttttcca    3480 cgatgctcct cgtgggtggg ggtccatctt tgggaccact gtcggcagag gcatcttcaa    3540
cgatggcctt tcctttatcg caatgatggc atttgtagga gccaccttcc ttttccacta    3600
tcttcacaat aaagtgacag atagctgggc aatggaacct ttgctgctgc acatggactt    3660
gctgtcagat ctgttggagc ttaatatccg gaaacctcct cggattccat tgcccagcta    3720
tctgtcactt tattgtgaag atagtggaaa aggaaggtgg ctcctacaaa tgccatcatt    3780
gcgataaagg aaaggctatc gttgaagatg cctctgccga cagtggtccc aaagatggac    3840
ccccacccac gaggagcatc gtggaaaaag aagacgttcc aaccacgtct tcaaagcaag    3900
tggattgatg tgatatctcc actgacgtaa gggatgacga acaatcccac tatccttctg    3960
caggtcgact ctagaggatc ctataaatag gaagttcatt tcatttggag aggaaacctc    4020
gagtattttt acaacaatta ccaacaacaa caaacaacaa acaacattac aattactatt    4080
tacaattaca catatgcctc caacaccagc tactgctact ggagctgctg ctgctgccgt    4140
tacaccagaa catgctgcaa ggtcattccc tagagttgtt cgcgttaacc ctaggtctga    4200
cagattccct gttctgtcct tccatcatgt ggagctttgg tgtgctgatg cagctagtgc    4260
tgctggtcgt ttcagctttg cacttggagc accacttgct gcaagatctg atctgtctac    4320
agggaactca gcacatgctt ctctcctact tcgatctgga gcattagcct tcctttttac    4380
cgctccttat gctccacctc cacaagaagc tgcaactgct gcaactgctt ccattccctc    4440
cttttcagca gatgctgcaa gaaccttttgc tgctgcacat ggacttgctg tcagatctgt    4500
tggagttagg gttgctgatg cagctgaagc atttcgcgtt agtgttgctg gaggagcaag    4560
acctgctttt gctccagcag atcttggtca cggatttgga cttgctgaag tggagctgta    4620
tggagatgtg gttctgagat tcgtgagcta tcctgacgaa actgacctac catttctccc    4680
aggattcgag agggtttcaa gtccaggtgc agttgactac ggtttgactc gctttgacca    4740
cgttgttgga aacgttccag aaatggctcc tgtcatcgac tacatgaagg gattccttgg    4800
tttccacgag ttcgctgaat tcacagcaga ggatgttgga accacagaat ctggactgaa    4860
```

```
cagtgtggtt ctagccaaca acagtgaagc tgttcttctg ccattgaacg agcctgttca    4920
tggaaccaag agacgatctc agatccaaac ctacctcgaa taccatggtg gaccaggagt    4980
tcaacacatc gcattggctt ctaacgatgt gcttcgaact ctcagggaaa tgagagccag    5040
aactccaatg ggagggttcg aatttatggc tcctccacaa gccaagtact atgaaggagt    5100
ccgtagaatc gctggagatg tcttgtcaga ggaacagatc aaggagtgtc aagaactggg    5160
tgttctcgtt gatcgagacg atcaaggtgt gctactccag atcttcacca aaccagttgg    5220
tgatcgtccc actttttcc tcgaaatgat tcagcgaata ggatgcatgg agaaggatga     5280
agttgggcaa gagtaccaga aaggtggatg tggtgggttt ggaaagggga acttttccga    5340
gttgttcaag tccatagagg actacgagaa gtcactggaa gtcaagcagt ctgtcgttgc    5400
tcagaagagc taagagctct tcatatgacg atcgttcaaa catttggcaa taaagtttct    5460
taagattgaa tcctgttgcc ggtcttgcga tgattatcat ataatttctg ttgaattacg    5520
ttaagcatgt aataattaac atgtaatgca tgacgttatt tatgagatgg ttttttatga    5580
ttagagtccc gcaattatac atttaatacg cgatagaaaa caaatatag cgcgcaaact      5640 aggataaatt atcgcgcgcg tgtcatcta  tgttactaga tcgcggaccc agtcaaagat     5700
tcaaatagag gacctaacag aactcgccgt aaagactggc gaacagttca tacagagtct    5760
cttacgactc aatgacaaga agaaaatctt cgtcaacatg gtggagcacg acacgcttgt    5820
ctactccaaa aatatcaaag atacagtctc agaagaccaa agggcaattg agacttttca    5880
acaaagatga cttttcaaca aagggtaata tccggaaacc tcctcggatt ccattgccca    5940
gctatctgtc actttattgt gaagatagtg aaaaggaag gtggctccta caaatgccat     6000
cattgcgata aggaaaggc atcgttgaa  gatgcctctg ccgacagtgg tcccaaagat     6060
ggacccccac ccacgaggag catcgtgaa  aagaagacg ttccaaccac gtcttcaaag     6120
caagtggatt gatgtgatat ctccactgac gtaagggatg acgcacaatc ccactatcct    6180
tcgcaagacc cttcctctat ataaggaagt tcatttcatt tggagaggac acgctgaaat    6240
cactagtcca ccatgtctcc ggagaggaga ccagttgaga ttaggccagc tacagcagct    6300
gatatggccg cggtttgtga tatcgttaac cattacattg agacgtctac agtgaacttt    6360
aggacagagc cacaaacacc acaagagtgg attgatgatc tagagaggtt gcaagataga    6420
tacccttggt tggttgctga ggttgagggt gttgtggctg gtattgctta cgctgggccc    6480
tggaaggcta ggaacgctta cgattggaca gttgagagta ctgtttacgt gtcacatagg    6540
catcaaaggt tgggcctagg atccacattg tacacacatt tgcttaagtc tatgaggcg     6600 caaggtttta agtctgtggt tgctgttata ggccttccaa acgatccatc tgttaggttg    6660
catgaggctt tgggatacac agcccggggt acattgcgcg cagctggata caagcatggt    6720
ggatggcatg atgttggttt ttggcaaagg gattttgagt tgccagctcc tccaaggcca    6780
gttaggccag ttacccagat ctgaactagt gatatcggcg ccatgggtcg acctgcagat    6840
cgttcaaaca tttggcaata aagtttctta agattgaatc ctgttgccgg tcttgcgatg    6900
attatcatat aatttctgtt gaattacgtt aagcatgtaa taattaacat gtaatgcatg    6960
acgttattta tgagatgggt ttttatgatt agagtcccgc aattatacat ttaatacgcg    7020
atagaaaaca aaatatagcg cgcaaactag gataaattat cgcgcgcggt gtcatctatg    7080
ttactagatc cggaccgcgt ttaattactg gcagacaaag tggcagacat actgtcccac    7140
aaatgaagat ggaatctgta aaagaaaacg cgtgaaataa tgcgtctgac aaaggttagg    7200
tcggctgcct ttaatcaata ccaaagtggt ccctaccacg atggaaaaac tgtgcagtcg    7260
```

-continued

```
gtttggcttt ttctgacgaa caaataagat tcgtggccga caggtgggg tccaccatgt    7320 gaaggcatct tcagactcca ataatggagc aatgacgtaa gggcttacga aataagtaag    7380
ggtagtttgg gaaatgtcca ctcacccgtc agtctataaa tacttagccc ctccctcatt    7440
gttaagggag caaaatctca gagagatagt cctagagaga gaaagagagc aagtagccta    7500
gaagtagtca aggcggcgaa gtattcaggc aggtggccag gaagaagaaa agccaagacg    7560
acgaaaacag gtaagagcta agctttctca tctcaaagat gattcttgat gattttttgtc    7620 tccaccgtcc gtataggatc actgaattga taaatatcat atggtttgta taaacccga    7680 tatttaaatc tgtatcattc tgtttgaata aaacttgata ctttgttgga gtcgtttgta    7740
aaaacataaa ccctcgagta ttttttacaac aattaccaac aacaacaaac aacaaacaac    7800
attacaatta ctatttacaa ttacaggatc ccaccatgtc tccggagagg agaccagttg    7860
agattaggcc agctacagca gctgatatgg ccgcggtttg tgatatcgtt aaccattaca    7920
ttgagacgtc tacagtgaac tttaggacag agccacaaac accacaagag tggattgatg    7980
atctagagag gttgcaagat agatacccctt ggttggttgc tgaggttgag ggtgttgtgg    8040
ctggtattgc ttacgctggg ccctggaagg ctaggaacgc ttacgattgg acagttgaga    8100
gtactgttta cgtgtcacat aggcatcaaa ggttgggcct aggatctaca ttgtacacac    8160
atttgcttaa gtctatggag gcgcaaggtt ttaagtctgt ggttgctgtt ataggccttc    8220
caaacgatcc atctgttagg ttgcatgagg ctttgggata cacagcccgg ggtacattgc    8280
gcgcagctgg atacaagcat ggtggatggc atgatgttgg ttttttggcaa agggattttg    8340 agttgccagc tcctccaagg ccagttaggc cagttaccca gatatgagtc gagctctaga    8400
tccccgaatt tccccgatcg ttcaaacatt tggcaataaa gtttcttaag attgaatcct    8460
gttgccggtc ttgcgatgat tatcatataa tttctgttga attacgttaa gcatgtaata    8520
attaacatgt aatgcatgac gttatttatg agatgggttt ttatgattag agtcccgcaa    8580
ttatacattt aatacgcgat agaaaacaaa atatagcgcg caaactagga taaattatcg    8640
cgcgcggtgt catctatgtt actagatcgg gaattgggta ccatgcccgg gcggccagca    8700
tggccgtatc cgcaatgtgt tattaagttg tctaaaccct aaaccaatgg cacacaaaaa    8760
ttcccatcct agttttttgga gtaattaatg aactagcaat tatataataa gctctgtatc    8820
tgttatattc tgcattaatt ttgttgaata aaaaacactg taaattaatt ggtcatgtgt    8880 tatatttttgc acactaattt ttttttttaaa aaggtggga gagcgtgata tttttagttg    8940
tccagaaaat aaagattgaa aaatttgaat gtatttggca cgtgggatac tttaaaaatt    9000
agaaggcacc ttattgttta cttcgatcgg agaaaaataa taaaatcctt tatatgttaa    9060
tttatttcaa tttgtatgtc tgtagtagga atattaaagt agacatttat cattaatctc    9120
attattagtc tttccttttg tagaatctcg ttaatttat taactaactt ttaaataact    9180
ctctagagga atggaacaaa ataata                                          9206
```

<210> SEQ ID NO 11
<211> LENGTH: 14
<212> TYPE: DNA
<213> ORGANISM: Artificial Sequence
<220> FEATURE:
<223> OTHER INFORMATION: PCR primer

<400> SEQUENCE: 11
cgggcggcca gcat                                                          14

```
<210> SEQ ID NO 12
<211> LENGTH: 24
<212> TYPE: DNA
<213> ORGANISM: Artificial Sequence
<220> FEATURE:
<223> OTHER INFORMATION: PCR primer

<400> SEQUENCE: 12
gtgccattgg tttagggttt agac                                              24

<210> SEQ ID NO 13
<211> LENGTH: 19
<212> TYPE: DNA
<213> ORGANISM: Artificial Sequence
<220> FEATURE:
<223> OTHER INFORMATION: Probe for TaqMan assay

<400> SEQUENCE: 13
atccgcaatg tgttattaa                                                    19

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
gccgtatccg caatgtgtta                                                   20

<210> SEQ ID NO 15
<211> LENGTH: 25
<212> TYPE: DNA
<213> ORGANISM: Artificial Sequence
<220> FEATURE:
<223> OTHER INFORMATION: PCR primer

<400> SEQUENCE: 15
ggatgaagag atgagagaac catca                                             25

<210> SEQ ID NO 16
<211> LENGTH: 21
<212> TYPE: DNA
<213> ORGANISM: Artificial Sequence
<220> FEATURE:
<223> OTHER INFORMATION: Probe for TaqMan assay

<400> SEQUENCE: 16
taagttgtct aagcgtcaat t                                                 21

<210> SEQ ID NO 17
<211> LENGTH: 21
<212> TYPE: DNA
<213> ORGANISM: Artificial Sequence
<220> FEATURE:
<223> OTHER INFORMATION: PCR primer

<400> SEQUENCE: 17
caaggccagt taggccagtt a                                                 21

<210> SEQ ID NO 18
<211> LENGTH: 26
<212> TYPE: DNA
<213> ORGANISM: Artificial Sequence
<220> FEATURE:
<223> OTHER INFORMATION: PCR primer
```

```
<400> SEQUENCE: 18
attaacgaga ttctacaaaa ggaaag                                          26

<210> SEQ ID NO 19
<211> LENGTH: 28
<212> TYPE: DNA
<213> ORGANISM: Artificial Sequence
<220> FEATURE:
<223> OTHER INFORMATION: PCR primer

<400> SEQUENCE: 19
ggacaactaa aaatatcacg ctctccca                                        28

<210> SEQ ID NO 20
<211> LENGTH: 26
<212> TYPE: DNA
<213> ORGANISM: Artificial Sequence
<220> FEATURE:
<223> OTHER INFORMATION: PCR primer

<400> SEQUENCE: 20
actacataag aaggaggtgg agaaag                                          26

<210> SEQ ID NO 21
<211> LENGTH: 29
<212> TYPE: DNA
<213> ORGANISM: Artificial Sequence
<220> FEATURE:
<223> OTHER INFORMATION: PCR primer

<400> SEQUENCE: 21
gaggtggaga agtgtatgt aaccgacaa                                        29

<210> SEQ ID NO 22
<211> LENGTH: 66
<212> TYPE: DNA
<213> ORGANISM: Artificial Sequence
<220> FEATURE:
<223> OTHER INFORMATION: PCR product derived from Glycine max and Avena
      sativa

<400> SEQUENCE: 22
cgggcggcca gcatggccgt atccgcaatg tgttattaag ttgtctaaac cctaaaccaa     60
tggcac                                                                66

<210> SEQ ID NO 23
<211> LENGTH: 70
<212> TYPE: DNA
<213> ORGANISM: Artificial Sequence
<220> FEATURE:
<223> OTHER INFORMATION: PCR product derived from Glycine max and Avena
      sativa

<400> SEQUENCE: 23
ggatgaagag atgagagaac catcacagaa ttgacgctta gacaacttaa taacacattg     60
cggatacggc                                                            70

<210> SEQ ID NO 24
<211> LENGTH: 217
<212> TYPE: DNA
<213> ORGANISM: Glycine max

<400> SEQUENCE: 24
```

-continued

```
ttacatatac tacataagaa ggaggtggag aaagtgtatg taaccgacaa caaaaaacta        60
ataggaatat ataggatgaa gagatgagag aaccatcaca gattggacgg tgggggacca       120
atggcacaca aaaattccca tcctagtttt tggagtaatt aatgaactag caattatata       180
ataagctctg tatctgttat attctgcatt aattttg                                217

<210> SEQ ID NO 25
<211> LENGTH: 21
<212> TYPE: DNA
<213> ORGANISM: Artificial Sequence
<220> FEATURE:
<223> OTHER INFORMATION: PCR primer

<400> SEQUENCE: 25
ttttgtggtc gtcactgcgt t                                                  21

<210> SEQ ID NO 26
<211> LENGTH: 40
<212> TYPE: DNA
<213> ORGANISM: Artificial Sequence
<220> FEATURE:
<223> OTHER INFORMATION: PCR primer

<400> SEQUENCE: 26
caggatatat tgtggtgtaa acaaattgac gcttagacaa                              40

<210> SEQ ID NO 27
<211> LENGTH: 35
<212> TYPE: DNA
<213> ORGANISM: Artificial Sequence
<220> FEATURE:
<223> OTHER INFORMATION: PCR primer

<400> SEQUENCE: 27
gagtcccgca attatacatt taatacgcga tagaa                                   35

<210> SEQ ID NO 28
<211> LENGTH: 29
<212> TYPE: DNA
<213> ORGANISM: Artificial Sequence
<220> FEATURE:
<223> OTHER INFORMATION: PCR primer

<400> SEQUENCE: 28
ggccagcatg gccgtatccg caatgtgtt                                          29
```

SOYBEAN EVENT SYHT0H2 AND COMPOSITIONS AND METHODS FOR DETECTION THEREOF

REFERENCE TO RELATED APPLICATIONS

This application claims the priority benefit under Title 35, United States Code 119(e) of U.S. Provisional Patent Application No. 61/423,131 filed Dec. 15, 2010, U.S. Provisional Patent Application No. 61/467,621 filed Mar. 25, 2011, and International Patent Application No. PCT/US2011/064143 filed Dec. 9, 2011.

STATEMENT REGARDING ELECTRONIC SUBMISSION OF A SEQUENCE LISTING

A Sequence Listing in ASCII test format, submitted under 37 C.F.R. 1.821, entitled "72722_WO_PCT1_06Dec2011_SEQLISTcorrected.txt", 32 kilobytes in size, generated on Dec. 6, 2011 and filed via EFS-Web is provided in lieu of a paper copy. This sequence listing is hereby incorporated by reference into the specification for its disclosure.

FIELD OF THE INVENTION

The present invention generally relates to transgenic plants with herbicide tolerance. In particular, the present invention provides soybean plants that include transformation event SYHT0H2, which confers resistance to HPPD inhibitor herbicides and to glufosinate. Also provided are methods for detecting transformation event SYHT0H2 and methods for using the disclosed plants and plant parts.

BACKGROUND OF THE INVENTION

The expression of heterologous genes in plants is known to be influenced by their location in the plant genome, perhaps due to chromatin structure or the proximity of transcriptional regulatory elements close to the integration site. At the same time, the presence of the transgene at different locations in the genome influences the overall phenotype of the plant in different ways. For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may be differences in spatial or temporal patterns of expression, for example, differences in the relative expression of a transgene in various plant tissues, that may not correspond to the patterns expected from transcriptional regulatory elements present in the introduced gene construct. It has also been observed that the transgene insertion can affect the endogenous gene expression. For these reasons, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for use in environmental monitoring, monitoring traits in crops in the field, for monitoring products derived from a crop harvest, and/or for use in ensuring compliance of parties subject to regulatory or contractual terms. Methods and compositions that allow for the rapid identification of events in plants that show herbicide tolerance may be used for crop protection and weed management, for example, to reduce the number of herbicide applications necessary to control weeds in a field, to reduce the amount of herbicide necessary to control weeds in a field, to reduce the amount of tilling necessary to produce a crop, and/or to develop programs which delay or prevent the appearance of herbicide-resistant weeds. A continuing need exists for methods and compositions of crop protection and weed management which allow the targeted use of particular herbicide combinations and for the efficient detection of such an event.

To meet this need, the present invention provides soybean plants that include transformation event SYHT0H2, which confers resistance to HPPD inhibitor herbicides and to glufosinate. Also provided are compositions and methods for detecting transformation event SYHT0H2.

SUMMARY OF THE INVENTION

The present invention provides a soybean plant or part thereof, wherein the plant or plant part comprises the polynucleotide sequence of SEQ ID NO: 1 and SEQ ID NO: 2, and which produces an amplicon diagnostic for event SYHT0H2. Also provided are soybean commodities produced from the soybean plant or plant part.

The present invention further provides isolated nucleic acids that are diagnostic for soybean event SYHT0H2, for example, any one of SEQ ID NOs: 1-6 and 9-10, or diagnostic fragments thereof.

Further provided are kits for identifying event SYHT0H2 in a biological sample. In one aspect of the invention, the kit comprises a first and a second primer, wherein the first and the second primer amplify a polynucleotide comprising a SYHT0H2 specific region. In another aspect of the invention, the kit comprises at least one nucleic acid probe that hybridizes under stringent conditions to a SYHT0H2 specific region.

Further provided are methods of identifying event SYHT0H2 in a sample. In one aspect of the invention, the method comprises the steps of (a) contacting the sample with a first and a second primer; and (b) amplifying a nucleic acid comprising a SYHT0H2 specific region. In another aspect of the invention, the method comprises (a) contacting the sample with at least one nucleic acid probe that hybridizes under stringent conditions to a SYHT0H2 specific region; and (b) detecting hybridization of the at least one nucleic acid probe to the SYHT0H2 specific region.

Still further provided are methods of producing a soybean plant resistant to an HPPD inhibitor and/or glufosinate comprising introducing into the genome of the soybean plant event SYHT0H2. Methods of producing a soybean commodity product using such plants are also provided.

Still further provided are methods of controlling weeds at a location comprising soybean plants and weeds, wherein the soybean plants comprise event SYHT0H2, and wherein the method comprises applying to the location a weed controlling amount of an herbicidal composition comprising one or more HPPD inhibitors.

Still further provided are methods of improving soybean yield using event SYHT0H2.

Still further provided are methods of controlling volunteer SYHT0H2 crop plants at a location wherein the method comprises applying to the location one or more herbicides effective on soybeans and having a mode of action other than inhibition of HPPD.

Still further provided are methods of controlling volunteer transgenic events at a location comprising SYHT0H2 crop plants wherein the volunteer events comprise resistance to one or more herbicides but do not comprise resistance to HPPD inhibitors wherein the method comprises applying to the location a controlling amount of an herbicidal composition comprising one or more HPPD inhibitors.

Still further provided are methods of applying herbicidal mixtures to a location wherein the herbicidal mixture comprises an HPPD inhibitor and at least one additional chemical that may not be tolerated by SYHT0H2 for the purpose of pest control (weeds, disease, insect, nematode) wherein the presence of the SYHT0H2 event allows application of this mixture either pre-planting or pre-emergence by protecting against residual HPPD activity. Still further provided are a soybean chromosomal target site for insertion of a heterologous nucleic acid, which corresponds to the insertion site of event SYHT0H2. Also provided are soybean plants, plant parts, and commodity products comprising a heterologous nucleic acid at a chromosomal site of event SYHT0H2 and methods for making the same.

BRIEF DESCRIPTION OF THE DRAWINGS

FIG. 1 is a representation of binary vector 15954 containing a soybean codon optimized *Avena* HPPD gene.

BRIEF DESCRIPTION OF SEQUENCES IN THE SEQUENCE LISTING

TABLE 1

| SEQ ID NO. | Description |
|---|---|
| 1 | 20 bp LB2 junction (10 bp flanking/10 bp insert) |
| 2 | 20 bp LB1 junction (3 bp insert/17 bp flanking) |
| 3 | 40 bp LB2 junction (20 bp flanking/20 bp insert) |
| 4 | 40 bp LB1 junction (13 bp insert/27 bp flanking) |
| 5 | 60 bp LB2 junction (30 bp flanking/30 bp insert) |
| 6 | 60 bp LB1 junction (23 bp insert/37 bp flanking) |
| 7 | LB2 flanking genomic sequence (99 bp) |
| 8 | LB1 flanking genomic sequence (462 bp) |
| 9 | Complete insert |
| 10 | Insert plus flanking genomic sequence |
| 13, 16 | Probes used for TAQMAN ® assay |
| 11-12, 14-15, 17-21 | Primer sequences used in amplification assays |
| 22-23 | TAQMAN ® assay amplification products |
| 24 | Gm08: 9905210-9905426 |
| 25-28 | Primer sequences used for sequencing |

DETAILED DESCRIPTION OF THE INVENTION

Compositions and methods related to transgenic HPPD inhibitor tolerant soybean plants are provided. Compositions of the invention include soybean plants and plant parts comprising event SYHT0H2, food and feed commodities derived therefrom, and reagents for detecting the same. A soybean plant comprising event SYHT0H2 has been generated by the insertion of a mutant HPPD gene derived from *Avena* and a phosphinothricin acetyl transferase gene from *S. viridochromogenes*, as described in Example 1.

As used herein, the abbreviation "HPPD" means hydroxyphenyl-pyruvate-dioxygenase. HPPD polynucleotides encode polypeptides having the enzymatic activity of a hydroxyphenyl-pyruvate-dioxygase enzyme.

The polynucleotides conferring HPPD inhibitor tolerance are inserted at a characterized position in the soybean genome and thereby produce the SYHT0H2 soybean event. See Example 3. A soybean plant harboring event SYHT0H2 comprises genomic/transgene junctions having at least the polynucleotide sequence of SEQ ID NO: 1 or 2. The characterization of the genomic insertion site of event SYHT0H2 provides for an enhanced breeding efficiency and enables the use of molecular markers to track the transgene insert in the breeding populations and progeny thereof. See Example 4. Various methods and compositions for the identification, detection, and use of the soybean SYHT0H2 event are provided herein. See e.g., Example 2. As used herein, the description "SYHT0H2 specific," as used to describe a nucleic acid or nucleotide sequence, refers to a quality of discriminatively identifying event SYHT0H2 in plants, plant material, or in products such as, but not limited to, food or feed products (fresh or processed) containing or derived from plant material.

Compositions further include seed deposited as the American Type Culture Collection (ATCC) Deposit No. PTA-11226, and plants, plant cells, and seed derived therefrom. Applicant made a deposit of at least 2500 seeds of soybean event SYHT0H2 with the ATCC, Manassas, Va. 20110-2209 U.S.A., on Jul. 21, 2010, and the deposits were assigned ATCC Deposit No. PTA-11226. These deposits will be maintained under the terms of the Budapest Treaty on the International Recognition of the Deposit of Microorganisms for the Purposes of Patent Procedure.

As used herein, the term "soybean" means *Glycine max* and includes all plant varieties that can be bred with soybean. As used herein, the term plant includes plant cells, plant organs, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, stalks, roots, root tips, anthers, and the like. Grain is intended to mean the mature seed produced by commercial growers for purposes other than growing or reproducing the species. Progeny, variants, and mutants of the regenerated plants are included within the scope of the invention, provided that these parts comprise event SYHT0H2.

Compositions of the invention further comprise a commodity, such as a food or feed product comprising or derived from one or more of the following products of a soybean plant comprising event SYHT0H2: lecithin, fatty acids, glycerol, sterol, edible oil, defatted soy flakes, soy meals including defatted and toasted soy meals, soy milk curd, tofu, soy flour, soy protein concentrate, isolated soy protein, hydrolyzed vegetable protein, textured soy protein, and soy protein fiber.

A transgenic "event" is produced by transformation of plant cells with a heterologous DNA construct(s), including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene(s). At the genetic level, an event is part of the genetic makeup of a plant. The term "event" refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

The average and distribution of herbicide tolerance or resistance levels of a range of primary plant transformation events are evaluated in the normal manner based upon plant damage, meristematic bleaching symptoms, etc. at a range of different concentrations of any given herbicide. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent inhibitor-tolerance (e.g., increased $Ki/Km_{HPP}$ value) and/or level of expression of the expressed HPPD polypeptide.

As used herein, "insert DNA" refers to the heterologous DNA within the expression cassettes used to transform the plant material while "flanking DNA" can comprise either genomic DNA naturally present in an organism such as a plant, or foreign (heterologous) DNA introduced via the transformation process which is extraneous to the original insert DNA molecule, e.g., fragments associated with the transformation event. A "flanking region" or "flanking sequence" as used herein refers to a sequence of at least 20, 50, 100, 200, 300, 400, 1000, 1500, 2000, 2500, or 5000 base pair or greater which is located either immediately upstream of and contiguous with or immediately downstream of and contiguous with the original foreign insert DNA molecule. Non-limiting examples of the flanking regions of event SYHT0H2 are set forth in SEQ ID NO: 7 and 8 and variants and fragments thereof.

Transformation procedures leading to random integration of the foreign DNA will result in transformants containing different flanking regions characteristic of and unique for each transformant. When recombinant DNA is introduced into a plant through traditional crossing, its flanking regions will generally not be changed. Transformants will contain unique junctions between a piece of heterologous insert DNA and genomic DNA, or two pieces of genomic DNA, or two pieces of heterologous DNA. A "junction" is a point where two specific DNA fragments join. For example, a junction exists where insert DNA joins flanking DNA. A junction point exists in a transformed organism where two DNA fragments join together in a manner that is modified from that found in the native organism. As used herein, "junction DNA" refers to DNA that comprises a junction point. Non-limiting examples of junction DNA from event SYHT0H2 set are forth as SEQ ID NOs:1-6, and variants and fragments thereof.

A plant comprising event SYHT0H2 can be bred by first sexually crossing a first parental soybean plant grown from the transgenic SYHT0H2 soybean plant and a second parental soybean plant that lacks the herbicide tolerance phenotype, thereby producing a plurality of first progeny plants; and then selecting a first progeny plant that displays the desired herbicide tolerance; and selfing the first progeny plant, thereby producing a plurality of second progeny plants; and then selecting from the second progeny plants which display the desired herbicide tolerance. These steps can further include the back-crossing of the herbicide tolerant progeny plant to the second parental soybean plant or a third parental soybean plant, thereby producing a soybean plant that displays the desired herbicide tolerance. It is further recognized that assaying progeny for phenotype is not required. Various methods and compositions, as disclosed elsewhere herein, can be used to detect and/or identify event SYHT0H2.

It is understood that two different transgenic plants can be sexually crossed to produce offspring that contain two independently segregating added, exogenous genes. Selfing of appropriate progeny can produce plants that are homozygous for both added, exogenous genes. Back-crossing to a parental plant and out-crossing with a non-transgenic plant are contemplated, as is vegetative propagation. Descriptions of other breeding methods that are commonly used for different traits and crops can be found in one of several references, e.g., Fehr, in *Breeding Methods for Cultivar Development*, 1987, Wilcos, J. (ed.), American Society of Agronomy, Madison, Wis.

The term "germplasm" refers to an individual, a group of individuals, or a clone representing a genotype, variety, species or culture, or the genetic material thereof.

A "line" or "strain" is a group of individuals of identical parentage that are generally inbred to some degree and that are generally isogenic or near isogenic.

Inbred soybean lines are typically developed for use in the production of soybean hybrids and for use as germplasm in breeding populations for the creation of new and distinct inbred soybean lines. Inbred soybean lines are often used as targets for the introgression of novel traits through traditional breeding and/or molecular introgression techniques. Inbred soybean lines need to be highly homogeneous, homozygous and reproducible to be useful as parents of commercial hybrids. Many analytical methods are available to determine the homozygosity and phenotypic stability of inbred lines.

The phrase "hybrid plants" refers to plants which result from a cross between genetically different individuals.

The term "crossed" or "cross" in the context of this invention means the fusion of gametes, e.g., via pollination to produce progeny (i.e., cells, seeds, or plants) in the case of plants. The term encompasses both sexual crosses (the pollination of one plant by another) and, in the case of plants, selfing (self-pollination, i.e., when the pollen and, ovule are from the same plant).

The term "introgression" refers to the transmission of a desired allele of a genetic locus from one genetic background to another. In one method, the desired alleles can be introgressed through a sexual cross between two parents, wherein at least one of one of the parents has the desired allele in its genome.

In some aspects of the invention, the polynucleotide conferring the event SYHT0H2 is engineered into a molecular stack. In other aspects, the molecular stack further comprises at least one additional polynucleotide that confers tolerance to a third herbicide. For example, the sequence can confer tolerance to glyphosate, and the sequence can comprise EPSPS.

In other aspects of the invention, event SYHT0H2 can comprise one or more additional traits of interest, for example, stacking with any combination of polynucleotide sequences of interest in order to create plants with a desired combination of traits. A trait, as used herein, refers to the phenotype derived from a particular sequence or groups of sequences. For example, herbicide tolerance polynucleotides may be stacked with any other polynucleotides encoding polypeptides having pesticidal and/or insecticidal activity, such as *Bacillus thuringiensis* toxic proteins (described in U.S. Pat. Nos. 5,366,892; 5,747,450; 5,737,514; 5,723,756; and 5,593,881; Geiser et al., *Gene*, 1986 48:109; Lee et al., *Appl. Environ. Microbiol.*, 2003, 69:4648-4657 (Vip3A); Galitzky et al., *Acta Crystallogr. D. Biol. Crystallog.*, 2001, 57:1101-1109 (Cry3Bb1); and Herman et al., *J. Agric. Food Chem.*, 2004, 52:2726-2734 (CrylF)), lectins (Van Damme et al., *Plant Mol. Biol.*, 1994, 24:825, pentin (described in U.S. Pat. No. 5,981,722), and the like. The combinations generated can include multiple copies of any one of the polynucleotides of interest. These combinations may also be generated through breeding stacks with existing or new events comprising these genes. Examples of existing events that may be used in a breeding stack include but are not limited to: MON87701—lepidopteran resistance.

In some aspects of the invention, event SYHT0H2 may be stacked with other herbicide tolerance traits to create a transgenic plant of the invention with further improved properties. For example, the polynucleotides encoding a mutant HPPD polypeptide or variant thereof that retains HPPD enzymatic activity may be stacked with any other polynucleotides encoding polypeptides that confer a desirable trait, including but not limited to resistance to diseases, insects, and herbicides, tolerance to heat and drought, reduced time to crop maturity, improved industrial processing, such as for the conversion of starch or biomass to fermentable sugars, and improved agronomic quality, such as high oil content and high protein content.

Exemplary polynucleotides that may be stacked with polynucleotides of the invention encoding an mutant HPPD polypeptide or variant thereof that retains HPPD enzymatic activity include polynucleotides encoding polypeptides conferring resistance to pests/pathogens such as viruses, nematodes, insects or fungi, and the like. Exemplary polynucleotides that may be stacked with polynucleotides of the invention include polynucleotides encoding: polypeptides having pesticidal and/or insecticidal activity, such as other *Bacillus thuringiensis* toxic proteins (described in U.S. Pat. Nos. 5,366,892; 5,747,450; 5,737,514; 5,723,756; and 5,593,881; and Geiser et al., *Gene*, 1986, 48:109), lectins (Van Damme et al., *Plant Mol. Biol.*, 1994, 24:825, pentin (described in U.S. Pat. No. 5,981,722), and the like; traits desirable for disease or herbicide resistance (e.g., fumonisin detoxification genes (U.S. Pat. No. 5,792,931); avirulence and disease resistance genes (Jones et al., *Science*, 1994, 266:789; Martin et al., *Science*, 1993, 262:1432; Mindrinos et al., *Cell*, 1993, 78:1089); acetolactate synthase (ALS) mutants that lead to herbicide resistance such as the S4 and/or Hra mutations ((resistance to herbicides including sulfonylureas, imidazolinones, triazolopyrimidines, pyrimidinyl thiobenzoates); glyphosate resistance (e.g., 5-enol-pyrovyl-shikimate-3-phosphate-synthase (EPSPS) gene, including but not limited to those described in U.S. Pat. Nos. 4,940,935, 5,188,642, 5,633,435, 6,566,587, 7,674,598 as well as all related application; or the glyphosate N-acetyltransferase (GAT) gene, described in Castle et al., *Science*, 2004, 304:1151-1154; and in U.S. Patent Application Publication Nos. 20070004912, 20050246798, and 20050060767)); glufosinate resistance (e.g., BAR; see e.g., U.S. Pat. No. 5,561,236); 2,4-D resistance (e.g. aryloxy alkanoate dioxygenase or AAD-1, AAD-12, or AAD-13), HPPD resistance (e.g. *Pseudomonas* HPPD) and PPO resistance (e.g., fomesafen, acifluorfen-sodium, oxyfluorfen, lactofen, fluthiacet-methyl, saflufenacil, flumioxazin, flumiclorac-pentyl, carfentrazone-ethyl, sulfentrazone); a cytochrome P450 or variant thereof that confers herbicide resistance or tolerance to, inter alia, HPPD-inhibiting herbicides, PPO-inhibiting herbicides and ALS-inhibiting herbicides (U.S. Patent Application Publication No. 20090011936; U.S. Pat. Nos. 6,380,465; 6,121,512; 5,349,127; 6,649,814; and 6,300,544; and PCT International Publication No. WO 2007/000077); dicamba resistance (e.g. dicamba monoxygenase), and traits desirable for processing or process products such as high oil (e.g., U.S. Pat. No. 6,232,529); modified oils (e.g., fatty acid desaturase genes (U.S. Pat. No. 5,952,544; PCT International Publication No. WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al., *J. Bacteriol.*, 1988, 170:5837-5847) facilitate expression of polyhydroxyalkanoates (PHAs)); the disclosures of which are herein incorporated by reference.

Thus, in one aspect of the invention, event SYHT0H2 is stacked with one or more polynucleotides encoding polypeptides that confer resistance or tolerance to an herbicide, such as an HPPD inhibitor, glyphosate, 2,4-D, dicamba or glufosinate.

Other herbicide tolerance polynucleotides that could be used in such aspects of the invention include those conferring tolerance to HPPD inhibitors by other genes or modes of action. Other traits that could be combined with the soybean SYHT0H2 events include those derived from polynucleotides that confer on the plant the capacity to produce a higher level of 5-enolpyruvylshikimate-3-phosphate synthase (EPSPS), for example, as more fully described in U.S. Pat. Nos. 6,248,876; 5,627,061; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; RE 36,449; RE 37,287; and 5,491,288; and PCT International Publication Nos. WO 97/04103; WO 00/66746; WO 01/66704; and WO 00/66747. Other traits that could be combined with event SYHT0H2 include those conferring tolerance to sulfonylurea, imidazolinone triazolopyrimidines and/or pyrimidinyl thiobenzoates, for example, as described more fully in U.S. Pat. Nos. 5,605,011; 5,013,659; 5,141,870; 5,767,361; 5,731,180; 5,304,732; 4,761,373; 5,331,107; 5,928,937; and 5,378,824; and PCT International Publication No. WO 96/33270.

In some aspects of the invention, event SYHT0H2 may be stacked with, for example, hydroxyphenylpyruvatedioxygenases which are enzymes that catalyze the reaction in which para-hydroxyphenylpyruvate (HPP) is transformed into homogentisate. Molecules that inhibit this enzyme and that bind to the enzyme in order to inhibit transformation of the HPP into homogentisate are useful as herbicides. Traits conferring tolerance to such herbicides in plants are described in U.S. Pat. Nos. 6,245,968; 6,268,549; and 6,069,115; and PCT International Publication No. WO 99/23886. Other examples of suitable herbicide tolerance traits that could be stacked with event SYHT0H2 include aryloxyalkanoate dioxygenase polynucleotides (which may confer tolerance to 2,4-D and other phenoxy auxin herbicides as well as to aryloxyphenoxypropionate herbicides as described, for example, in PCT International Publication Nos. WO2005/107437, WO2007/053482 and WO2008/141154 and U.S. Pat. No. 7,820,883 and related applications and patents), homogentisate solanesyltransferase (HST) (for example as disclosed in PCT International Publication No. WO 10/029,311, and dicamba (monoxygenase) tolerance polynucleotides as described, for example, in Herman et al., *J. Biol. Chem.*, 2005, 280: 24759-24767 and U.S. Pat. No. 7,812,224 and related applications and patents.

Other examples of herbicide tolerance traits that could be combined with event SYHT0H2 include those conferred by polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616; and 5,879,903. Plants containing an exogenous phosphinothricin acetyltransferase can exhibit improved tolerance to glufosinate herbicides, which inhibit the enzyme glutamine synthase. Other examples of herbicide tolerance traits that could be combined with event SYHT0H2 include those conferred by polynucleotides conferring altered protoporphyrinogen oxidase (protox) activity, as described in U.S. Pat. Nos. 6,288,306; 6,282,837; and 5,767,373; and PCT International Publication No. WO 01/12825. Plants containing such polynucleotides can exhibit improved tolerance to any of a variety of herbicides which target the protox enzyme (referred to as "protox inhibitors").

Other examples of herbicide tolerance traits that could be combined with event SYHT0H2 include those conferring tolerance to at least one herbicide in a plant such as, for example, a soybean plant or horseweed. Herbicide tolerant weeds are known in the art, as are plants that vary in their tolerance to particular herbicides. See, e.g., Green & Williams, "Correlation of Corn (*Zea mays*) Inbred Response to Nicosulfuron and Mesotrione," poster presented at the WSSA Annual Meeting in Kansas City, Mo., Feb. 9-12, 2004; Green (1998) *Weed Technology* 12: 474-477; Green & Ulrich, Weed Science 2003, 41:508-516. The trait(s) responsible for these tolerances can be combined by breeding or via other methods with event SYHT0H2 to provide a plant of the invention as well as methods of use thereof.

The above described genes may be genetically engineered into event SYHT0H2 or combined with event SYHT0H2 through a breeding stack with a new or existing event providing tolerance to one of the aforementioned genes. Possible events for use in a breeding stack include but are not limited to: MON89788—glyphosate tolerance (U.S. Pat. No. 7,632,985 and related applications and patents), MON87708—dicamba tolerance (U.S. Patent Application Publication No. US 2011/0067134 and related applications and patents), DP-356043-5—glyphosate and ALS tolerance (U.S. Patent Application Publication No. US 2010/0184079 and related applications and patents), A2704-12—glufosinate tolerance (U.S. Patent Application Publication No. US 2008/0320616 and related applications and patents), DP-305423-1—ALS tolerance (U.S. Patent Application Publication No. US 2008/0312082 and related applications and patents), A5547-127—glufosinate tolerance (U.S. Patent Application Publication No. US 2008/0196127 and related applications and patents), DAS-40278-9—tolerance to 2,4-dichlorophenoxyacetic acid and aryloxyphenoxypropionate (PCT International Publication Nos. WO 2011/022469, WO 2011/022470, WO 2011/022471, and related applications and patents), 127—ALS tolerance (PCT International Publication Nos. WO 2010/080829 and related applications and patents), GTS 40-3-2—glyphosate tolerance, DAS-68416-4-2,4-dichlorophenoxyacetic acid and glufosinate tolerance, FG72—glyphosate and isoxaflutole tolerance, BPS-CV127-9—ALS tolerance and GU262—glufosinate tolerance, SYHT04R—HPPD tolerance.

Event SYHT0H2 can be combined with at least one other trait to produce plants of the present invention that further comprise a variety of desired trait combinations including, but not limited to, traits desirable for animal feed such as high oil content (e.g., U.S. Pat. No. 6,232,529); balanced amino acid content (e.g., hordothionins (U.S. Pat. Nos. 5,990,389; 5,885,801; 5,885,802; and 5,703,409; U.S. Pat. No. 5,850,016); barley high lysine (Williamson et al., *Eur. J. Biochem.*, 1987, 165:99-106; and PCT International Publication No. WO 98/20122) and high methionine proteins (Pedersen et al., *J. Biol. Chem.* 1986, 261:6279; Kirihara et al., *Gene*, 1988, 71:359; and Musumura et al., *Plant Mol. Biol.*, 1989, 12:123)); increased digestibility (e.g., modified storage proteins (U.S. Pat. No. 6,858,778); and thioredoxins (U.S. Pat. No. 7,009,087)); the disclosures of which are herein incorporated by reference. Desired trait combinations include LLNC (low linolenic acid content; see, e.g., Dyer et al., *Appl. Microbiol. Biotechnol.*, 2002, 59:224-230) and OLCH (high oleic acid content; see, e.g., Fernandez-Moya et al., *J. Agric. Food Chem.*, 2005, 53: 5326-5330).

Event SYHT0H2 can be combined with other desirable traits such as, for example, fumonisim detoxification genes (U.S. Pat. No. 5,792,931), avirulence and disease resistance genes (Jones et al., *Science*, 1994, 266:789; Martin et al., *Science*, 1993, 262:1432; Mindrinos et al., *Cell*, 1994, 78:1089), and traits desirable for processing or process products such as modified oils (e.g., fatty acid desaturase genes (U.S. Pat. No. 5,952,544; PCT International Publication No. WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al., *J. Bacteriol.*, 1988, 170:5837-5847) facilitate expression of polyhydroxyalkanoates (PHAs)); the disclosures of which are herein incorporated by reference. One could also combine herbicide tolerant polynucleotides with polynucleotides providing agronomic traits such as male sterility (e.g., see U.S. Pat. No. 5,583,210), stalk strength, flowering time, or transformation technology traits such as cell cycle regulation or gene targeting (e.g., PCT International Publication Nos. WO 99/61619, WO 00/17364, and WO 99/25821); the disclosures of which are herein incorporated by reference.

In another aspect of the invention, event SYHT0H2 can be combined with the Rcg1 sequence or biologically active variant or fragment thereof. The Rcg1 sequence is an anthracnose stalk rot resistance gene in corn. See, e.g., U.S. Patent Application Publication Nos. 20060225151, 20060223102, and 20060225152, each of which is herein incorporated by reference.

The above-described stacked combinations can be created by any method including, but not limited to, breeding plants by any conventional or TopCross methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, e.g., PCT International Publication Nos. WO 99/25821, WO 99/25854, WO 99/25840, WO 99/25855, and WO 99/25853, all of which are herein incorporated by reference.

As used herein, the use of the term "polynucleotide" encompasses polynucleotides comprising ribonucleotides and/or deoxyribonucleotides, including both naturally occurring molecules and synthetic analogues. The polynucleotides encompass all forms of sequences including, but not limited to, single-stranded forms, double-stranded forms, hairpins, stem-and-loop structures, and the like.

A SYHT0H2 plant comprises an expression cassette having a mutant HPPD gene and 5' and 3' regulatory sequences operably linked to the mutant HPPD gene. "Operably linked" is intended to mean a functional linkage between two or more elements. For example, an operable linkage between a polynucleotide of interest and a regulatory sequence (i.e., a promoter) is functional link that allows for the expression of the polynucleotide of interest. Operably linked elements may be contiguous or non-contiguous. When used to refer to the joining of two protein coding regions, by operably linked it is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions. The expression cassette may additionally contain selectable marker genes.

The expression cassette will include in the 5'-3' direction of transcription, a transcriptional and translational initiation region (i.e., a promoter), a coding region, and a transcriptional and translational termination region functional in plants. "Promoter" refers to a nucleotide sequence capable of controlling the expression of a coding sequence or functional RNA. In general, a coding sequence is located 3 to a promoter sequence. The promoter sequence can comprise proximal and more distal upstream elements, the latter elements are often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters." New promoters of various types useful in plant cells are constantly being discovered; numerous examples may be found in the compilation by Okamuro & Goldberg, *Biochemistry of Plants*, 1989, 15:1-82. It is further recognized that since in most cases the exact boundaries of regulatory sequences have not been completely defined, nucleic acid fragments of different lengths may have identical promoter activity.

The expression cassettes may contain 5' leader sequences. Such leader sequences can act to enhance translation. The regulatory regions (i.e., promoters, transcriptional regulatory regions, RNA processing or stability regions, introns, polyadenylation signals, and translational termination regions) and/or the coding region may be native/analogous or heterologous to the host cell or to each other.

The "translation leader sequence" refers to a nucleotide sequence located between the promoter sequence of a gene and the coding sequence. The translation leader sequence is present in the fully processed mRNA upstream of the translation start sequence. The translation leader sequence may affect numerous parameters including, processing of the primary transcript to mRNA, mRNA stability and/or translation efficiency. Examples of translation leader sequences have been described (Turner & Foster, *Mol. Biotechnol.*, 1995, 3:225-236). The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell*, 1989, 1:671-680.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and trans versions, may be involved. The expression cassette can comprise a selectable marker gene for the selection of transformed cells. Selectable marker genes are utilized for the selection of transformed cells or tissues.

Isolated polynucleotides are provided that can be used in various methods for the detection and/or identification of the soybean SYHT0H2 event. An "isolated" or "purified" polynucleotide, or biologically active portion thereof, is substantially or essentially free from components that normally accompany or interact with the polynucleotide as found in its naturally occurring environment. Thus, an isolated or purified polynucleotide is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various aspects of the invention, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. For avoidance of doubt an "isolated" sequence can still be in the context of other DNA, either in vitro or in vivo, and can for example exist in a transgenic cell or organism.

In specific aspects of the invention, the polynucleotides comprise the junction DNA sequences set forth in SEQ ID NO: 1-6. In other aspects of the invention, the polynucleotides comprise the DNA sequences set forth in SEQ ID NO: 11-12 and variants and fragments thereof. Fragments and variants of junction DNA sequences are suitable for discriminatively identifying event SYHT0H2. As discussed elsewhere herein, such sequences find use as primers and/or probes.

In other aspects of the invention, the polynucleotides are provided that can detect event SYHT0H2 or a SYHT0H2 specific region. Such sequences include any polynucleotide set forth in SEQ ID NOs: 1-20, and variants and fragments thereof. In specific aspects of the invention, the polynucleotide used to detect event SYHT0H2 comprises the sequence set forth in SEQ ID NO: 10 or a fragment of SEQ ID NO: 10 having at least 20, 30, 40, 50, 60, 70, 80, 90, 100, 110, 120, 130, 140, 150, 160, 170, or 180 nucleotides. Fragments and variants of polynucleotides that detect event SYHT0H2 or a SYHT0H2 specific region are suitable for discriminatively identifying event SYHT0H2. As discussed elsewhere herein, such sequences find use as primers and/or probes. Further provided are isolated DNA nucleotide primer sequences comprising or consisting of (a) a sequence set forth in any one of SEQ ID NOs: 11-12, 14-15, and 17-21, and (b) variants and fragments of SEQ ID NO: 10 or the complement thereof.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide.

As used herein, a "probe" is an isolated polynucleotide to which is attached a conventional detectable label or reporter molecule, e.g., a radioactive isotope, ligand, chemiluminescent agent, enzyme, etc. Such a probe is complementary to a strand of a target polynucleotide, in the instant case, to a strand of isolated DNA from soybean event SYHT0H2 whether from a soybean plant or from a sample that includes DNA from the event. Probes include not only deoxyribonucleic or ribonucleic acids but polyamides and other probe materials that can specifically detect the presence of the target DNA sequence.

As used herein, "primers" are isolated polynucleotides that are annealed to a complementary target DNA strand by nucleic acid hybridization to form a hybrid between the primer and the target DNA strand, then extended along the target DNA strand by a polymerase, e.g., a DNA polymerase. Primer pairs refer to their use for amplification of a target polynucleotide, e.g., by the polymerase chain reaction (PCR) or other conventional nucleic-acid amplification methods. "PCR" or "polymerase chain reaction" is a technique used for the amplification of specific DNA segments (see U.S. Pat. Nos. 4,683,195 and 4,800,159; herein incorporated by reference). Any combination of primers disclosed herein can be used such that the pair allows for the detection of event SYHT0H2 (e.g., primers comprising SEQ ID NOs: 11-12, 14-15, and 17-21 and variants or fragments of SEQ ID NO: 10 or the complement thereof). Non-limiting examples of primer pairs useful in the disclosed methods include (a) a first primer comprising the polynucleotide sequence of SEQ ID NO: 11 and a second primer comprising the polynucleotide sequence of SEQ ID NO: 12, which may be used to amplify a sequence spanning the LB1 (left border 1) junction of soybean genomic DNA and the inserted heterologous sequence containing the *Avena* HPPD sequence; (b) a first primer comprising the polynucleotide sequence of SEQ ID NO: 14 and a second primer comprising the polynucleotide sequence of SEQ ID NO: 15, which may be used to amplify a sequence spanning the LB2 (left border 2) junction of soybean genomic DNA and the inserted heterologous sequence containing the *Avena HPPD sequence*; (c) a first primer comprising the polynucleotide sequence of SEQ ID NO: 17 and a second primer comprising the polynucleotide sequence of SEQ ID NO: 18 or SEQ ID NO: 19, which may be used to amplify a sequence spanning the LB1 junction of soybean genomic DNA and the inserted heterologous sequence containing the *Avena* HPPD sequence; and (d) a first primer comprising the polynucleotide sequence of SEQ ID NO: 17 and a second primer comprising the polynucleotide sequence of SEQ ID NO: 20 or SEQ ID NO: 21, which may be used to amplify the LB 1 junction of soybean genomic DNA and the inserted heterologous sequence containing the *Avena* HPPD sequence. "LB 1," as used to describe the insert junction or flanking sequence refers to the 3' end of the insert and adjacent flanking sequence. "LB2," as used to describe the insert junction or flanking sequence refers to the 5' end of the insert and adjacent flanking sequence.

Probes and primers are of sufficient nucleotide length to bind to the target DNA sequence and specifically detect and/or identify a polynucleotide having event SYHT0H2. It is recognized that the hybridization conditions or reaction conditions can be determined by the operator to achieve this result. This length may be of any length that is of sufficient length to be useful in a detection method of choice. Generally, 8, 11, 14, 16, 18, 20, 22, 24, 26, 28, 30, 40, 50, 75, 100, 200, 300, 400, 500, 600, 700 nucleotides or more, or between about 11-20, 20-30, 30-40, 40-50, 50-100, 100-200, 200-300, 300-400, 400-500, 500-600, 600-700, 700-800, or more nucleotides in length are used. Such probes and primers can hybridize specifically to a target sequence under high stringency hybridization conditions. Probes and primers according to aspects of the invention may have complete DNA sequence identity of contiguous nucleotides with the target sequence, although probes differing from the target DNA sequence and that retain the ability to specifically detect and/or identify a target DNA sequence may be designed by conventional methods. Accordingly, probes and primers can share about 80%, 85%, 90%, 91%, 92%, 93%, 94%, 95%, 96%, 97%, 98%, 99% or greater sequence identity or complementarity to the target polynucleotide (i.e., SEQ ID NOs: 1-12), or can differ from the target sequence (i.e., SEQ ID NOs: 1-12) by 1, 2, 3, 4, 5, 6 or more nucleotides. Probes can be used as primers, but are generally designed to bind to the target DNA or RNA and are not used in an amplification process.

Specific primers can be used to amplify an integration fragment to produce an amplicon that can be used as a "specific probe" or can itself be detected for identifying event SYHT0H2 in biological samples. Alternatively, a probe can be used during the PCR reaction to allow for the detection of the amplification event (i.e., a TAQMAN® probe or a MGB™ probe) (so called real time PCR). When the probe is hybridized with the polynucleotides of a biological sample under conditions which allow for the binding of the probe to the sample, this binding can be detected and thus allow for an indication of the presence of event SYHT0H2 in the biological sample. Such identification of a bound probe has been described in the art. In an aspect of the invention, the specific probe is a sequence which, under optimized conditions, hybridizes specifically to a region within the 5' or 3' flanking region of the event and comprises a part of the foreign DNA contiguous therewith. The specific probe may comprise a sequence of at least 80%, between 80 and 85%, between 85 and 90%, between 90 and 95%, and between 95 and 100% identical (or complementary) to a specific region of event SYHT0H2.

As used herein, "amplified DNA" or "amplicon" refers to the product of polynucleotide amplification of a target polynucleotide that is part of a nucleic acid template. For example, to determine whether a soybean plant resulting from a sexual cross contains event SYHT0H2, DNA extracted from the soybean plant tissue sample may be subjected to a polynucleotide amplification method using a DNA primer pair that includes a first primer derived from flanking sequence adjacent to the insertion site of inserted heterologous DNA, and a second primer derived from the inserted heterologous DNA to produce an amplicon that is diagnostic for the presence of event SYHT0H2 DNA. By "diagnostic" for event SYHT0H2, the use of any method or assay which discriminates between the presence or the absence of event SYHT0H2 in a biological sample is intended. Alternatively, the second primer may be derived from the flanking sequence. In still other aspects of the invention, primer pairs can be derived from flanking sequence on both sides of the inserted DNA so as to produce an amplicon that includes the entire insert polynucleotide of the expression construct as well as the sequence flanking the transgenic insert. The amplicon is of a length and has a sequence that is diagnostic for the event (i.e., has a junction DNA from event SYHT0H2). The amplicon may range in length from the combined length of the primer pairs plus one nucleotide base pair to any length of amplicon producible by a DNA amplification protocol. A member of a primer pair derived from the flanking sequence may be located a distance from the inserted DNA sequence, this distance can range from one nucleotide base pair up to the limits of the amplification reaction, or about twenty thousand nucleotide base pairs. The use of the term "amplicon" specifically excludes primer dimers that may be formed in the DNA thermal amplification reaction.

Methods for preparing and using probes and primers are described, for example, in Sambrook et al. (eds.), *Molecular Cloning: A Laboratory Manual*, $2^{nd}$ ed, vol. 1-3, 1989, Cold Spring Harbor Laboratory Press, Cold Spring Harbor, N.Y.; Ausebel et al. (eds.), *Current Protocols in Molecular Biology*, 1992, Greene Publishing and Wiley-Interscience, New York, N.Y.; and Innis et al., *PCR Protocols: A Guide to Methods and Applications*, 1990, Academic Press, San Diego, Calif. PCR primer pairs can be derived from a known sequence, for example, by using computer programs intended for that purpose such as the PCR primer analysis tool in Vector NTI version 6 (Informax Inc., Bethesd, Md.); PrimerSelect (DNASTAR Inc., Madison, Wis.); and Primer (Version 0.5.COPYRGT., 1991, Whitehead Institute for Biomedical Research, Cambridge, Mass.). Additionally, the sequence can be visually scanned and primers manually identified using guidelines known to one of skill in the art.

It is to be understood that as used herein the term "transgenic" includes any cell, cell line, callus, tissue, plant part, or plant, the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extrachromosomal) by conventional plant breeding methods or by naturally occurring events such as random cross-fertilization, non-recombinant viral infection, non-recombinant bacterial transformation, non-recombinant transposition, or spontaneous mutation.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al., *Meth. Enzymol.*, 1987, 143:277) and particle-accelerated or "gene gun" transformation technology (Klein et al., *Nature*, 1987, 327:70-73; U.S. Pat. No. 4,945,050, incorporated herein by reference). Additional transformation methods are disclosed below.

Thus, isolated polynucleotides can be incorporated into recombinant constructs, typically DNA constructs, which are capable of introduction into and replication in a host cell. Such a construct can be a vector that includes a replication system and sequences that are capable of transcription and translation of a polypeptide-encoding sequence in a given host cell. A number of vectors suitable for stable trans fection of plant cells or for the establishment of transgenic plants have been described in, e.g., Pouwels et al., *Cloning Vectors: A Laboratory Manual*, 1985; Supp. 1987; Weissbach & Weissbach, *Methods for Plant Molecular Biology*, 1989, Academic Press, New York, N.Y.; and Flevin et al., *Plant Molecular Biology Manual*, 1990, Kluwer Academic Publishers. Typically, plant expression vectors include, for example, one or more cloned plant genes under the transcriptional control of 5' and 3' regulatory sequences and a dominant selectable marker. Such plant expression vectors can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Various methods and compositions for identifying event SYHT0H2 are provided. Such methods find use in identifying and/or detecting event SYHT0H2 in any biological material. Such methods include, for example, methods to confirm seed purity and methods for screening seeds in a seed lot for event SYHT0H2. In one aspect of the invention, a method for identifying event SYHT0H2 in a biological sample is provided and comprises contacting the sample with a first and a second primer; and, amplifying a polynucleotide comprising a SYHT0H2 specific region.

A biological sample can comprise any sample in which one desires to determine if DNA having event SYHT0H2 is present. For example, a biological sample can comprise any plant material or material comprising or derived from a plant material such as, but not limited to, food or feed products. As used herein, "plant material" refers to material which is obtained or derived from a plant or plant part. In specific aspects of the invention, the biological sample comprises a soybean tissue.

Primers and probes based on the flanking DNA and insert sequences disclosed herein can be used to confirm (and, if necessary, to correct) the disclosed sequences by conventional methods, e.g., by re-cloning and sequencing such sequences. The polynucleotide probes and primers specifically detect a target DNA sequence. Any conventional nucleic acid hybridization or amplification method can be used to identify the presence of DNA from a transgenic event in a sample. By "specifically detect" it is intended that the polynucleotide can be used either as a primer to amplify a SYHT0H2 specific region or the polynucleotide can be used as a probe that hybridizes under stringent conditions to a polynucleotide having event SYHT0H2 or a SYHT0H2 specific region. The level or degree of hybridization which allows for the specific detection of event SYHT0H2 or a specific region of event SYHT0H2 is sufficient to distinguish the polynucleotide with the SYHT0H2 specific region from a polynucleotide lacking this region and thereby allow for discriminately identifying event SYHT0H2. By "shares sufficient sequence identity or complementarity to allow for the amplification of a SYHT0H2 specific event" is intended the sequence shares at least 80%, 85%, 90%, 91%, 92%, 93%, 94%, 95%, 96%, 97%, 98%, 99% or 100% identity or complementarity to a fragment or across the full length of the polynucleotide having the SYHT0H2 specific region.

Regarding the amplification of a target polynucleotide (e.g., by PCR) using a particular amplification primer pair, "stringent conditions" are conditions that permit the primer pair to hybridize to the target polynucleotide to which a primer having the corresponding wild type sequence (or its complement) would produce an identifiable amplification product (the amplicon) having a SYHT0H2 specific region in a DNA thermal amplification reaction. In a PCR approach, oligonucleotide primers can be designed for use in PCR reactions to amplify a SYHT0H2 specific region. Methods for designing PCR primers and PCR cloning are generally known in the art and are disclosed in Sambrook et al. (eds.), *Molecular Cloning: A Laboratory Manual*, 2$^{nd}$ ed., 1989, Cold Spring Harbor Laboratory Press, Plainview, N.Y.); Innis et al. (eds.), *PCR Protocols: A Guide to Methods and Applications,* 1990, Academic Press, New York; Innis & Gelfand (eds.), *PCR Strategies,* 1995, Academic Press, New York; and Innis & Gelfand (eds.), *PCR Methods Manual,* 1999, Academic Press, New York. Methods of amplification are further described in U.S. Pat. Nos. 4,683,195 and 4,683, 202 and Chen et al., *Proc. Natl. Acad. Sci. U.S.A.,* 1994, 91:5695-5699. These methods as well as other methods known in the art of DNA amplification may be used in the practice of the other aspects of the invention. It is understood that a number of parameters in a specific PCR protocol may need to be adjusted to specific laboratory conditions and may be slightly modified and yet allow for the collection of similar results. These adjustments will be apparent to a person skilled in the art.

The amplified polynucleotide (amplicon) can be of any length that allows for the detection of event SYHT0H2 or a SYHT0H2 specific region. For example, the amplicon can be about 10, 50, 100, 200, 300, 500, 700, 100, 2000, 3000, 4000, 5000 nucleotides in length or longer.

In specific aspects of the invention, a specific region of event SYHT0H2 is detected. Any primer that allows a SYHT0H2 specific region to be amplified and/or detected can be employed in the methods. For example, in specific aspects of the invention, the first primer comprises a fragment of a polynucleotide of SEQ ID NO: 10, wherein the first or the second primer shares sufficient sequence identity or complementarity to the polynucleotide to amplify the SYHT0H2 specific region. The primer pair can comprise a fragment of SEQ ID NO: 11 and a fragment of SEQ ID NO: 12. In still further aspects of the invention, the first and the second primer can comprise (a) any one or any combination of the sequences set forth in SEQ ID NOs: 11-12, 14-15, and 17-21; or (b) a sequence of a fragment of SEQ ID NO: 10 or the complement thereof. The primers can be of any length sufficient to amplify a SYHT0H2 region including, for example, at least 6, 7, 8, 9, 10, 15, 20, 15, or 30, or about 7-10, 10-15, 15-20, 20-25, 25-30, 30-35, 35-40, 40-45 nucleotides or longer. In some aspects of the invention the first and the second primer are SEQ ID NO: 11 and SEQ ID NO: 12, respectively; SEQ ID NO: 14 and SEQ ID NO: 15, respectively; SEQ ID NO: 17 and SEQ ID NO: 18, respectively; SEQ ID NO: 17 and SEQ ID NO: 19, respectively; SEQ ID NO: 17 and SEQ ID NO: 20, respectively; or SEQ ID NO: 17 and SEQ ID NO: 21, respectively. For example, useful primer pairs include (a) a first primer comprising the polynucleotide sequence of SEQ ID NO: 11 and a second primer comprising the polynucleotide sequence of SEQ ID NO: 12, which may be used to amplify a sequence spanning the LB1 (left border 1) junction of soybean genomic DNA and the inserted heterologous sequence containing the *Avena* HPPD sequence; (b) a first primer comprising the polynucleotide sequence of SEQ ID NO: 14 and a second primer comprising the polynucleotide sequence of SEQ ID NO: 15, which may be used to amplify a sequence spanning the LB2 (left border 2) junction of soybean genomic DNA and the inserted heterologous sequence containing the *Avena* HPPD sequence; (c) a first primer comprising the polynucleotide sequence of SEQ ID NO: 17 and a second primer comprising the polynucleotide sequence of SEQ ID NO: 18 or SEQ ID NO: 19, which may be used to amplify a sequence spanning the LB1 junction of soybean genomic DNA and the inserted heterologous sequence containing the *Avena* HPPD sequence; and (d) a first primer comprising the polynucleotide sequence of SEQ ID NO: 17 and a second primer comprising the polynucleotide sequence of SEQ ID NO: 20 or SEQ ID NO: 21, which may be used to amplify the LB 1 junction of soybean genomic DNA and the inserted heterologous sequence containing the *Avena* HPPD sequence.

As discussed elsewhere herein, any method to PCR amplify event SYHT0H2 or specific region can be employed, including for example, real time PCR. See, e.g., Livak et al., *PCR Methods and Applications,* 1995, 4:357-362; U.S. Pat. Nos. 5,538,848 and 5,723,591; Applied Biosystems User Bulletin No. 2, "Relative Quantitation of Gene Expression," U.S. Pat. No. 4,303,859; and Applied Biosystems User Bulletin No. 5, "Multiplex PCR with TAQMAN® VIC probes," U.S. Pat. No. 4,306,236; each of which is herein incorporated by reference.

Thus, in specific aspects of the invention, a method of detecting the presence of soybean event SYHT0H2 or progeny thereof in a biological sample is provided. The method comprises (a) extracting a DNA sample from the biological sample; (b) providing a pair of DNA primer molecules (e.g., any combination of SEQ ID NOs: 11-12, 14-15, and 17-21 and/or useful fragments of SEQ ID NO: 10 or the complement thereof, wherein the combination amplifies a event SYHT0H2 specific region), including, but not limited to (i) primers comprising the sequences of SEQ ID NO: 11 and SEQ ID NO: 12, (ii) primers comprising the sequences of SEQ ID NO: 14 and SEQ ID NO: 15, (iii) primers comprising the sequences of SEQ ID NO: 17 and SEQ ID NO: 18, (iv) primers comprising the sequences of SEQ ID NO: 17 and SEQ ID NO: 19; (v) primers comprising the sequences of SEQ ID NO: 17 and SEQ ID NO: 20; and (vi) primers comprising the sequences of SEQ ID NO: 17 and SEQ ID NO: 21; (c) providing DNA amplification reaction conditions; (d) performing the DNA amplification reaction, thereby producing a DNA amplicon molecule; and (e) detecting the DNA amplicon molecule, wherein the detection of the DNA amplicon molecule in the DNA amplification reaction indicates the presence of soybean event SYHT0H2. In order for a nucleic acid molecule to serve as a primer or probe it needs only be sufficiently complementary in sequence to be able to form a stable double-stranded structure under the particular solvent and salt concentrations employed.

In hybridization techniques, all or part of a polynucleotide that selectively hybridizes to a target polynucleotide having a SYHT0H2 specific event is employed. By "stringent conditions" or "stringent hybridization conditions" when referring to a polynucleotide probe conditions under which a probe will hybridize to its target sequence to a detectably greater degree than to other sequences (e.g., at least 2-fold over background) are intended. Regarding the amplification of a target polynucleotide (e.g., by PCR) using a particular amplification primer pair, "stringent conditions" are conditions that permit the primer pair to hybridize to the target polynucleotide to which a primer having the corresponding wild type. Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of identity are detected (heterologous probing). Generally, a probe is less than about 1000 nucleotides in length or less than 500 nucleotides in length.

As used herein, a substantially identical or complementary sequence is a polynucleotide that will specifically hybridize to the complement of the nucleic acid molecule to which it is being compared under high stringency conditions. Appropriate stringency conditions which promote DNA hybridization, for example, 6× sodium chloride/sodium citrate (SSC) at about 45° C., followed by a wash of 2×SSC at 50° C., are known to those skilled in the art or can be found in Ausebel et al. (eds.), *Current Protocols in Molecular Biology*, 1989, John Wiley & Sons, NY, 6.3.1-6.3.6. Typically, stringent conditions for hybridization and detection will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in IX to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to IX SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In hybridization reactions, specificity is typically the function of post-hybridization washes, the critical factors being the ionic strength and temperature of the final wash solution. For DNA-DNA hybrids, the Tm can be approximated from the equation of Meinkoth & Wahl, *Anal. Biochem.*, 1984, 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is optimal to increase the SSC concentration so that a higher temperature can be used. An extensive guide to the hybridization of nucleic acids is found in Tijssen, *Laboratory Techniques in Biochemistry and Molecular Biology*, 1993, Part I, Chapter 2, Elsevier, NY; Ausubel et al. (eds.), *Current Protocols in Molecular Biology*, 1995, Chapter 2, Greene Publishing and Wiley-Interscience, NY; Sambrook et al. (eds.), *Molecular Cloning: A Laboratory Manual*, 2$^{nd}$ ed., 1989, Cold Spring Harbor Laboratory Press, Plainview, N.Y.) and Haymes et al., In: *Nucleic Acid Hybridization, a Practical Approach*, 1985, IRL Press, Washington, D.C.

A polynucleotide is said to be the "complement" of another polynucleotide if they exhibit complementarity. As used herein, molecules are said to exhibit "complete complementarity" when every nucleotide of one of the polynucleotide molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions.

Further provided are methods of detecting the presence of DNA corresponding to event SYHT0H2 in a sample. In one aspect of the invention, the method comprises (a) contacting the biological sample with a polynucleotide probe that hybridizes under stringent hybridization conditions with DNA from soybean event SYHT0H2 and specifically detects event SYHT0H2; (b) subjecting the sample and probe to stringent hybridization conditions; and (c) detecting hybridization of the probe to the DNA, wherein detection of hybridization indicates the presence of event SYHT0H2. In one aspect of the invention, the DNA is digested with appropriate enzymes are preformed prior to the hybridization event.

Various methods can be used to detect the SYHT0H2 specific region or amplicon thereof, including, but not limited to, Genetic Bit Analysis (Nikiforov et al., *Nucleic Acid Res.,* 1994, 22: 4167-4175). In one method, a DNA oligonucleotide is designed which overlaps both the adjacent flanking DNA sequence and the inserted DNA sequence. In other aspects of the invention, DNA oligos are designed to allow for a SYHT0H2 specific amplicon. The oligonucleotide is immobilized in wells of a microwell plate. Following PCR of the region of interest a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another detection method is the Pyrosequencing technique as described by Winge, *Innov. Pharma. Tech.,* 2000, 00:18-24). In this method, an oligonucleotide is designed that overlaps the adjacent DNA and insert DNA junction or a pair of oligos are employed that can amplify a SYHT0H2 specific region. The oligonucleotide is hybridized to a single-stranded PCR product from the region of interest (one primer in the inserted sequence and one in the flanking sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization as described by Chen et al., *Genome Res.,* 1999, 9: 492-498) is a method that can be used to detect an amplicon of the invention. Using this method, an oligonucleotide is designed which overlaps the flanking and inserted DNA junction or a pair of oligos are employed that can amplify a SYHT0H2 specific region. The oligonucleotide is hybridized to a single-stranded PCR product from the region of interest (one primer in the inserted DNA and one in the flanking DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the flanking and insert DNA junction or a pair of oligos are employed that can amplify a SYHT0H2 specific region. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi et al., *Nature Biotech.,* 1996, 14: 303-308). Briefly, a FRET oligonucleotide probe is designed that overlaps the flanking and insert DNA junction, or a pair of oligos are employed that can amplify a SYHT0H2 specific region. The unique structure of the FRET probe results in it containing secondary structure that keeps the fluorescent and quenching moieties in close proximity. The FRET probe and PCR primers (one primer in the insert DNA sequence and one in the flanking sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/trans gene insert sequence due to successful amplification and hybridization.

A hybridization reaction using a probe specific to a sequence found within the amplicon is yet another method used to detect the amplicon produced by a PCR reaction.

As used herein, "kit" refers to a set of reagents for the purpose of performing the method aspects of the invention, more particularly, the identification and/or the detection of event SYHT0H2 in biological samples. The kit can be used, and its components can be specifically adjusted, for purposes of quality control (e.g. purity of seed lots), detection of event SYHT0H2 in plant material, or material comprising or derived from plant material, such as but not limited to food or feed products.

In specific aspects of the invention, a kit for identifying event SYHT0H2 in a biological sample is provided. The kit comprises a first and a second primer, wherein the first and second primer amplify a polynucleotide comprising a SYHT0H2 specific region. In further aspects of the invention, the kit comprises a polynucleotide for the detection of the SYHT0H2 specific region. The kit can comprise, for example, a first primer comprising a fragment of a polynucleotide of SEQ ID NO: 10 or the complement thereof, wherein the first or the second primer shares sufficient sequence homology or complementarity to the polynucleotide to amplify a SYHT0H2 specific region. For example, the primer pair can comprise a fragment of SEQ ID NO: 11 and a fragment of SEQ ID NO: 12 or the complement thereof. In still further aspects of the invention, the first and the second primer can comprise any one or any combination of the sequences set forth in SEQ ID NOs: 11-12, 14-15, and 17-21. The primers can be of any length sufficient to amplify a SYHT0H2 region including, for example, at least 6, 7, 8, 9, 10, 15, 20, 15, or 30 or about 7-10, 10-15, 15-20, 20-25, 25-30, 30-35, 35-40, 40-45 nucleotides or longer. In some aspects of the invention the first and the second primer are SEQ ID NO: 11 and SEQ ID NO: 12, respectively; SEQ ID NO: 14 and SEQ ID NO: 15, respectively; SEQ ID NO: 17 and SEQ ID NO: 18, respectively; or SEQ ID NO: 17 and SEQ ID NO: 19, respectively; or SEQ ID NO: 17 and SEQ ID NO: 20, respectively; or SEQ ID NO: 17 and SEQ ID NO: 21, respectively. For example, the above-noted primer pairs can be used to amplify (a) a sequence spanning the LB1 junction of soybean genomic DNA and the heterologous insert containing the *Avena* HPPD sequence (SEQ ID NOs: 11 and 12; SEQ ID NOs: 17 and 18; SEQ ID NOs: 17 and 19); or (b) a sequence spanning the LB2 junction of soybean genomic DNA and the heterologous insert containing the *Avena* HPPD sequence (SEQ ID NOs: 14 and 15; SEQ ID NOs: 17 and 20; SEQ ID NOs: 17 and 21).

Further provided are DNA detection kits comprising at least one polynucleotide that can specifically detect a SYHT0H2 specific region, wherein the polynucleotide comprises at least one DNA molecule of a sufficient length of contiguous nucleotides homologous or complementary to SEQ ID NO: 10. In specific aspects of the invention, the DNA detection kit comprises a polynucleotide of any one of SEQ ID NOs: 11-12, or fragment thereof, or a sequence which hybridizes to any one of SEQ ID NOs: 11-12, or fragment thereof.

Any of the polynucleotides and fragments and variants thereof employed in the methods and compositions can share sequence identity to a region of the transgene insert of event SYHT0H2, a junction sequence of event SYHT0H2 or a flanking sequence of event SYHT0H2. Methods to determine the relationship of various sequences are known. As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence. As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers & Miller, *CABIOS*, 1988, 4:11-17; the local alignment algorithm of Smith et al., *Adv. Appl. Math.*, 1981, 2:482; the global alignment algorithm of Needleman & Wunsch, *J. Mol. Biol.*, 1970, 48:443-453; the search-for-local alignment method of Pearson & Lipman, *Proc. Natl. Acad. Sci. U.S.A.*, 1988, 85:2444-2448; the algorithm of Karlin & Altschul, *Proc. Natl. Acad. Sci. U.S.A.*, 1990, 87:2264, modified as in Karlin & Altschul, *Proc. Natl. Acad. Sci. U.S.A.*, 1993, 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif.). Alignments using these programs can be performed using the default parameters. The CLUSTAL program is well described by Higgins et al., *Gene*, 1988, 73:237-244; Higgins et al., *C45/OS*, 1989, 5:151-153; Corpet et al., *Nucleic Acids Res.*, 1988, 16:10881-90; Huang et al., *CABIOS*, 1992, 8:155-65; and Pearson et al., *Meth. Mol. Biol.*, 1994, 24:307-331. The ALIGN program is based on the algorithm of Myers & Miller, *CABIOS*, 1988, 4:11-17. A PAM120 weight residue table, a gap length penalty of 12, and a gap penalty of 4 can be used with the ALIGN program when comparing amino acid sequences. The BLAST programs of Altschul et al., *J. Mol. Biol.*, 1990, 215:403 are based on the algorithm of Karlin & Altschul, *Proc. Natl. Acad. Sci. U.S.A.*, 1993, 90:5873-5877. BLAST nucleotide searches can be performed with the BLASTN program, score=100, wordlength=12, to obtain nucleotide sequences homologous to a nucleotide sequence encoding a protein. BLAST protein searches can be performed with the BLASTX program, score=50, wordlength=3, to obtain amino acid sequences homologous to a protein or polypeptide. To obtain gapped alignments for comparison purposes, Gapped BLAST (in BLAST 2.0) can be utilized as described in Altschul et al., *Nucleic Acids Res.*, 1997, 25:3389. Alternatively, PSI-BLAST (in BLAST 2.0) can be used to perform an iterated search that detects distant relationships between molecules. See Altschul et al., *Nucleic Acids Res.*, 1997, 25:3389. When utilizing BLAST, Gapped BLAST, PSI-BLAST, the default parameters of the respective programs (e.g., BLASTN for nucleotide sequences, BLASTX for proteins) can be used. Alignment may be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" any sequence comparison program that, for any two sequences in question, generates an alignment having identical nucleotide or amino acid residue matches and an identical percent sequence identity when compared to the corresponding alignment generated by GAP Version 10 is intended.

GAP uses the algorithm of Needleman & Wunsch, *J. Mol. Biol.*, 1970, 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65, or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the Quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff & Henikoff, *Proc. Natl. Acad. Sci. U.S.A.*, 1989, 89:10915).

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The present invention further provides a method of selectively controlling weeds at a location (i.e. an area of cultivation) comprising crop plants and weeds, wherein the crop plants comprise SYHT0H2, wherein the method comprises application to the location of a weed controlling amount of a herbicidal composition comprising one or more HPPD inhibiting herbicides.

The term "controlling," and derivations thereof, for example, as in "controlling weeds" refers to one or more of inhibiting the growth, germination, reproduction, and/or proliferation of; and/or killing, removing, destroying, or otherwise diminishing the occurrence and/or activity of a weed.

As used herein, an "area of cultivation" or "location" comprises any region in which one desires to grow a plant. Such areas of cultivations include, but are not limited to, a field in which a plant is cultivated (such as a crop field, a sod field, a tree field, a managed forest, a field for culturing fruits and vegetables, etc.), a greenhouse, a growth chamber, etc.

The methods comprise planting the area of cultivation with the soybean SYHT0H2 seeds or plants, and in specific aspects of the invention, applying to the crop, seed, weed or area of cultivation thereof a weed controlling amount of an herbicide of interest. It is recognized that the herbicide can be applied before or after the crop is planted in the area of cultivation. Such herbicide applications can include an application of an HPPD inhibitor, either alone or in combination with other herbicides that are tolerated by the crop. The skilled person will appreciate that the weed controlling amount will vary, for example, depending on the type and timing of application of the herbicide(s)—but equates to an amount which provides desirable levels of weed control whilst causing little, if any, damage to the crop. For an HPPD inhibiting herbicide, the amount will be typically between 15 to 500 gai/ha.

In another aspect of the invention, the herbicidal composition comprises at least two HPPD inhibitors. The HPPD inhibitors can be applied at any effective rate that selectively controls weeds and does not significantly damage the crop.

In a particular aspect of the invention, the HPPD inhibitor is selected from the group comprising of benzobicyclon, bicyclopyrone, mesotrione, sulcotrione, tefuryltrione, tembotrione, ketospiradox or the free acid thereof, benzofenap, pyrasulfotole, pyrazolynate, pyrazoxyfen, topramezone, [2-chloro-3-(2-methoxyethoxy)-4-(methylsulfonyl)phenyl] (1-ethyl-5-hydroxy-1H-pyrazol-4-yl)-methanone, (2,3-dihydro-3,3,4-trimethyl-1,1-dioxidobenzo[b]thien-5-yl)(5-hydroxy-1-methyl-1H-pyrazol-4-yl)-methanone, isoxachlortole, isoxaflutole, α-(cyclopropylcarbonyl)-2-(methylsulfonyl)-β-oxo-4-chloro-benzenepropanenitrile, and α-(cyclopropylcarbonyl)-2-(methylsulfonyl)-β-oxo-4-(trifluoromethyl)-benzenepropanenitrile or an agriculturally acceptable salt thereof. In a particularly preferred embodiment the HPPD inhibitor is mesotrione. In a particularly preferred embodiment the HPPD inhibitor is tembotrione. In a particularly preferred embodiment the HPPD inhibitor is bicyclopyrone. In a particularly preferred embodiment the HPPD inhibitor is isoxaflutole. In a particularly preferred embodiment the HPPD inhibitor is pyrasulfatole. In a particularly preferred embodiment the HPPD inhibitor is topramezone.

Soybean plants comprising event SYHT0H2 may further comprise one or more additional polynucleotide region(s) which encode polypeptide(s) which impart tolerance to one or more additional herbicides, insects, fungal, bacterial and/or viral infections. Examples of polypeptide(s) which impart tolerance to herbicides include, for example, glyphosate tolerant 5-enol-pyruvylshikimate-3-phosphate synthase (EPSPS) (for example as disclosed in U.S. Pat. Nos. 5,804,425 and 6,566,587), glyphosate N-acetyl transferase (GAT) (for example as disclosed in WO02/036782), herbicide tolerant 4-hydroxypyruvyldioxygenase (HPPD) (for example as disclosed in WO02/46387), phosphinothricin acetyl transferase (PAT) (for example as disclosed in U.S. Pat. No. 5,273,894), cytochrome P450 (for example as disclosed in PCT International Publication No. WO 07/103,567), glutathione S-transferase (GST) (for example as disclosed in PCT International Publication No. WO 01/21770), herbicide tolerant acetyl-COA-carboxylase (ACCase), herbicide tolerant acetolactate synthase (ALS) (for example as disclosed in U.S. Pat. No. 5,013,659), herbicide tolerant protoporphyrinogen oxidase (PPGO) (for example as disclosed in PCT International Publication No. WO 95/34659), bromoxynil nitrilase (for example, as disclosed in PCT International Publication No. WO 89/00193), herbicide tolerant phytoene desaturase (for example as disclosed in European Published Application No. 0393690), aryloxyalkanoate dioxygenase (for example as disclosed in PCT International Publication Nos. WO 2005/107437 and WO 2007/053482) and dicamba degrading enzymes (for example as disclosed in PCT International Publication No. WO 98/45424); including known mutagenised or otherwise modified variants of these polypeptides.

Accordingly, an herbicidal composition applied to the location may further comprise one or more additional pesticides, that the soybean plant comprising the event SYTH0H2 is tolerant to, for example a nematicide, an insecticide, a fungicide and/or an herbicide. Examples of suitable pesticides are listed in Tomlin, C.D.S. (ed.), *The Pesticide Manual*, 14$^{th}$ ed., 2006.

For example the pesticide may be one or more pesticides selected from the following classes of insecticidally, acaricidally, nematicidally, or molluscicidally active ingredients: Alanycarb, Aldicarb, Bendiocarb, Benfuracarb, Butocarboxim, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiodicarb, Thiofanox, Triazamate, Trimethacarb, XMC, Xylylcarb; Acephate, Azamethiphos, Azinphos-ethyl, Azinphos-methyl, Cadusafos, Chlorethoxyfos, Chlorfenvinphos, Chlormephos, Chlorpyrifos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fosthiazate, Heptenophos, Imicyafos, Isofenphos, Isopropyl O-(methoxyaminothio-phosphoryl) salicylate, Isoxathion, Malathion, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-methyl, Profenofos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Triclorfon, Vamidothion, cyclodiene organochlorines, Chlordane, Endosulfan; Ethiprole, Fipronil, Acrinathrin, Allethrin, d-cis-trans Allethrin, d-trans Allethrin, Bifenthrin, Bioallethrin, Bioallethrin S-cyclopentenyl isomer, Bioresmethrin, Cycloprothrin, Cyfluthrin, beta-Cyfluthrin, Cyhalothrin, lambda-Cyhalothrin, gamma-Cyhalothrin, Cypermethrin, alpha-Cypermethrin, beta-Cypermethrin, theta-Cypermethrin, zeta-Cypermethrin, Cyphenothrin [(1R)-trans isomers], Deltamethrin, Empenthrin [(EZ)-(1R) isomers), Esfenvalerate, Etofenprox, Fenpropathrin, Fenvalerate, Flucythrinate, Flumethrin, tau-Fluvalinate, Halfenprox, Imiprothrin, Kadethrin, Permethrin, Phenothrin [(1R)-trans isomer), Prallethrin, Pyrethrine (pyrethrum), Resmethrin, Silafluofen, Tefluthrin, Tetramethrin, Tetramethrin [(1R) isomers)], Tralomethrin, Transfluthrin; DDT; Methoxychlor, Acetamiprid, Clothianidin, Dinotefuran, Imidacloprid, Nitenpyram, Thiacloprid, Thiamethoxam; Nicotine, Spinetoram, Spinosad, Abamectin, Emamectin benzoate, Lepimectin, Milbemectin, Hydroprene, Kinoprene, Methoprene; Fenoxycarb; Pyriproxyfen, Chloropicrin; Sulfuryl fluoride; Borax; Tartar emetic, Pymetrozine; Flonic amid, Clofentezine, Hexythiazox, Diflovidazin, Etoxazole. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, BT crop proteins: Cry1Ab, Cry1Ac, Cry1Fa, Cry2Ab, mCry3A, Cry3Ab, Cry3Bb, Cry34/35Ab1, Diafenthiuron, Azocyclotin, Cyhexatin, Fenbutatin oxide; Propargite, Tetradifon, Chlorfenapyr, DNOC, Sulfluramid, Bensultap, Cartap hydrochloride, Thiocyclam, Thiosultap-sodium, Bistrifluoron, Chlorfluazuron, Diflubenzuron, Flucycloxuron, Flufenoxuron, Hexaflumuron, Lufenuron, Novaluron, Noviflumuron, Teflubenzuron, Triflumuron, Buprofezin, Cyromazine, Chromafenozide, Halofenozide, Methoxyfenozide, Tebufenozide, Amitraz, Hydramethylnon; Acequinocyl; Fluacrypyrim, Fenazaquin, Fenpyroximate, Pyrimidifen, Pyridaben, Tebufenpyrad, Tolfenpyrad, Rotenone (Derris), Indoxacarb; Metaflumizone, Spirodiclofen, Spiromesifen, Spirotetramat, Aluminium phosphide, Calcium phosphide, Phosphine, Zinc phosphide, Cyenopyrafen, Chlorantraniliprole, Flubendiamide, Amidoflumet, Azadirachtin, Benclothiaz, Benzoximate, Bifenazate, Bromopropylate, Chinomethionat, Cryolite, Cyantraniliprole (Cyazypyr), Cyflumetofen, Dicofol, Diflovidazin, Fluensulfone, Flufenerim, Flufiprole, Fluopyram, Fufenozide, Imidaclothiz, Iprodione, Meperfluthrin, Pyridalyl, Pyrifluquinazon, Tetramethylfluthrin, Iodomethane; products based on *Bacillus firmus* (including but not limited to strain CNCM 1-1582, such as, for example, VOTiVO™, BioNem); 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934), 4-{[(6-bromopyridin-3-yl)methyl](2-fluoroethyl)amino}furan-2(5H)-one (known from WO2007/115644), 4-{[(6-fluoropyridin-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chlorpyridin-3-yl)methyl](2-fluoroethyl)amino}furan-2(5H)-one (known from WO2007/115644), Flupyradifurone, 4-{[(6-chlor-5-fluoropyridin-3-yl)methyl](methyl)amino}furan-2(5H)-one (known from WO2007/115643), 4-{[(5,6-dichloropyridin-3-yl)methyl](2-fluoroethyl)amino}furan-2(5H)-one (known from WO2007/115646), 4-{[(6-chloro-5-fluoropyridin-3-yl)methyl]-(cyclopropyl)-amino}-furan-2(5H)-one (known from WO2007/115643), 4-{[(6-chloropyridin-3-yl)methyl]-(cyclopropyl)-amino}furan-2(5H)-one (known from EP-A-0 539 588), 4-{[(6-chloropyridin-3-yl)-methyl](methyl)amino}furan-2(5H)-one (known from EP-A-0 539 588), {[1-(6-chloropyridin-3-yl)ethyl](methyl)oxido-$\lambda^4$-sulfanylidene}cyanamide (known from WO2007/149134) and its diastereomers {[(1R)-1-(6-chloropyridin-3-yl)ethyl](methyl)oxido-$\lambda^4$-sulfanylidene}cyanamide (A) and {[(1S)-1-(6-chloropyridin-3-yl)ethyl](methyl)oxido-$\lambda^4$-sulfanylidene}cyanamide (B) (also known from WO2007/149134) as well as Sulfoxaflor and its diastereomers [(R)-methyl(oxido){(1R)-1-[6-(trifluoromethyl)pyridin-3-yl]ethyl}-$\lambda^4$-sulfanylidene]cyanamide (A1) and [(S)-methyl (oxido){(1S)-1-[6-(trifluoromethyl)pyridin-3-yl]ethyl}-$\lambda^4$-sulfanylidene]-cyanamide (A2), referred to as group of diastereomers A (known from WO2010/074747, WO2010/074751), [(R)-methyl(oxido){(1S)-1-[6-(trifluoromethyl)pyridin-3-yl]ethyl}-$\lambda^4$-sulfanylidene]cyanamide (B1) and [(S)-methyl(oxido){(1R)-1-[6-(trifluoromethyl)pyridin-3-yl]ethyl}-$\lambda^4$-sulfanylidene]cyanamide (B2), referred to as group of diastereomers B (also known from WO2010/074747, WO2010/074751), and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluorethyl) sulfinyl]phenyl}-3-(trifluoromethyl)-1H-1,2,4-triazol-5-amine (known from WO2006/043635), [(3S,4aR,12R,12aS, 12bS)-3-[(cyclopropylcarbonyl)oxy]-6,12-dihydroxy-4, 12b-dimethyl-11-oxo-9-(pyridin-3-yl)-1,3,4,4a,5,6, 6a,12,12a,12b-decahydro-2H,11H-benzo[f]-pyrano[4,3-b]chromen-4-yl]methyl cyclopropanecarboxylate (known from WO2008/066153), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethylbenzenesulfonamide (known from WO2005/035486), 4-(difluoromethoxy)-N-ethyl-N-methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazol-2-amine (known from WO2008/104503), {1'-[(2E)-3-(4-chlorophenyl)prop-2-en-1-yl]-5-fluorospiro[indole-3,4'-piperidin]-1 (2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diaza-spiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)-pyridazin-3-yl]-3-azabicyclo[3.2.1]octane (known from WO2007/040280), Flometoquin, PF1364 (CAS-Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]-ethyl}benzamide (known from WO2005/085216), 4-{[(6-chloropyridin-3-yl)methyl]-(cyclopropyl)amino}-1,3-oxazol-2(5H)-one, 4-{[(6-chloropyridin-3-yl)methyl](2,2-difluoroethyl)-amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO2010/005692), NNI-0711 (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl2-[2-({[3-bromo-1-(3-chloropyridin-2-yl)-1H-pyrazol-5-yl]carbonyl}-amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)-benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl]carbonyl}-amino)benzoyl]-2-ethylhydrazine-carboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), N-[2-(5-amino-1,3,4-thiadiazol-2-yl)-4-chloro-6-methylphenyl]-3-bromo-1-(3-chloro-pyridin-2-yl)-1H-pyrazole-5-carboxamide (known from CN102057925), and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO2011/049233).

For further example, the fungicide includes, but is not limited to, one or more fungicides selected from the following aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide, O-[1-(4-methoxyphenoxy)-3,3-dimethylbutan-2-yl]1H-imidazole-1-carbothioate, bixafen, boscalid, carboxin, diflumetorim, fenfuram, fluopyram, flutolanil, fluxapyroxad, furametpyr, furmecyclox, isopyrazam (mixture of syn-epimeric racemate 1RS,4SR,9RS and anti-epimeric racemate 1RS,4SR,9SR), isopyrazam (anti-epimeric racemate 1RS,4SR,9SR), isopyrazam (anti-epimeric enantiomer 1R,4S,9S), isopyrazam (anti-epimeric enantiomer 1S,4R,9R), isopyrazam (syn epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl]quinazolin-4-amine, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, ametoctradin, amisulbrom, azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)

phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulfanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide, (2R)-2-{2-[(2,5-dimethylphenoxy)methyl]phenyl}-2-methoxy-N-methylacetamide, benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine, 3-chloro-5-(6-chloropyridin-3-yl)-6-methyl-4-(2,4,6-trifluorophenyl)pyridazine, bordeaux mixture, captafol, captan, chlorothalonil, copper hydroxide, copper naphthenate, copper oxide, copper oxychloride, copper(2+) sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur, sulphur preparations including calcium polysulphide, thiram, tolylfluanid, zineb, ziram, acibenzolar-5-methyl, isotianil, probenazole, tiadinil, andoprim, blasticidin-S, cyprodinil, kasugamycin, kasugamycin hydrochloride hydrate, mepanipyrim, pyrimethanil, 3-(5-fluoro-3,3,4,4-tetramethyl-3,4-dihydroisoquinolin-1-yl)quinoline, fentin acetate, fentin chloride, fentin hydroxide, silthiofam, benthiavalicarb, dimethomorph, flumorph, iprovalicarb, mandipropamid, polyoxins, polyoxorim, valifenalate, valifenalate, biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene tolclofos-methyl, carpropamid, diclocymet, fenoxanil, phthalide, pyroquilon, tricyclazole, 2,2,2-trifluoroethyl {3-methyl-1-[(4-methylbenzoyl)amino]butan-2-yl}carbamate, benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl, oxolinic acid, chlozolinate, fenpiclonil, fludioxonil, iprodione, procymidone, quinoxyfen, vinclozolil, binapacryl, dinocap, ferimzone, fluazinam, meptyldinocap, benthiazole, bethoxazin, capsimycin, carvone, chinomethionat, pyriofenone (chlazafenone), cufraneb, cyflufenamid, cymoxanil, cyprosulfamide, dazomet, debacarb, dichlorophen, diclomezine, difenzoquat, difenzoquat methylsulphate, diphenylamine, ecomate, fenpyrazamine, flumetover, fluoroimide, flusulfamide, flutianil, fosetyl-aluminium, fosetyl-calcium, fosetyl-sodium, hexachlorobenzene, irumamycin, methasulfocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and salts, phenothrin, phosphorous acid and its salts, propamocarb-fosetylate, propanosine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl)prop-2-en-1-one, pyrrolnitrine, tebufloquin, tecloftalam, tolnifanide, triazoxide, trichlamide, zarilamid, (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl)pyridine, 2,3-dibutyl-6-chlorothieno[2,3-d]pyrimidin-4(3H)-one, 2,6-dimethyl-1H,5H-[1,4]dithiino[2,3-c:5,6-c']dipyrrole-1,3,5,7(2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulfonohydrazide, 5-fluoro-2-[(4-fluorobenzyl)oxy]pyrimidin-4-amine, 5-fluoro-2-[(4-methylbenzyl)oxy]pyrimidin-4-amine, 5-methyl-6-octyl[1,2,4]triazolo[1,5-a]pyrimidin-7-amine, ethyl (2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloro-pyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]-methyl}-2-phenylacetamide, N-{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1- methyl-1H-tetrazol-5-yl)(phenyl)methylidene]amino}oxy)methyl]pyridin-2-yl}carbamate, phenazine-1-carboxylic acid, quinolin-8-ol, quinolin-8-ol sulfate (2:1), tert-butyl {6-[({[(1-methyl-1H-tetrazol-5-yl)(phenyl)methylene]amino}oxy)methyl]pyridin-2-yl}carbamate, 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone, N-[2-(4-{[3-(4-chlorophenyl)prop-2-yn-1-yl]oxy}-3-methoxyphenyl)ethyl]-N2-(methylsulfonyl)valinamide, 4-oxo-4-[(2-phenylethyl)amino]butanoic acid, but-3-yn-1-yl {6-[({[(Z)-(1-methyl-1H-tetrazol-5-yl)(phenyl)-methylene]amino}oxy)methyl]pyridin-2-yl}carbamate.

For further example, the additional pesticide may be one or more herbicides selected from the group consisting of: acetochlor, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminocyclopyrachlor-potas sium, aminocyclopyrachlor-methyl, aminopyralid, amitrole, ammonium-sulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clethodim, clodinafop, clodinafop-propargyl, clomazone, clomeprop, clopyralid, cloransulam, cloransulam-methyl, cumyluron, cyanamide, cyanazine, cycloate, cyclosulfamuron, cycloxydim, cyhalofop, cyhalofop-butyl, cyprazine, 2,4-D, 2,4-D-butotyl, -butyl, -dimethylammonium, -diolamin, -ethyl, 2-ethylhexyl, dazomet, -isobutyl, -isooctyl, -isopropylammonium, -potassium, -triisopropanolammonium and -trolamine, 2,4-DB, 2,4-DB-butyl, -dimethylammonium, isooctyl, -potassium and -sodium, daimuron (dymron), dalapon, n-decanol, desmedipham, detosyl-pyrazolate (DTP), dicamba, dichlobenil, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromid, dithiopyr, diuron, DNOC, endothal, EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, F-5231, i.e. N-{2-chloro-4-fluoro-5-[4-(3-fluoroprop yl)-5-oxo-4,5-dihydro-1H-tetrazol-1-yl]phenyl}ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet (thiafluamide), flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyrsulfuron, flupyrsulfuron-methyl-sodium, fluridone, fluorochloridone, fluoroxypyr, fluoroxypyr-meptyl, flurtamone, fluthiacet, fluthiacet-methyl, fluthiamide, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium and -trimesium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl-(2,4-dichlorophenoxy)acetate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, kenacil, kinuron, MCPA, MCPA-butotyl, -dimethylammonium, -2-ethylhexyl, -isopropylammonium, -potassium and -sodium, MCPB, MCPB-methyl, -ethyl and -sodium, mecoprop, mecoprop-sodium, and -butotyl, mecoprop-P, mecoprop-P-butotyl, dimethylammonium, -2-ethylhexyl and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinat, monolinuron, monosulfuron, monosulfuron-ester, MT-128, i.e. 6-chloro-N-[(2E)-3-chloroprop-2-en-1-yl]-5-methyl-N-phenylpyridazin-3-amine, MT-5950, i.e. N-(3-chloro-4-isopropylphenyl)-2-methylpentan amide, NGGC-011, napropamide, NC-310, i.e. [5-(benzyloxy)-1-methyl-1H-pyrazol-4-yl](2,4-dichlorophenyl)methanone, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat dichloride, pebulate, pendimethalin, penoxsulam, pentachlorphenol, pentoxazone, pethoxamid, petroleum oils, phenmedipham, picloram, picolinafen, pinoxaden, piperophos, pretilachlor, primisulfuron, primisulfuron-methyl, prodiamine, prifluraline, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, sulcotrion, sulfentrazone, sulfometuron, sulfometuron-methyl, sulfosulfuron, SW-065, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trichloroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thiencarbazone, thiencarbazone-methyl, thifensulfuron, thifensulfuron-methyl, thiobencarb, topramezone, tralkoxydim, triafamone, tri-allate, triasulfuron, triaziflam, tribenuron, tribenuron-methyl, triclopyr, trietazine, trifloxysulfuron, trifloxysulfuron-sodium, trifluralin, triflusulfuron, triflusulfuron-methyl, tritosulfuron, urea sulfate, vernolate, ZJ-0862, i.e. 3,4-dichloro-N-{2-[(4,6-dimethoxypyrimidin-2-yl)oxy]benzyl}aniline; or plant growth regulators selected from the group consisting of zcibenzolar, acibenzolar-S-methyl, 5-aminolevulinic acid, ancymidol, 6-benzylaminopurine, Bras sinolid, catechine, chlormequat chloride, cloprop, cyclanilide, 3-(cycloprop-1-enyl) propi-onic acid, daminozide, dazomet, n-decanol, dikegulac, dikegulac-sodium, endothal, endothal-dipotassium, -disodium, and mono(N,N-dimethylalkylammonium), ethephon, flumetralin, flurenol, flurenol-butyl, flurprimidol, forchlorfenuron, gibberellic acid, inabenfide, indol-3-acetic acid (IAA), 4-indol-3-ylbutyric acid, isoprothiolane, probenazole, jasmonic acid, maleic hydrazide, mepiquat chloride, 1-methylcyclopropene, methyl jasmonate, 2-(1-naphthyl)acetamide, 1-naphthylacetic acid, 2-naphthyloxy-acetic acid, nitrophenolate-mixture, paclobutrazol, N-(2-phenylethyl)-beta-alanine, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P; or agrochemically preferable salts or other forms thereof.

In a preferred embodiment of the present invention the herbicidal composition applied to the location further comprises glyphosate and/or glufosinate.

Thus, depending on the nature of the herbicides in the herbicidal composition said composition can be applied to the location pre-planting, pre-emergence and/or post emergence. By "pre-planting" it is meant that the herbicide composition is applied before the crop is planted at the location, by "pre-emergence" it is meant that the herbicide composition is applied before the germinating crop plant seed emerges above the location surface and by "post-emergence" it is meant that the herbicide composition is applied once the crop plant is visible above the location surface. These individual use patterns can be applied to the location alone or in any combination. For example, the use pattern could comprise a pre-planting application followed by a post emergence application.

Many weed species can be controlled (i.e., killed or damaged) by the herbicidal composition(s) described herein. Accordingly, the methods are useful in controlling these plant species where they are undesirable (i.e., where they are weeds). These plant species include crop plants as well as species commonly considered weeds, including but not limited to species such as: blackgrass (*Alopecurus myosuroides*), giant foxtail (*Setaria faberi*), large crabgrass (*Digitaria sanguinalis*), Surinam grass (*Brachiaria decumbens*), wild oat (*Avena fatua*), common cocklebur (*Xanthium pensylvanicum*), common lambsquarters (*Chenopodium album*), morning glory (*Ipomoea* spp. And many other *Ipomoea* species including *hederacea, grandifolia*), pigweed (*Amaranthus* spp.), velvetleaf (*Abutilion theophrasti*), common barnyardgrass (*Echinochloa crus-galli*), bermudagrass (*Cynodon dactylon*), downy brome (*Bromus tectorum*), goosegrass (*Eleusine indica*), green foxtail (*Setaria viridis*), Italian ryegrass (*Lolium multiflorum*), Johnsongrass (*Sorghum halepense*), lesser canarygrass (*Phalaris minor*), windgrass (*Apera spica-venti*), wooly cupgrass (*Erichloa villosa*), yellow nutsedge (*Cyperus esculentus*), common chickweed (*Stellaria media*), common ragweed, Giant ragweed (*Ambrosia trifida*) (*Ambrosia artemisiifolia*), *Kochia scoparia*, horseweed (*Conyza canadensis*), rigid ryegrass (*Lolium rigidum*), goosegrass (*Eleucine indica*), hairy fleabane (*Conyza bonariensis*), buckhorn plantain (*Plantago lanceolata*), tropical spiderwort (*Commelina benghalensis*), field bindweed (*Convolvulus arvensis*), purple nutsedge (*Cyperus rotundus*), redvine (*Brunnichia ovata*), hemp sesbania (*Sesbania exaltata*), sicklepod (*Senna obtusifolia*), Texas blueweed (*Helianthus ciliaris*), Fall panicum (*Panicum dichotomiflorum*), Texas panicum (*Panicum texanum*), Broadleaf signalgrass (*Brachiaria*), and Devil's claws (*Proboscidea louisianica*). In other aspects of the invention, the weed comprises an herbicide-resistant ryegrass, for example, a glyphosate resistant ryegrass, a paraquat resistant ryegrass, ACCase-inhibitor resistant ryegrass, and a non-selective herbicide resistant ryegrass.

In another aspect of the invention, methods of controlling volunteer SYHT0H2 crop plants at a location are provided wherein the method comprises applying to the location one or more herbicides effective on soybeans and having a mode of action other than inhibition of HPPD.

In another aspect of the invention methods of controlling volunteer transgenic events at a location comprising SYHT0H2 crop plants are provided wherein the volunteer events comprise resistance to one or more herbicides but do not comprise resistance to HPPD inhibitors wherein the method comprises applying to the location a controlling amount of an herbicidal composition comprising one or more HPPD inhibitors.

In another aspect of the invention methods of applying herbicidal mixtures to a location wherein the herbicidal mixture comprises an HPPD inhibitor and at least one additional chemical that may not be tolerated by SYHT0H2 for the purpose of pest control (weeds, disease, insect, nematode) are provided wherein the presence of the SYHT0H2 event allows application of this mixture either pre-planting or pre-emergence by protecting against residual HPPD activity. For example, in one aspect, a typical burn-down herbicide such as paraquat is applied to the location in a pre-emerge or pre-plant burndown type application in combination with an HPPD inhibitor.

In other aspects of the invention, SYHT0H2 plants are used to improve yield. For example, soybean event SYHT0H2 exhibits a yield increase when sprayed with mesotrione pre-emergence or at an early vegetative stage as compared to the event unsprayed. For example, soybean event SYHT0H2 that receives a 2× application of mesotrione at the pre-emergence or vegetative stages may show greater yield than the unsprayed event. Accordingly, methods are provided for improving plant yield by applying to a soybean plant comprising event SYHT0H2 a growth promoting amount of an HPPD inhibitor, to thereby improve yield independent of weed pressure. The HPPD inhibitor may be mesotrione or other HPPD inhibitors. As used herein, a growth promoting amount means an amount of an HPPD inhibitor herbicide sufficient to increase plant yield by at least about two-fold, for example, at least about 5-fold, at least about 10-fold, at least about 20-fold, at least about 50-fold, at least about 100-fold, or more, when compared to SYHT0H2 plans that are not sprayed with an HPPD inhibitor herbicide. A growth promoting amount may also mean an amount of an HPPD inhibitor herbicide sufficient to increase plant yield by at least about 5%, for example, at least about 10%, at least about 20%, at least about 30%, at least about 40%, at least about 50%, at least about 60%, at least about 70%, at least about 80%, at least about 90%, at least about 100%, or more, when compared to SYHT0H2 plants that are not sprayed with an HPPD inhibitor herbicide.

In some aspects of the invention, the methods involve treating a plant of the invention and/or an area of interest (e.g., a field or area of cultivation) and/or weed with just one herbicide or other chemical such as, for example, an HPPD inhibitor.

The methods also encompass the use of simultaneous and/or sequential applications of multiple classes of herbicides. In particular, the heterologous insert containing the Avena HPPD sequence also includes a phosphinothricin acetyl transferase (PAT) sequence, which confers resistance to glutamine synthetase inhibitors such as glufosinate (alternatively called phosphinothricin). Phosphinothricin (PTC, 2-amino-4-methylphosphinobutyric acid) is a structural unit of the antibiotic phosphinothricylalanyl-alanine produced by the strain *Streptomyces viridochromogenes* Tu 494 (DSM 40736, DSM 4112). The antibiotic is active against Gram-positive and Gram-negative bacteria as well as the fungus *Botrytis cinerea*. PTC also acts as an effective herbicide. Accordingly, event SYHT0H2 may be used in combination with glutamine synthetase inhibitors, such as glufosinate. Representative glufosinate herbicides are marketed as BASTA®, LIBERTY®, RELY®, CHALLENGE®, IGNITE®, and FINALE®.

Different chemicals such as herbicides have different "residual" effects, i.e., different amounts of time for which treatment with the chemical or herbicide continues to have an effect on plants growing in the treated area. Such effects may be desirable or undesirable, depending on the desired future purpose of the treated area (e.g., field or area of cultivation). Thus, a crop rotation scheme may be chosen based on residual effects from treatments that will be used for each crop and their effect on the crop that will subsequently be grown in the same area. One of skill in the art is familiar with techniques that can be used to evaluate the residual effect of an herbicide; for example, generally, glyphosate has very little or no soil residual activity, while herbicides that act to inhibit HPPD vary in their residual activity levels. Residual activities for various herbicides are known in the art, and are known to vary with various environmental factors such as, for example, soil moisture levels, temperature, pH, and soil composition (texture and organic matter). The SYHT0H2 soybean plants find particular use in methods of growing a crop where improved tolerance to residual activity of an herbicide is beneficial.

For example, in one aspect of the invention, the SYHT0H2 soybean plants are planted to reduce the risk of damage from the residual effects of HPPD herbicides used in the preceding crop, such as where bicyclopyrone and topramezone were used in a corn crop during the previous planting.

For example, in one aspect of the invention, the SYHT0H2 soybean plants have an improved tolerance to HPPD inhibitor chemistries when applied individually, and further provide improved tolerance to combinations of herbicides. Moreover, the transgenic plants disclosed herein provide improved tolerance to treatment with additional chemicals commonly used on crops in conjunction with herbicide treatments, such as safeners, adjuvants such as non-ionic surfactants, ionic surfactants, ammonium sulfate and crop oil concentrate, and the like.

The term "safener" refers to a substance that when added to an herbicide formulation, applied to a crop seed or applied to the soil eliminates or reduces the phytotoxic effects of the herbicide to certain crops. One of ordinary skill in the art would appreciate that the choice of safener depends, in part, on the crop plant of interest and the particular herbicide or combination of herbicides included in the synergistic herbicide composition. Exemplary safeners suitable for use with the presently disclosed herbicide compositions include, but are not limited to, those disclosed in U.S. Pat. Nos. 4,808,208; 5,502,025; 6,124,240 and U.S. Patent Application Publication Nos. 2006/0148647; 2006/0030485; 2005/0233904; 2005/0049145; 2004/0224849; 2004/0224848; 2004/0224844; 2004/0157737; 2004/0018940; 2003/0171220; 2003/0130120; 2003/0078167, the disclosures of which are incorporated herein by reference in their entirety. The methods can involve the use of herbicides in combination with herbicide safeners such as benoxacor, BCS (1-bromo-4-[(chloromethyl) sulfonyl]benzene), cloquintocet-mexyl, cyometrinil, dichlormid, 2-(dichloromethyl)-2-methyl-1,3-dioxolane (MG 191), fenchlorazole-ethyl, fenclorim, flurazole, fluxofenim, furilazole, isoxadifen-ethyl, mefenpyr-diethyl, methoxyphenone ((4-methoxy-3-methylphenyl)(3-methylphenyl)-methanone), naphthalic anhydride (1,8-naphthalic anhydride), cyprosulfamide, N-(2-methoxybenzoyl)-4-[methylaminocarbonyl)amino]benzenesulfonamide, and oxabetrinil to increase crop safety. Antidotally effective amounts of the herbicide safeners can be applied at the same time as the compounds, or applied as seed treatments or to the soil. Therefore an aspect of the present invention relates to the use of a mixture comprising an HPPD inhibitor herbicide, at least one other herbicide, and an antidotally effective amount of an herbicide safener.

Seed treatment with herbicide safeners is particularly useful for selective weed control, because it physically restricts antidoting to the crop plants. Therefore another useful aspect of the invention is a method for selectively controlling the growth of weeds in a field comprising treating the seed from which the crop is grown with an antidotally effective amount of safener and treating the field with an effective amount of herbicide to control weeds. Antidotally effective amounts of safeners can be easily determined by one skilled in the art through simple experimentation. An antidotally effective amount of a safener is present where a desired plant is treated with the safener so that the effect of an herbicide on the plant is decreased in comparison to the effect of the herbicide on a plant that was not treated with the safener; generally, an antidotally effective amount of safener prevents damage or severe damage to the plant treated with the safener. One of skill in the art is capable of determining whether the use of a safener is appropriate and determining the dose at which a safener should be administered to a crop.

In one embodiment, the seeds comprising the SYHT0H2 event are treated. The following chemicals are provided as examples, but not as limitations, of possible seed treatments: Alanycarb, Aldicarb, Bendiocarb, Benfuracarb, Butocarboxim, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiodicarb, Thiofanox, Triazamate, Trimethacarb, XMC, Xylylcarb; Acephate, Azamethiphos, Azinphos-ethyl, Azinphos-methyl, Cadusafos, Chlorethoxyfos, Chlorfenvinphos, Chlormephos, Chlorpyrifos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fosthiazate, Heptenophos, Imicyafos, Isofenphos, Isopropyl O-(methoxyaminothio-phosphoryl) salicylate, Isoxathion, Malathion, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-methyl, Profenofos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Triclorfon, Vamidothion, cyclodiene organochlorines, Chlordane, Endosulfan; Ethiprole, Fipronil, Acrinathrin, Allethrin, d-cis-trans Allethrin, d-trans Allethrin, Bifenthrin, Bioallethrin, Bioallethrin S-cyclopentenyl isomer, Bioresmethrin, Cycloprothrin, Cyfluthrin, beta-Cyfluthrin, Cyhalothrin, lambda-Cyhalothrin, gamma-Cyhalothrin, Cypermethrin, alpha-Cypermethrin, beta-Cypermethrin, theta-Cypermethrin, zeta-Cypermethrin, Cyphenothrin [(1R)-trans isomers], Deltamethrin, Empenthrin [(EZ)-(1R) isomers), Esfenvalerate, Etofenprox, Fenpropathrin, Fenvalerate, Flucythrinate, Flumethrin, tau-Fluvalinate, Halfenprox, Imiprothrin, Kadethrin, Permethrin, Phenothrin [(1R)-trans isomer), Prallethrin, Pyrethrine (pyrethrum), Resmethrin, Silafluofen, Tefluthrin, Tetramethrin, Tetramethrin [(1R) isomers)], Tralomethrin, Transfluthrin; DDT; Methoxychlor, Acetamiprid, Clothianidin, Dinotefuran, Imidacloprid, Nitenpyram, Thiacloprid, Thiamethoxam; Nicotine, Spinetoram, Spinosad, Abamectin, Emamectin benzoate, Lepimectin, Milbemectin, Hydroprene, Kinoprene, Methoprene; Fenoxycarb; Pyriproxyfen, Chloropicrin; Sulfuryl fluoride; Borax; Tartar emetic, Pymetrozine; Flonic amid, Clofentezine, Hexythiazox, Diflovidazin, Etoxazole. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, BT crop proteins: Cry1Ab, Cry1Ac, Cry1Fa, Cry2Ab, mCry3A, Cry3Ab, Cry3Bb, Cry34/35Ab1, Diafenthiuron, Azocyclotin, Cyhexatin, Fenbutatin oxide; Propargite, Tetradifon, Chlorfenapyr, DNOC, Sulfluramid, Bensultap, Cartap hydrochloride, Thiocyclam, Thiosultap-sodium, Bistrifluoron, Chlorfluazuron, Diflubenzuron, Flucycloxuron, Flufenoxuron, Hexaflumuron, Lufenuron, Novaluron, Noviflumuron, Teflubenzuron, Triflumuron, Buprofezin, Cyromazine, Chromafenozide, Halofenozide, Methoxyfenozide, Tebufenozide, Amitraz, Hydramethylnon; Acequinocyl; Fluacrypyrim, Fenazaquin, Fenpyroximate, Pyrimidifen, Pyridaben, Tebufenpyrad, Tolfenpyrad, Rotenone (Derris), Indoxacarb; Metaflumizone, Spirodiclofen, Spiromesifen, Spirotetramat, Aluminium phosphide, Calcium phosphide, Phosphine, Zinc phosphide, Cyenopyrafen, Chlorantraniliprole, Flubendiamide, Amidoflumet, Azadirachtin, Benclothiaz, Benzoximate, Bifenazate, Bromopropylate, Chinomethionat, Cryolite, Cyantraniliprole (Cyazypyr), Cyflumetofen, Dicofol, Diflovidazin, Fluensulfone, Flufenerim, Flufiprole, Fluopyram, Fufenozide, Imidaclothiz, Iprodione, Meperfluthrin, Pyridalyl, Pyrifluquinazon, Tetramethylfluthrin, Iodomethane; products based on *Bacillus firmus* (including but not limited to strain CNCM I-1582, such as, for example, VOTiVO™, BioNem); 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934), 4-{[(6-bromopyridin-3-yl)methyl](2-fluoroethyl)amino}furan-2(5H)-one (known from WO2007/115644), 4-{[(6-fluoropyridin-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chlorpyridin-3-yl)methyl](2-fluoroethyl)amino}furan-2(5H)-one (known from WO2007/115644), Flupyradifurone, 4-{[(6-chlor-5-fluoropyridin-3-yl)methyl](methyl)amino}furan-2(5H)-one (known from WO2007/115643), 4-{[(5,6-dichloropyridin-3-yl)methyl](2-fluoroethyl)amino}furan-2(5H)-one (known from WO2007/115646), 4-{[(6-chloro-5-fluoropyridin-3-yl)methyl]-(cyclopropyl)-amino}-furan-2(5H)-one (known from WO2007/115643), 4-{[(6-chloropyridin-3-yl)methyl]-(cyclopropyl)-amino}furan-2(5H)-one (known from EP-A-0 539 588), 4-{[(6-chlorpyridin-3-yl)-methyl](methyl)amino}furan-2(5H)-one (known from EP-A-0 539 588), {1-(6-chloropyridin-3-yl)ethyl](methyl)oxido-$\lambda^4$-sulfanylidene}cyanamide (known from WO2007/149134) and its diastereomers {[(1R)-1-(6-chloropyridin-3-yl)ethyl](methyl)oxido-$\lambda^4$-sulfanylidene}cyanamide (A) and {[(1S)-1-(6-chloropyridin-3-yl)ethyl](methyl)oxido-$\lambda^4$-sulfanylidene}cyanamide (B) (also known from WO2007/149134) as well as Sulfoxaflor and its diastereomers [(R)-methyl(oxido){(1R)-1-[6-(trifluoromethyl)pyridin-3-yl]ethyl}-$\lambda^4$-sulfanylidene]cyanamide (A1) and [(S)-methyl(oxido){(1S)-1-[6-(trifluoromethyl)pyridin-3-yl]ethyl}-$\lambda^4$-sulfanylidene]-cyanamide (A2), referred to as group of diastereomers A (known from WO2010/074747, WO2010/074751), [(R)-methyl(oxido){(1S)-1-[6-(trifluoromethyl)pyridin-3-yl]ethyl}-$\lambda^4$-sulfanylidene]cyanamide (B1) and [(S)-methyl(oxido){(1R)-1-[6-(trifluoromethyl)pyridin-3-yl]ethyl}-$\lambda^4$-sulfanylidene]cyanamide (B2), referred to as group of diastereomers B (also known from WO2010/074747, WO2010/074751), and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluorethyl)sulfinyl]phenyl}-3-(trifluoromethyl)-1H-1,2,4-triazol-5-amine (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6, 6a,12,12a,12b-decahydro-2H,11H-benzo[f]-pyrano[4,3-b]chromen-4-yl]methyl cyclopropanecarboxylate (known from WO2008/066153), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethylbenzenesulfonamide (known from WO2005/035486), 4-(difluoromethoxy)-N-ethyl-N-methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazol-2-amine (known from WO2008/104503), {1'-[(2E)-3-(4-chlorophenyl)prop-2-en-1-yl]-5-fluorospiro[indole-3,4'-piperidin]-1 (2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diaza-spiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)-pyridazin-3-yl]-3-azabicyclo[3.2.1]octane (known from WO2007/040280), Flometoquin, PF1364 (CAS-Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]-ethyl}benzamide (known from WO2005/085216), 4-{[(6-chloropyridin-3-yl)methyl]-(cyclopropyl)amino}-1,3-oxazol-2(5H)-one, 4-{[(6-chloropyridin-3-yl)methyl](2,2-difluoroethyl)-amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO2010/005692), NNI-0711 (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl2-[2-({[3-bromo-1-(3-chloropyridin-2-yl)-1H-pyrazol-5-yl]carbonyl}-amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)-benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl]carbonyl}-amino)benzoyl]-2-ethylhydrazine-carboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), N-[2-(5-amino-1,3,4-thiadiazol-2-yl)-4-chloro-6-methylphenyl]-3-bromo-1-(3-chloro-pyridin-2-yl)-1H-pyrazole-5-carboxamide (known from CN102057925), and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO2011/049233); aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide, O-[1-(4-methoxyphenoxy)-3,3-dimethylbutan-2-yl]1H-imidazole-1-carbothioate, bixafen, boscalid, carboxin, diflumetorim, fenfuram, fluopyram, flutolanil, fluxapyroxad, furametpyr, furmecyclox, isopyrazam (mixture of syn-epimeric racemate 1RS,4SR,9RS and anti-epimeric racemate 1RS,4SR,9SR), isopyrazam (anti-epimeric racemate 1RS,4SR,9SR), isopyrazam (anti-epimeric enantiomer 1R,4S,9S), isopyrazam (anti-epimeric enantiomer 1S,4R,9R), isopyrazam (syn epimeric racemate 1RS,4SR,9RS), isopyrazam (syn-epimeric enantiomer 1R,4S,9R), isopyrazam (syn-epimeric enantiomer 1S,4R, 9S), mepronil, oxycarboxin, penflufen, penthiopyrad, sedaxane, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl]quinazolin-4-amine, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, ametoctradin, amisulbrom, azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(R2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulfanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide, (2R)-2-{2-[(2,5-dimethylphenoxy)methyl]phenyl}-2-methoxy-N-methylacetamide, benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine, 3-chloro-5-(6-chloropyridin-3-yl)-6-methyl-4-(2,4,6-trifluorophenyl)pyridazine, bordeaux mixture, captafol, captan, chlorothalonil, copper hydroxide, copper naphthenate, copper oxide, copper oxychloride, copper(2+) sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur, sulphur preparations including calcium polysulphide, thiram, tolylfluanid, zineb, ziram, acibenzolar-S-methyl, isotianil, probenazole, tiadinil, andoprim, blasticidin-S, cyprodinil, kasugamycin, kasugamycin hydrochloride hydrate, mepanipyrim, pyrimethanil, 3-(5-fluoro-3,3,4,4-tetramethyl-3,4-dihydroisoquinolin-1-yl)quinoline, fentin acetate, fentin chloride, fentin hydroxide, silthiofam, benthiavalicarb, dimethomorph, flumorph, iprovalicarb, mandipropamid, polyoxins, polyoxorim, validamycin A, valifenalate, biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene tolclofos-methyl, carpropamid, diclocymet, fenoxanil, phthalide, pyroquilon, tricyclazole, 2,2,2-trifluoroethyl {3-methyl-1-[(4-methylbenzoyl)amino]butan-2-yl}carbamate, benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl, oxolinic acid, chlozolinate, fenpiclonil, fludioxonil, iprodione, procymidone, quinoxyfen, vinclozolil, binapacryl, dinocap, ferimzone, fluazinam, meptyldinocap, benthiazole, bethoxazin, capsimycin, carvone, chinomethionat, pyrifenone (chlazafenone), cufraneb, cyflufenamid, cymoxanil, cyprosulfamide, dazomet, debacarb, dichlorophen, diclomezine, difenzoquat, difenzoquat methylsulphate, diphenylamine, ecomate, fenpyrazamine, flumetover, fluoroimide, flusulfamide, flutianil, fosetyl-aluminium, fosetyl-calcium, fosetyl-sodium, hexachlorobenzene, irumamycin, methasulfocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and salts, phenothrin, phosphorous acid and its salts, propamocarb-fosetylate, propanosine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl)prop-2-en-1-one, pyrrolnitrine, tebufloquin, tecloftalam, tolnifamide, triazoxide, trichlamide, zarilamid, (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl)pyridine, 2,3-dibutyl-6-chlorothieno[2,3-d]pyrimidin-4(3H)-one, 2,6-dimethyl-1H,5H-[1,4]dithiino[2,3-c:5,6-c′]dipyrrole-1,3,5,7(2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N′-phenyl-N′-(prop-2-yn-1-yl)thiophene-2-sulfonohydrazide, 5-fluoro-2-[(4-fluorobenzyl)oxy]pyrimidin-4-amine, 5-fluoro-2-[(4-methylbenzyl)oxy]pyrimidin-4-amine, 5-methyl-6-octyl[1,2,4]triazolo[1,5-a]pyrimidin-7-amine, ethyl (2Z)-3-amino-2-cyano-3-phenylprop-2-enoate, N′-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]-methyl}-2-phenylacetamide, N-{(Z)-[(cyclopropylmethoxy)imino][6-(difluoromethoxy)-2,3-difluorophenyl]methyl}-2-phenylacetamide, N′-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5- methyl-3-(trifluoromethyl)-1H-pyrazol-1-yl]
acetyl}piperidin-4-yl)-N-[(1R)-1,2,3,4-
tetrahydronaphthalen-1-yl]-1,3-thiazole-4-carboxamide,
N-methyl-2-(1-{[5-methyl-3-(trifluoromethyl)-1H-pyrazol-
1-yl]acetyl}piperidin-4-yl)-N-[(1S)-1,2,3,4-tetrahydronaph-
thalen-1-yl]-1,3-thiazole-4-carboxamide, pentyl {6-[({[(1-
methyl-1H-tetrazol-5-yl)(phenyl)methylidene]amino}oxy)
methyl]pyridin-2-yl}carbamate, phenazine-1-carboxylic
acid, quinolin-8-ol, quinolin-8-ol sulfate (2:1), tert-butyl
{6-[({[(1-methyl-1H-tetrazol-5-yl)(phenyl)methylene]
amino}oxy)methyl]pyridin-2-yl}carbamate, 1-methyl-3-
(trifluoromethyl)-N-[2'-(trifluoromethyl)biphenyl-2-yl]-1H-
pyrazole-4-carboxamide, N-(4'-chlorobiphenyl-2-yl)-3-
(difluoromethyl)-1-methyl-1H-pyrazole-4-carboxamide,
N-(2',4'-dichlorobiphenyl-2-yl)-3-(difluoromethyl)-1-
methyl-1H-pyrazole-4-carboxamide, 3-(difluoromethyl)-1-
methyl-N-[4'-(trifluoromethyl)biphenyl-2-yl]-1H-pyrazole-
4-carboxamide, N-(2',5'-difluorobiphenyl-2-yl)-1-methyl-3-
(trifluoromethyl)-1H-pyrazole-4-carboxamide,
3-(difluoromethyl)-1-methyl-N-[4'-(prop-1-yn-1-yl)biphe-
nyl-2-yl]-1H-pyrazole-4-carboxamide, 5-fluoro-1,3-dim-
ethyl-N-[4'-(prop-1-yn-1-yl)biphenyl-2-yl]-1H-pyrazole-4-
carboxamide, 2-chloro-N-[4'-(prop-1-yn-1-yl)biphenyl-2-
yl]pyridine-3-carboxamide, 3-(difluoromethyl)-N-[4'-(3,3-
dimethylbut-1-yn-1-yl)biphenyl-2-yl]-1-methyl-1H-
pyrazole-4-carboxamide, N-[4'-(3,3-dimethylbut-1-yn-1-yl)
biphenyl-2-yl]-5-fluoro-1,3-dimethyl-1H-pyrazole-4-
carboxamide, 3-(difluoromethyl)-N-(4'-ethynylbiphenyl-2-
yl)-1-methyl-1H-pyrazole-4-carboxamide, N-(4'-
ethynylbiphenyl-2-yl)-5-fluoro-1,3-dimethyl-1H-pyrazole-
4-carboxamide, 2-chloro-N-(4'-ethynylbiphenyl-2-yl)
pyridine-3-carboxamide, 2-chloro-N-[4'-(3,3-dimethylbut-
1-yn-1-yl)biphenyl-2-yl]pyridine-3-carboxamide,
4-(difluoromethyl)-2-methyl-N-[4'-(trifluoromethyl)biphe-
nyl-2-yl]-1,3-thiazole-5-carboxamide, 5-fluoro-N-[4'-(3-hy-
droxy-3-methylbut-1-yn-1-yl)biphenyl-2-yl]-1,3-dimethyl-
1H-pyrazole-4-carboxamide, 2-chloro-N-[4'-(3-hydroxy-3-
methylbut-1-yn-1-yl)biphenyl-2-yl]pyridine-3-
carboxamide, 3-(difluoromethyl)-N-[4'-(3-methoxy-3-
methylbut-1-yn-1-yl)biphenyl-2-yl]-1-methyl-1H-pyrazole-
4-carboxamide, 5-fluoro-N-[4'-(3-methoxy-3-methylbut-1-
yn-1-yl)biphenyl-2-yl]-1,3-dimethyl-1H-pyrazole-4-
carboxamide, 2-chloro-N-[4'-(3-methoxy-3-methylbut-1-
yn-1-yl)biphenyl-2-yl]pyridine-3-carboxamide, (5-bromo-
2-methoxy-4-methylpyridin-3-yl)(2,3,4-trimethoxy-6-
methylphenyl)methanone, N-[2-(4-{[3-(4-chlorophenyl)
prop-2-yn-1-yl]oxy}-3-methoxyphenyl)ethyl]-N2-
(methylsulfonyl)valinamide, 4-oxo-4-[(2-phenylethyl)
amino]butanoic acid, but-3-yn-1-yl {6-[({[(Z)-(1-methyl-
1H-tetrazol-5-yl)(phenyl)-methylene]amino}oxy)methyl]
pyridin-2-yl}carbamate.

In other aspects of the invention, the herbicide or herbicide combination applied to the SYHT0H2 plant acts as a safener. For example, a first herbicide or an herbicide mixture is applied at an antidotally effect amount to the plant. For example, the method can comprise planting a cultivation area with crop seeds or plants which comprise a first polynucleotide encoding a polypeptide that can confer tolerance to an HPPD inhibitor herbicide operably linked to a promoter active in a plant; and, a second polynucleotide encoding a polypeptide that confers herbicide tolerance operably linked to a promoter active in a plant. A combination of herbicides comprising at least an effective amount of a first and a second herbicide is applied to the crop, crop part, weed, or area of cultivation thereof. The effective amount of the herbicide combination controls weeds; and, the effective amount of the first herbicide is not tolerated by the crop when applied alone when compared to a control crop that has not been exposed to the first herbicide; and, the effective amount of the second herbicide is sufficient to produce a safening effect, wherein the safening effect provides an increase in crop tolerance upon the application of the first and the second herbicide when compared to the crop tolerance when the first herbicide is applied alone.

In specific aspects of the invention, the combination of safening herbicides comprises a first HPPD inhibitor and a second HPPD inhibitor. In other aspects of the invention, the safening effect is achieved by applying an effective amount of a combination of an HPPD inhibitor and at least one additional herbicide. Such mixtures provide increased crop tolerance (i.e., a decrease in herbicidal injury). This method allows for increased application rates of the chemistries post or pre-treatment.

In another aspect of the invention, a site for targeted insertion of heterologous nucleic acids other than *Avena sativa* HPPD, which is the same site as SYHT0H2, is provided. See Examples 5 and 6.

In a further aspect of the invention, the seed of a soybean plant comprising event SYHT0H2 as well as various parts of the soybean plant can be utilized for human food, livestock feed, and as a raw material in industry. The soybean seed can be crushed or a component of the soybean seed can be extracted in order to comprise a component for a food or feed product.

The soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board and American Soybean Association Special Report 92S, May 1990). Changes in fatty acid composition for improved oxidative stability and nutrition are constantly sought after. Industrial uses of soybean oil which is subjected to further processing include ingredients for paints, plastics, fibers, detergents, cosmetics, lubricants and biodiesel fuel. Soybean oil may be split, inter-esterified, sulfurized, epoxidized, polymerized, ethoxylated, or cleaved. Designing and producing soybean oil derivatives with improved functionality and improved oliochemistry is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein.

For human consumption soybean meal is made into soybean flour which is processed to protein concentrates used for meat extenders or specialty pet foods. Production of edible protein ingredients from soybean offers a healthier, less expensive replacement for animal protein in meats as well as in dairy-type products.

The production process of for this products may proceed for example as follows: (i) heating of the beans up to 82° C. until they contain only 9% of moisture; (ii) placement in barrels during 24 to 72 hours; (iii) crushing of the beans to remove the sheath so that the residuals measure between ¼ and V8 of the original beans; (iv) removal of the sheath through air suction; (v) heating of the residuals at 71° C. during 20 to 30 minutes; (vi) pressing of the residuals into small flakes with a thickness from 1.2 to 1.6 millimeters; (vii) treatment to create 'collets' with the help of mechanical pressure and steam; (viii) washing with hexane to dilute the fats; (ix) heating at 100° C. during 20 minutes to evaporate the fats (the recuperated fats produce soybean oil); (x) additional heating to remove the hexane; (xi) pressing of the collets in parts of 2 to 4 millimeters to produce soya meal or pressing in soya feeding cake.

Aspects of the invention are further described in the following Examples. It should be understood that these Examples are given by way of illustration only. From the above discussion and these Examples, one skilled in the art can ascertain the essential characteristics, and without departing from the spirit and scope thereof, can make various changes and modifications of the aspects of the invention of the invention to adapt it to various usages and conditions. Thus, various modifications of the aspects of the invention of the invention, in addition to those shown and described herein, will be apparent to those skilled in the art from the foregoing description. Such modifications are intended to fall within the scope of the appended claims.

Combinations and Applications

The following tables provide examples of possible breeding stacks that may be crossed with SYHT0H2 including (i) known transgenic events, (see Table 2) (ii) potential combinations of traits that could be genetically engineered into SYHT0H2 or (iii) genetically engineered into a new transgenic event and subsequently crossed with SYHT0H2 (see Table 3), and possible herbicidal compositions for use on such stacks. (see Tables 2 and 3)

For any of this combination it is always possible (i) only to use an HPPD inhibitor (for example, 25 to 500 g/ha sulcotrione, 25 to 250 g/ha mesotrione, 25 to 250 g/ha bicyclopyrone, 25 to 250 g/ha isoxaflutole, 25 to 250 g/ha tembotrione, 5 to 250 g/ha topramezone), 5 to 250 g/ha pyrasulfatole (ii) to use a combination in form of a tank mix, and/or (iii) to use an application in form of a subsequent application. In that sense "+" as indicated in the tables below means any application of the indicated herbicides to the same field of plants. It includes both mixes and subsequent applications where the time and order of application can vary.

TABLE 2

| Breeding stack containing in addition to SYT0H2 | Herbicidal composition comprising |
|---|---|
| Glyphosate resistance e.g EPSPS (e.g GTS 40-3-2, MON89788, FG72, DP-356043-5) | a. 25 to 500 g/ha sulcotrione + (optionally) 350 to 2000 g/ha glyphosate<br>b. 25 to 250 g/ha mesotrione + (optionally) 350 to 2000 g/ha glyphosate<br>c. 25 to 250 g/ha bicyclopyrone + (optionally) 350 to 2000 g/ha glyphosate<br>d. 25 to 250 g/ha isoxaflutole + (optionally) 350 to 2000 g/ha glyphosate<br>e. 25 to 250 g/ha tembotrione + (optionally) 350 to 2000 g/ha glyphosate<br>f. 5 to 250 g/ha topramezone + (optionally) 350 to 2000 g/ha glyphosate<br>g. 5 to 250 g/ha pyrasulfatole + (optionally) 350 to 2000 g/ha glyphosate |
| Glufosinate resistance e.g pat/bar (e.g A2704-12, DAS-68416-4, A5547-127, GU262) | a. 25 to 500 g/ha sulcotrione + (optionally) 200 to 1500 g/ha glufosinate<br>b. 25 to 250 g/ha mesotrione + (optionally) 200 to 1500 g/ha glufosinate<br>c. 25 to 250 g/ha bicyclopyrone + (optionally) 200 to 1500 g/ha glufosinate<br>d. 25 to 250 g/ha isoxaflutole + (optionally) 200 to 1500 g/ha glufosinate<br>e. 25 to 250 g/ha tembotrione + (optionally) 200 to 1500 g/ha glufosinate<br>f. 5 to 250 g/ha topramezone + (optionally) 200 to 1500 g/ha glufosinate<br>g. 5 to 250 g/ha pyrasulfatole + (optionally) 200 to 1500 g/ha glufosinate |
| 2,4-D tolerance (e.g DAS-68416-4, DAS-40278-9) | a. 25 to 500 g/ha sulcotrione + (optionally) 100 to 2000 g/ha 2,4-D<br>b. 25 to 250 g/ha mesotrione + (optionally) 100 to 2000 g/ha 2,4-D<br>c. 25 to 250 g/ha bicyclopyrone + (optionally) 100 to 2000 g/ha 2,4-D<br>d. 25 to 250 g/ha isoxaflutole + (optionally) 100 to 2000 g/ha 2,4-D<br>e. 25 to 250 g/ha tembotrione + (optionally) 100 to 2000 g/ha 2,4-D<br>f. 5 to 250 g/ha topramezone + (optionally) 100 to 2000 g/ha 2,4-D<br>g. 5 to 250 g/ha pyrasulfatole + (optionally) 100 to 2000 g/ha 2,4-D |
| Dicamba Tolerance (e.g MON87708) | a. 25 to 500 g/ha sulcotrione + (optionally) 50 to 2000 g/ha dicamba<br>b. 25 to 250 g/ha mesotrione + (optionally) 50 to 2000 g/ha dicamba<br>c. 25 to 250 g/ha bicyclopyrone + (optionally) 50 to 2000 g/ha dicamba<br>d. 25 to 250 g/ha isoxaflutole + (optionally) 50 to 2000 g/ha dicamba |

TABLE 2-continued

| Breeding stack containing in addition to SYT0H2 | Herbicidal composition comprising |
|---|---|
| | e. 25 to 250 g/ha tembotrione + (optionally) 50 to 2000 g/ha dicamba |
| | f. 5 to 250 g/ha topramezone + (optionally) 50 to 2000 g/ha dicamba |
| | g. 5 to 250 g/ha pyrasulfatole + (optionally) 50 to 2000 g/ha dicamba |
| ALS Tolerance (e.g DP-356043-5, 127, BPS-CV127-9) | a. 25 to 500 g/ha sulcotrione + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | b. 25 to 250 g/ha mesotrione + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | c. 25 to 250 g/ha bicyclopyrone + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic,, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | d. 25 to 250 g/ha isoxaflutole + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic,, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | e. 25 to 250 g/ha tembotrione + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic,, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | f. 5 to 250 g/ha topramezone + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic,, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | g. 5 to 250 g/ha pyrasulfatole + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |

TABLE 2-continued

| Breeding stack containing in addition to SYT0H2 | Herbicidal composition comprising |
|---|---|
| Glyphosate resistance e.g EPSPS (e.g GTS 40-3-2, MON89788, FG72, DP-356043-5) and Glufosinate resistance e.g pat/ bar (e.g A2704-12, DAS-68416-4, A5547-127, GU262) | a. 25 to 500 g/ha sulcotrione + (optionally) 200 to 1500 g/ha glufosinate + (optionally) 350 to 2000 g/ha glyphosate<br>b. 25 to 250 g/ha mesotrione + (optionally) 200 to 1500 g/ha glufosinate + (optionally) 350 to 2000 g/ha glyphosate<br>c. 25 to 250 g/ha bicyclopyrone + (optionally) 200 to 1500 g/ha glufosinate + (optionally) 350 to 2000 g/ha glyphosate<br>d. 25 to 250 g/ha isoxaflutole + (optionally) 200 to 1500 g/ha glufosinate + (optionally) 350 to 2000 g/ha glyphosate<br>e. 25 to 250 g/ha tembotrione + (optionally) 200 to 1500 g/ha glufosinate + (optionally) 350 to 2000 g/ha glyphosate<br>f. 5 to 250 g/ha topramezone + (optionally) 200 to 1500 g/ha glufosinate + (optionally) 350 to 2000 g/ha glyphosate<br>g. 5 to 250 g/ha pyrasulfatole + (optionally) 200 to 1500 g/ha glufosinate + (optionally) 350 to 2000 g/ha glyphosate |
| Glyphosate resistance e.g EPSPS (e.g GTS 40-3-2, MON89788, FG72, DP-356043-5) and Glufosinate resistance e.g pat/ bar (e.g A2704-12, DAS-68416-4, A5547-127, GU262) and Dicamba Tolerance (e.g MON87708) | a. 25 to 500 g/ha sulcotrione + (optionally) 200 to 1500 g/ha glufosinate + (optionally) 350 to 2000 g/ha glyphosate + (optionally) 50 to 2000 g/ha dicamba<br>b. 25 to 250 g/ha mesotrione + (optionally) 200 to 1500 g/ha glufosinate + (optionally) 350 to 2000 g/ha glyphosate + (optionally) 50 to 2000 g/ha dicamba<br>c. 25 to 250 g/ha bicyclopyrone + (optionally) 200 to 1500 g/ha glufosinate + (optionally) 350 to 2000 g/ha glyphosate + (optionally) 50 to 2000 g/ha dicamba<br>d. 25 to 250 g/ha isoxaflutole + (optionally) 200 to 1500 g/ha glufosinate + (optionally) 350 to 2000 g/ha glyphosate + (optionally) 50 to 2000 g/ha dicamba<br>e. 25 to 250 g/ha tembotrione + (optionally) 200 to 1500 g/ha glufosinate + (optionally) 350 to 2000 g/ha glyphosate + (optionally) 50 to 2000 g/ha dicamba<br>f. 5 to 250 g/ha topramezone + (optionally) 200 to 1500 g/ha glufosinate + (optionally) 350 to 2000 g/ha glyphosate + (optionally) 50 to 2000 g/ha dicamba<br>g. 5 to 250 g/ha pyrasulfatole + (optionally) 200 to 1500 g/ha glufosinate + (optionally) 350 to 2000 g/ha glyphosate + (optionally) 50 to 2000 g/ha dicamba |
| Glyphosate resistance e.g EPSPS (e.g GTS 40-3-2, MON89788, FG72, DP-356043-5) and Glufosinate resistance e.g pat/ bar (e.g A2704-12. DAS-68416-4, A5547-127, GU262) and 2,4-D tolerance (e.g DAS-68416-4, DAS-40278-9)) | a. 25 to 500 g/ha sulcotrione + (optionally) 200 to 1500 g/ha glufosinate + (optionally) 350 to 2000 g/ha glyphosate + (optionally) 100 to 2000 g/ha 2,4-D<br>b. 25 to 250 g/ha mesotrione + (optionally) 200 to 1500 g/ha glufosinate + (optionally) 350 to 2000 g/ha glyphosate + (optionally) 100 to 2000 g/ha 2,4-D<br>c. 25 to 250 g/ha bicyclopyrone + (optionally) 200 to 1500 g/ha glufosinate + (optionally) 350 to 2000 g/ha glyphosate + (optionally) 100 to 2000 g/ha 2,4-D<br>d. 25 to 250 g/ha isoxaflutole + (optionally) 200 to 1500 g/ha glufosinate + (optionally) 350 to 2000 g/ha glyphosate + (optionally) 100 to 2000 g/ha 2,4-D<br>e. 25 to 250 g/ha tembotrione + (optionally) 200 to 1500 g/ha glufosinate + (optionally) 350 to 2000 g/ha glyphosate + (optionally) 100 to 2000 g/ha 2,4-D<br>f. 5 to 250 g/ha topramezone + (optionally) 200 to 1500 g/ha glufosinate + (optionally) 350 to 2000 g/ha glyphosate + (optionally) 100 to 2000 g/ha 2,4-D<br>g. 5 to 250 g/ha pyrasulfatole + (optionally) 200 to 1500 g/ha glufosinate + (optionally) 350 to 2000 g/ha glyphosate + (optionally) 100 to 2000 g/ha 2,4-D |

TABLE 3

| Molecular Stack comprising in addition: | Herbicidal composition comprising |
|---|---|
| Glyphosate resistance e.g EPSPS, GAT, GOX | a. 25 to 500 g/ha sulcotrione + (optionally) 350 to 2000 g/ha glyphosate<br>b. 25 to 250 g/ha mesotrione + (optionally) 350 to 2000 g/ha glyphosate<br>c. 25 to 250 g/ha bicyclopyrone + (optionally) 350 to 2000 g/ha glyphosate<br>d. 25 to 250 g/ha isoxaflutole + (optionally) 350 to 2000 g/ha glyphosate<br>e. 25 to 250 g/ha tembotrione + (optionally) 350 to 2000 g/ha glyphosate |

TABLE 3-continued

| Molecular Stack comprising in addition: | | Herbicidal composition comprising |
|---|---|---|
| | f. | 5 to 250 g/ha topramezone + (optionally) 350 to 2000 g/ha glyphosate |
| | g. | 5 to 250 g/ha pyrasulfatole + (optionally) 350 to 2000 g/ha glyphosate |
| Glufosinate resistance e.g. PAT, BAR | a. | 25 to 500 g/ha sulcotrione + (optionally) 200 to 1500 g/ha glufosinate |
| | b. | 25 to 250 g/ha mesotrione + (optionally) 200 to 1500 g/ha glufosinate |
| | c. | 25 to 250 g/ha bicyclopyrone + (optionally) 200 to 1500 g/ha glufosinate |
| | d. | 25 to 250 g/ha isoxaflutole + (optionally) 200 to 1500 g/ha glufosinate |
| | e. | 25 to 250 g/ha tembotrione + (optionally) 200 to 1500 g/ha glufosinate |
| | f. | 5 to 250 g/ha topramezone + (optionally) 200 to 1500 g/ha glufosinate |
| | g. | 5 to 250 g/ha pyrasulfatole + (optionally) 200 to 1500 g/ha glufosinate |
| 2,4-D tolerance e.g. tfdA, AAD-1, AAD-12, AAD-13 | a. | 25 to 500 g/ha sulcotrione + (optionally) 100 to 2000 g/ha 2,4-D |
| | b. | 25 to 250 g/ha mesotrione + (optionally) 100 to 2000 g/ha 2,4-D |
| | c. | 25 to 250 g/ha bicyclopyrone + (optionally) 100 to 2000 g/ha 2,4-D |
| | d. | 25 to 250 g/ha isoxaflutole + (optionally) 100 to 2000 g/ha 2,4-D |
| | e. | 25 to 250 g/ha tembotrione + (optionally) 100 to 2000 g/ha 2,4-D |
| | f. | 5 to 250 g/ha topramezone + (optionally) 100 to 2000 g/ha 2,4-D |
| | g. | 5 to 250 g/ha pyrasulfatole + (optionally) 100 to 2000 g/ha 2,4-D |
| Dicamba Tolerance e.g. dicamba monoxygenase (DMO) | a. | 25 to 500 g/ha sulcotrione + (optionally) 50 to 2000 g/ha dicamba |
| | b. | 25 to 250 g/ha mesotrione + (optionally) 50 to 2000 g/ha dicamba |
| | c. | 25 to 250 g/ha bicyclopyrone + (optionally) 50 to 2000 g/ha dicamba |
| | d. | 25 to 250 g/ha isoxaflutole + (optionally) 50 to 2000 g/ha dicamba |
| | e. | 25 to 250 g/ha tembotrione + (optionally) 50 to 2000 g/ha dicamba |
| | f. | 5 to 250 g/ha topramezone + (optionally) 50 to 2000 g/ha dicamba |
| | g. | 5 to 250 g/ha pyrasulfatole + (optionally) 50 to 2000 g/ha dicamba |
| ALS Tolerance e.g. S4 and Hra | a. | 25 to 500 g/ha sulcotrione + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | b. | 25 to 250 g/ha mesotrione + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | c. | 25 to 250 g/ha bicyclopyrone + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic,, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | d. | 25 to 250 g/ha isoxaflutole + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic,, imazapyr, imazethapyr, imazamox, |

TABLE 3-continued

| Molecular Stack comprising in addition: | | Herbicidal composition comprising |
|---|---|---|
| | | iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | e. | 25 to 250 g/ha tembotrione + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic,, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | f. | 5 to 250 g/ha topramezone + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | g. | 5 to 250 g/ha pyrasulfatole + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| Glyphosate resistance e.g EPSPS, GAT, GOX and Glufosinate resistance e.g. PAT, BAR | a. | 25 to 500 g/ha sulcotrione + (optionally) 200 to 1500 g/ha glufosinate + (optionally) 350 to 2000 g/ha glyphosate |
| | b. | 25 to 250 g/ha mesotrione + (optionally) 200 to 1500 g/ha glufosinate + (optionally) 350 to 2000 g/ha glyphosate |
| | c. | 25 to 250 g/ha bicyclopyrone + (optionally) 200 to 1500 g/ha glufosinate + (optionally) 350 to 2000 g/ha glyphosate |
| | d. | 25 to 250 g/ha isoxaflutole + (optionally) 200 to 1500 g/ha glufosinate + (optionally) 350 to 2000 g/ha glyphosate |
| | e. | 25 to 250 g/ha tembotrione + (optionally) 200 to 1500 g/ha glufosinate + (optionally) 350 to 2000 g/ha glyphosate |
| | f. | 5 to 250 g/ha topramezone + (optionally) 200 to 1500 g/ha glufosinate + (optionally) 350 to 2000 g/ha glyphosate |
| | g. | 5 to 250 g/ha pyrasulfatole + (optionally) 200 to 1500 g/ha glufosinate + (optionally) 350 to 2000 g/ha glyphosate |
| Glyphosate resistance e.g EPSPS, GAT, GOX and 2,4-D tolerance e.g. tfdA, AAD-1, AAD-12, AAD-13 | a. | 25 to 500 g/ha sulcotrione + (optionally) 350 to 2000 g/ha glyphosate + (optionally) 100 to 2000 g/ha 2,4-D |
| | b. | 25 to 250 g/ha mesotrione + (optionally) 350 to 2000 g/ha glyphosate + (optionally) 100 to 2000 g/ha 2,4-D |
| | c. | 25 to 250 g/ha bicyclopyrone + (optionally) 350 to 2000 g/ha glyphosate + (optionally) 100 to 2000 g/ha 2,4-D |
| | d. | 25 to 250 g/ha isoxaflutole + (optionally) 350 to 2000 g/ha glyphosate + (optionally) 100 to 2000 g/ha 2,4-D |
| | e. | 25 to 250 g/ha tembotrione + (optionally) 350 to 2000 g/ha glyphosate + (optionally) 100 to 2000 g/ha 2,4-D |
| | f. | 5 to 250 g/ha topramezone + (optionally) 350 to 2000 g/ha glyphosate + (optionally) 100 to 2000 g/ha 2,4-D |
| | g. | 5 to 250 g/ha pyrasulfatole + (optionally) 350 to 2000 g/ha glyphosate + (optionally) 100 to 2000 g/ha 2,4-D |
| Glufosinate resistance e.g. PAT, BAR and 2,4-D tolerance e.g. tfdA, AAD-1, AAD-12, AAD-13 | a. | 25 to 500 g/ha sulcotrione + (optionally) 200 to 1500 g/ha glufosinate + (optionally) 100 to 2000 g/ha 2,4-D |
| | b. | 25 to 250 g/ha mesotrione + (optionally) 200 to 1500 g/ha glufosinate + (optionally) 100 to 2000 g/ha 2,4-D |
| | c. | 25 to 250 g/ha bicyclopyrone + (optionally) 200 to 1500 g/ha glufosinate + (optionally) 100 to 2000 g/ha 2,4-D |
| | d. | 25 to 250 g/ha isoxaflutole + (optionally) 200 to 1500 g/ha glufosinate + (optionally) 100 to 2000 g/ha 2,4-D |
| | e. | 25 to 250 g/ha tembotrione + (optionally) 200 to 1500 g/ha glufosinate + (optionally) 100 to 2000 g/ha 2,4-D |
| | f. | 5 to 250 g/ha topramezone + (optionally) 200 to 1500 g/ha glufosinate + (optionally) 100 to 2000 g/ha 2,4-D |
| | g. | 5 to 250 g/ha pyrasulfatole + (optionally) 200 to 1500 g/ha glufosinate + (optionally) 100 to 2000 g/ha 2,4-D |

TABLE 3-continued

| Molecular Stack comprising in addition: | Herbicidal composition comprising | |
|---|---|---|
| Glyphosate resistance e.g EPSPS, GAT, GOX and Dicamba tolerance e.g. DMO | a. | 25 to 500 g/ha sulcotrione + (optionally) 350 to 2000 g/ha glyphosate + (optionally) 50 to 2000 g/ha dicamba |
| | b. | 25 to 250 g/ha mesotrione + (optionally) 350 to 2000 g/ha glyphosate + (optionally) 50 to 2000 g/ha dicamba |
| | c. | 25 to 250 g/ha bicyclopyrone + (optionally) 350 to 2000 g/ha glyphosate + (optionally) 50 to 2000 g/ha dicamba |
| | d. | 25 to 250 g/ha isoxaflutole + (optionally) 350 to 2000 g/ha glyphosate + (optionally) 50 to 2000 g/ha dicamba |
| | e. | 25 to 250 g/ha tembotrione + (optionally) 350 to 2000 g/ha glyphosate + (optionally) 50 to 2000 g/ha dicamba |
| | f. | 5 to 250 g/ha topramezone + (optionally) 350 to 2000 g/ha glyphosate + (optionally) 50 to 2000 g/ha dicamba |
| | g. | 5 to 250 g/ha pyrasulfatole + (optionally) 350 to 2000 g/ha glyphosate + (optionally) 50 to 2000 g/ha dicamba |
| Glufosinate resistance e.g. PAT, BAR and Dicamba tolerance e.g. DMO | a. | 25 to 500 g/ha sulcotrione + (optionally) 200 to 1500 g/ha glufosinate + (optionally) 50 to 2000 g/ha dicamba |
| | b. | 25 to 250 g/ha mesotrione + (optionally) 200 to 1500 g/ha glufosinate + (optionally) 50 to 2000 g/ha dicamba |
| | c. | 25 to 250 g/ha bicyclopyrone + (optionally) 200 to 1500 g/ha glufosinate + (optionally) 50 to 2000 g/ha dicamba |
| | d. | 25 to 250 g/ha isoxaflutole + (optionally) 200 to 1500 g/ha glufosinate + (optionally) 50 to 2000 g/ha dicamba |
| | e. | 25 to 250 g/ha tembotrione + (optionally) 200 to 1500 g/ha glufosinate + (optionally) 50 to 2000 g/ha dicamba |
| | f. | 5 to 250 g/ha topramezone + (optionally) 200 to 1500 g/ha glufosinate + (optionally) 50 to 2000 g/ha dicamba |
| | g. | 5 to 250 g/ha pyrasulfatole + (optionally) 200 to 1500 g/ha glufosinate + (optionally) 50 to 2000 g/ha dicamba |
| Glyphosate resistance e.g EPSPS, GAT, GOX and Glufosinate resistance e.g. PAT, BAR and Dicamba tolerance e.g. DMO | a. | 25 to 500 g/ha sulcotrione + (optionally) 200 to 1500 g/ha glufosinate + (optionally) 350 to 2000 g/ha glyphosate + (optionally) 50 to 2000 g/ha dicamba |
| | b. | 25 to 250 g/ha mesotrione + (optionally) 200 to 1500 g/ha glufosinate + (optionally) 350 to 2000 g/ha glyphosate + (optionally) 50 to 2000 g/ha dicamba |
| | c. | 25 to 250 g/ha bicyclopyrone + (optionally) 200 to 1500 g/ha glufosinate + (optionally) 350 to 2000 g/ha glyphosate + (optionally) 50 to 2000 g/ha dicamba |
| | d. | 25 to 250 g/ha isoxaflutole + (optionally) 200 to 1500 g/ha glufosinate + (optionally) 350 to 2000 g/ha glyphosate + (optionally) 50 to 2000 g/ha dicamba |
| | e. | 25 to 250 g/ha tembotrione + (optionally) 200 to 1500 g/ha glufosinate + (optionally) 350 to 2000 g/ha glyphosate + (optionally) 50 to 2000 g/ha dicamba |
| | f. | 5 to 250 g/ha topramezone + (optionally) 200 to 1500 g/ha glufosinate + (optionally) 350 to 2000 g/ha glyphosate + (optionally) 50 to 2000 g/ha dicamba |
| | g. | 5 to 250 g/ha pyrasulfatole + (optionally) 200 to 1500 g/ha glufosinate + (optionally) 350 to 2000 g/ha glyphosate + (optionally) 50 to 2000 g/ha dicamba |
| Glyphosate resistance e.g EPSPS, GAT, GOX and Glufosinate resistance e.g. PAT, BAR and 2,4-D tolerance e.g. tfdA, AAD-1, AAD-12, AAD-13 | a. | 25 to 500 g/ha sulcotrione + (optionally) 200 to 1500 g/ha glufosinate + (optionally) 350 to 2000 g/ha glyphosate + (optionally) 100 to 2000 g/ha 2,4-D |
| | b. | 25 to 250 g/ha mesotrione + (optionally) 200 to 1500 g/ha glufosinate + (optionally) 350 to 2000 g/ha glyphosate + (optionally) 100 to 2000 g/ha 2,4-D |
| | c. | 25 to 250 g/ha bicyclopyrone + (optionally) 200 to 1500 g/ha glufosinate + (optionally) 350 to 2000 g/ha glyphosate + (optionally) 100 to 2000 g/ha 2,4-D |
| | d. | 25 to 250 g/ha isoxaflutole + (optionally) 200 to 1500 g/ha glufosinate + (optionally) 350 to 2000 g/ha glyphosate + (optionally) 100 to 2000 g/ha 2,4-D |
| | e. | 25 to 250 g/ha tembotrione + (optionally) 200 to 1500 g/ha glufosinate + (optionally) 350 to 2000 g/ha glyphosate + (optionally) 100 to 2000 g/ha 2,4-D |
| | f. | 5 to 250 g/ha topramezone + (optionally) 200 to 1500 g/ha glufosinate + (optionally) 350 to 2000 g/ha glyphosate + (optionally) 100 to 2000 g/ha 2,4-D |
| | g. | 5 to 250 g/ha pyrasulfatole + (optionally) 200 to 1500 g/ha glufosinate + (optionally) 350 to 2000 g/ha glyphosate + (optionally) 100 to 2000 g/ha 2,4-D |
| Glyphosate resistance e.g EPSPS, GAT, GOX and Glufosinate resistance e.g. PAT, BAR and ALS | a. | 25 to 500 g/ha sulcotrione + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, |

TABLE 3-continued

| Molecular Stack comprising in addition: | | Herbicidal composition comprising |
|---|---|---|
| inhibitor tolerance, e.g. Sr4, Hra | | chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | b. | 25 to 250 g/ha mesotrione + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | c. | 25 to 250 g/ha bicyclopyrone + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | d. | 25 to 250 g/ha isoxaflutole + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | e. | 25 to 250 g/ha tembotrione + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | f. | 5 to 250 g/ha topramezone + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| | g. | 5 to 250 g/ha pyrasulfatole + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl |
| Glyphosate resistance e.g EPSPS, GAT, GOX and Glufosinate resistance e.g. PAT, | a. | 25 to 500 g/ha sulcotrione + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, |

TABLE 3-continued

| Molecular Stack comprising in addition: | Herbicidal composition comprising |
|---|---|
| BAR and ALS inhibitor tolerance, e.g. Sr4, Hra and Dicamba tolerance e.g. DMO | rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl + (optionally) 50 to 2000 g/ha dicamba |
| | b. 25 to 250 g/ha mesotrione + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl + (optionally) 50 to 2000 g/ha dicamba |
| | c. 25 to 250 g/ha bicyclopyrone + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl + (optionally) 50 to 2000 g/ha dicamba |
| | d. 25 to 250 g/ha isoxaflutole + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl + (optionally) 50 to 2000 g/ha dicamba |
| | e. 25 to 250 g/ha tembotrione + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl + (optionally) 50 to 2000 g/ha dicamba |
| | f. 5 to 250 g/ha topramezone + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl + (optionally) 50 to 2000 g/ha dicamba |
| | g. 5 to 250 g/ha pyrasulfatole + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, |

TABLE 3-continued

| Molecular Stack comprising in addition: | Herbicidal composition comprising |
|---|---|
| | thiazopyr, diclosulam, cloransulam-methyl, flucarbazone, flumetsulam, thiencarbazone, chlorimuron-ethyl + (optionally) 50 to 2000 g/ha dicamba |
| Glyphosate resistance e.g EPSPS, GAT, GOX and Glufosinate resistance e.g. PAT, BAR and ALS inhibitor tolerance, e.g. Sr4, Hra and 2,4-D tolerance e.g. tfdA, AAD-1, AAD-12, AAD-13 | a. 25 to 500 g/ha sulcotrione + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl + (optionally) 100 to 2000 g/ha 2,4-D<br>b. 25 to 250 g/ha mesotrione + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl + (optionally) 100 to 2000 g/ha 2,4-D<br>c. 25 to 250 g/ha bicyclopyrone + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl + (optionally) 100 to 2000 g/ha 2,4-D<br>d. 25 to 250 g/ha isoxaflutole + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl + (optionally) 100 to 2000 g/ha 2,4-D<br>e. 25 to 250 g/ha tembotrione + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl + (optionally) 100 to 2000 g/ha 2,4-D<br>f. 5 to 250 g/ha topramezone + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl + (optionally) 100 to 2000 g/ha 2,4-D |

TABLE 3-continued

| Molecular Stack comprising in addition: | Herbicidal composition comprising |
|---|---|
| | g. 5 to 250 g/ha pyrasulfatole + (optionally) 200 to 1500 g/ha glufosinate + (optionally) 350 to 2000 g/ha glyphosate + (optionally) 5-500 g/ha of any herbicide or combination of herbicides selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, chlorimuron-ethyl + (optionally) 100 to 2000 g/ha 2,4-D |

These tables are provided only as examples. Possible traits that may be included in a breeding stack with or genetically engineered into SYHT0H2 include but are not limited to: traits encoding glyphosate resistance (e.g., resistant plant or bacterial EPSPS, GOX, GAT), glufosinate resistance (e.g., PAT, BAR), acetolactate synthase (ALS)-inhibiting herbicide resistance (e.g., imidazolinones [such as imazethapyr], sulfonylureas, triazolopyrimidine sulfonanilide, pyrmidinylthiobenzoates, and other chemistries), bromoxynil resistance (e.g., Bxn), resistance to inhibitors of HPPD (e.g. 4-hydroxlphenyl-pyruvate-dioxygenase from *Pseudomonas, Avena sativa*) enzyme, resistance to inhibitors of phytoene desaturase (PDS), resistance to photosystem II inhibiting herbicides (e.g., psbA), resistance to photosystem I inhibiting herbicides, resistance to protoporphyrinogen oxidase IX (PPO)-inhibiting herbicides (e.g., fomesafen, acifluorfen-sodium, oxyfluorfen, lactofen, fluthiacet-methyl, saflufenacil, flumioxazin, flumiclorac-pentyl, carfentrazone-ethyl, sulfentrazone), resistance to phenylurea herbicides (e.g., CYP76B1), 2,4-D resistance (e.g. aryloxy alkanoate dioxygenase or tfdA, AAD-1, AAD-12, or AAD-13), homogentisate solanesyltransferase (e.g. HST) dicamba-degrading enzymes (e.g. DMO), and others could be stacked alone or in multiple combinations to provide the ability to effectively control or prevent weed shifts and/or resistance to any herbicide of the aforementioned classes.

The above individualized herbicidal compositions may further comprise one or more soybean selective herbicides selected from the group consisting of acetochlor, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminocyclopyrachlor-potassium, aminocyclopyrachlor-methyl, aminopyralid, amitrole, ammoniumsulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clethodim, clodinafop, clodinafop-propargyl, clomazone, clomeprop, clopyralid, cloransulam, cloransulam-methyl, cumyluron, cyanamide, cyanazine, cycloate, cyclosulfamuron, cycloxydim, cyhalofop, cyhalofop-butyl, cyprazine, 2,4-D, 2,4-D-butotyl, -butyl, -dimethylammonium, -diolamin, -ethyl, 2-ethylhexyl, dazomet, -isobutyl, -isooctyl, -isopropylammonium, -potassium, -triisopropanolammonium and -trolamine, 2,4-DB, 2,4-DB-butyl, -dimethylammonium, isooctyl, -potassium and -sodium, daimuron (dymron), dalapon, n-decanol, desmedipham, detosyl-pyrazolate (DTP), dicamba, dichlobenil, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromid, dithiopyr, diuron, DNOC, endothal, EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, F-5231, i.e. N-{2-chloro-4-fluoro-5-[4-(3-fluoropropyl)-5-oxo-4,5-dihydro-1H-tetrazol-1-yl]phenyl}ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H, 3H)-dione, fenoxaprop, fenoxaprop-P, fenoxaprop-ethyl, fenoxaprop-P-ethyl, fenoxasulfone, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet (thiafluamide), flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyrsulfuron, flupyrsulfuron-methyl-sodium, fluridone, fluorochloridone, fluoroxypyr, fluoroxypyr-meptyl, flurtamone, fluthiacet, fluthiacet-methyl, fluthiamide, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium and -trimesium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl-(2,4-dichlorophenoxy)acetate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, kenacil, kinuron, MCPA, MCPA-butotyl, -dimethylammonium, -2-ethylhexyl, -isopropylammonium, -potassium and -sodium, MCPB, MCPB-methyl, -ethyl and -sodium, mecoprop, mecoprop-sodium, and -butotyl, mecoprop-P, mecoprop-P-butotyl, dimethylammonium, -2-ethylhexyl and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinat, monolinuron, monosulfuron, monosulfuron-ester, MT-128, i.e. 6-chloro-N-[(2E)-3-chloroprop-2-en-1-yl]-5-methyl-N-phenylpyridazin-3-amine, MT-5950, i.e. N-(3-chloro-4-isopropylphenyl)-2-methylpentan amide, NGGC-011, napropamide, NC-310, i.e. [5-(benzyloxy)-1-methyl-1H-pyrazol-4-yl](2,4-dichlorophenyl)methanone, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat dichloride, pebulate, pendimethalin, penoxsulam, pentachlorphenol, pentoxazone, pethoxamid, petroleum oils, phenmedipham, picloram, picolinafen, pinoxaden, piperophos, pretilachlor, primisulfuron, primisulfuron-methyl, prodiamine, prifluraline, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, sulcotrion, sulfentrazone, sulfometuron, sulfometuron-methyl, sulfosulfuron, SW-065, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trichloroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thiencarbazone, thiencarbazone-methyl, thifensulfuron, thifensulfuron-methyl, thiobencarb, topramezone, tralkoxydim, triafamone, tri-allate, triasulfuron, triaziflam, tribenuron, tribenuron-methyl, triclopyr, trietazine, trifloxysulfuron, trifloxysulfuron-sodium, trifluralin, triflusulfuron, triflusulfuron-methyl, tritosulfuron, urea sulfate, vernolate, ZJ-0862, i.e. 3,4-dichloro-N-{2-[(4,6-dimethoxypyrimidin-2-yl)oxy]benzyl}aniline; or plant growth regulators selected from the group consisting of zcibenzolar, acibenzolar-5-methyl, 5-aminolevulinic acid, ancymidol, 6-benzylaminopurine, Brassinolid, catechine, chlormequat chloride, cloprop, cyclanilide, 3-(cycloprop-1-enyl) propi-onic acid, daminozide, dazomet, n-decanol, dikegulac, dikegulac-sodium, endothal, endothal-dipotassium, -disodium, and mono(N,N-dimethylalkylammonium), ethephon, flumetralin, flurenol, flurenol-butyl, flurprimidol, forchlorfenuron, gibberellic acid, inabenfide, indol-3-acetic acid (IAA), 4-indol-3-ylbutyric acid, isoprothiolane, probenazole, jasmonic acid, maleic hydrazide, mepiquat chloride, 1-methylcyclopropene, methyl jasmonate, 2-(1-naphthyl)acetamide, 1-naphthylacetic acid, 2-naphthyloxyacetic acid, nitrophenolate-mixture, paclobutrazol, N-(2-phenylethyl)-beta-alanine, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P; or agrochemically acceptable salts or other forms thereof. For example, a combination of glyphosate, mesotrione and S-metolachlor may be applied to a soybean plant comprising a breeding stack containing in addition to SYT0H2, Glyphosate resistance e.g. EPSPS (e.g. GTS 40-3-2, MON89788, FG72, DP-356043-5).

The above individualized herbicidal compositions may also further comprise additional HPPD herbicides, including up to 2, 3, 4, 5, 6 or 7 HPPD inhibitor herbicides. Examples of 2 way combinations of HPPD inhibitor herbicides include: mesotrione+sulcotrione, mesotrione+tembotrione, mesotrione+bicyclopyrone, mesotrione+topramezone, mesotrione+isoxaflutole, mesotrione+pyrasulfatole, sulcotrione+tembotrione, sulcotrione+bicyclopyrone, sulcotrione+topramezone, sulcotrione+isoxaflutole, sulcotrione+pyrasulfatole, tembotrione+bicyclopyrone, tembotrione+topramezone, tembotrione+isoxaflutole, tembotrione+pyrasulfatole, bicyclopyrone+topramezone, bicyclopyrone+isoxaflutole, bicyclopyrone+pyrasulfatole, topramezone+isoxaflutole, topramezone+pyrasulfatole, isoxaflutole+pyrasulfatole. Examples of 3 way combinations of HPPD inhibitors include: mesotrione+sulcotrione+tembotrione, mesotrione+sulcotrione+topramezone, mesotrione+sulcotrione+bicyclopyrone, mesotrione+sulcotrione+isoxaflutole, mesotrione+sulcotrione+pyrasulfatole, mesotrione+tembotrione+topramezone, mesotrione+tembotrione+bicyclopyrone, mesotrione+tembotrione+isoxaflutole, mesotrione+tembotrione+pyrasulfatole, mesotrione+bicyclopyrone+topramezone, mesotrione+bicyclopyrone+isoxaflutole, mesotrione+bicyclopyrone+pyrasulfatole, mesotrione+topramezone+isoxaflutole, mesotrione+topramezone pyrasulfatole, mesotrione+isoxaflutole+pyrasulfatole, sulcotrione+tembotrione+bicyclopyrone, sulcotrione+tembotrione+topramezone, sulcotrione+tembotrione+isoxaflutole, sulcotrione+tembotrione+pyrasulfatole, sulcotrione+topramezone+bicyclopyrone, sulcotrione+topramezone+isoxaflutole, sulcotrione+topramezone+pyrasulfatole, sulcotrione+bicyclopyrone+isoxaflutole, sulcotrione+bicyclopyrone+pyrasulfatole, sulcotrione+isoxaflutole+pyrasulfatole, tembotrione+bicyclopyrone+topramezone, tembotrione+bicyclopyrone+isoxaflutole, tembotrione+bicyclopyrone+pyrasulfatole, tembotrione+topramezone+isoxaflutole, tembotrione+topramezone+pyrasulfatole, bicyclopyrone+topramezone+isoxaflutole, bicyclopyrone+topramezone+pyrasulfatole, topramezone+isoxafultole+pyrasulfatole.

EXAMPLES

Example 1. Preparation and Characterization of Soybean Event SYHT0H2

Binary vectors for soybean transformation were constructed with a promoter, such as a synthetic promoter containing a CaMV 35S and an FMV transcriptional enhancer and a synthetic TATA box driving the expression of an HPPD coding sequence followed by a NOS gene 3' terminator. A mutant HPPD gene derived from *Avena* HPPD was codon-optimized for soybean expression based upon the predicted amino acid sequence of the HPPD gene coding region. The mutant HPPD enzyme includes a deletion of a single alanine residue within positions 109-111 of the native *Avena sativa* HPPD enzyme. See U.S. Patent Application Publication No. 20100197503. Binary vector 15954 was constructed to comprise expression cassettes to express the mutant HPPD gene along with a selectable marker gene. See FIG. 1. The vector was constructed using a combination of methods well known to those skilled in the art such as overlap PCR, DNA synthesis, restriction fragment subcloning and ligation.

The abbreviations used in FIG. 1 (vector 15954) are defined as follows:

cAvH PP D-03
 Start: 1036 End: 2355
 Soybean codon optimized Oat HPPD gene encoding SEQ ID NO 14
cPAT-03-01
 Start: 3178 End: 3729
 PAT Hoescht A02774 synthetic *S. viridochromogenes*, plant codons; identical to Q57146 phosphinothricin acetyl transferase protein.
cPAT-03-02
 Start: 4761 End: 5312
 PAT Q57146 *S. viridochromogenes* phosphinothricin acetyl transferase protein, cPAT-03-01 DNA, but mutate BamH1, Bgl2 sites
cSpec-03
 Start: 6045 End: 6833
 streptomycin adenylyltransferase; from Tn7 (aadA)
cVirG-01
 Start: 7133 End: 7858
 Virulence G gene from *Agrobacterium tumefaciens* (virGN54D, containing TTG start codon) virGN54D came from pAD1289 described in Hansen et al. 1994, PROC. NATL. ACAD. SCI. U.S.A 91:7603-7607
cRepA-01
 Start: 788 End: 8961
 RepA, pVS 1 replication protein with A to G at nt735
eTMV-02
 Start: 965 End: 1032 (Complementary)
 Tobacco mosaic virus (TMV_Omega 5'UTR leader seq thought to enhance expression.
 EMBL: TOTMV6
e35S-05
 Start: 608 End: 900 (Complementary)
 Cauliflower mosaic virus 35S enhancer region with C to T & C to A by changes.
eFMV-03
 Start: 408 End: 601 (Complementary)
 Figwort mosaic virus enhancer.
bNRB-05
 Start: 4 End: 259 (Complementary)
 Right border region of T-DNA of *Agrobacterium tumefaciens* nopaline ti-plasmid.
bNRB-01-01
 Start: 101 End: 125 (Complementary)
 Right Border Repeat of T-DNA of *Agrobacterium tumefaciens* nopaline ti-plasmid.
bNLB-03
 Start: 5636 End: 5765 (Complementary)
 Left border region of T-DNA from *Agrobacterium tumefaciens* nopaline ti-plasmid.
 (Zambryski et al. 1980, Science, 209:1385-1391) EMBL no: J01825.
bNLB-01-01
 Start: 5671 End: 5695 (Complementary)
 25 bp Left border region of T-DNA of *Agrobacterium tumefaciens* nopaline ti-plasmid.
pr35S-04-01
 Start: 2633 End: 3153
 35S promoter; map originally defined promoter as 641 bp long; no exact match found in literature (LF July 2004)
prCMP-06
 Start: 4024 End: 4677
 Cestrum Yellow leaf curl virus promoter plus leader sequence. Not full-length transcript promoter. Basepair 528 was changed from G to C to remove an internal RsrII site.
oVS1-02
 Start: 9004 End: 9408
 origin of replication and partitioning region from plasmid pVS 1 of *Pseudomonas* (Itoh et al. 1984, Plasmid 11: 206-220); similar to GenBank Accession Number U10487; serves as origin of replication in *Agrobacterium tumefaciens* host
oCOLE-06
 Start: 10086 End: 10892 (Complementary)
 ColE1 origin of replication functional in *E. coli*
tNOS-05-01
 Start: 2372 End: 2624 (Complementary)
 NOS terminator: 3'UTR of the nopaline synthase gene
tNOS-05-01
 Start: 3763 End: 4015
 NOS terminator: 3'UTR of the nopaline synthase gene
tNOS-05-01
 Start: 5341 End: 5593
 NOS terminator: 3'UTR of the nopaline synthase gene Soybean plant material can be suitably transformed and fertile plants regenerated by many methods which are well known to one of skill in the art. For example, fertile morphologically normal transgenic soybean plants may be obtained by: 1) production of somatic embryogenic tissue from, e.g., immature cotyledon, hypocotyl or other suitable tissue; 2) transformation by particle bombardment or infection with *Agrobacterium*; and 3) regeneration of plants. In one example, as described in U.S. Pat. No. 5,024,944, cotyledon tissue is excised from immature embryos of soybean, optionally with the embryonic axis removed, and cultured on hormone-containing medium so as to form somatic embryogenic plant material. This material is transformed using, for example, direct DNA methods, DNA coated microprojectile bombardment or infection with *Agrobacterium*, cultured on a suitable selection medium and regenerated, optionally also in the continued presence of selecting agent, into fertile transgenic soybean plants. Selection agents may be antibiotics such as kanamycin, hygromycin, or herbicides such as an HPPD inhibitor, phosphinothricin, or glyphosate or, alternatively, selection may be based upon expression of a visualisable marker gene such as GUS. Target tissues for transformation include meristematic tissue, somaclonal embryogenic tissue, and flower or flower-forming tissue. Other examples of soybean transformation include physical DNA delivery methods, such as particle bombardment (see e.g., Finer & McMullen, *In Vitro Cell Dev. Biol.*, 1991, 27P:175-182; McCabe et al., *Bio/technol-* ogy, 1998, 6:923-926), whisker (Khalafalla et al., *African J. of Biotechnology,* 2006, 5:1594-1599), aerosol bean injection (U.S. Pat. No. 7,001,754), or by *Agrobacterium*-mediated delivery methods (Hinchee et al., *Bio/Technology,* 1988, 6:915-922; U.S. Pat. No. 7,002,058; U.S. Patent Application Publication Nos. 20040034889 and 20080229447; Paz et al., *Plant Cell Report,* 2006, 25:206-213).

Soybean transgenic plants can be generated with the above described binary vector 15954 containing a mutant HPPD gene using any available transformation method. Optionally, the HPPD gene can provide the means of selection and identification of transgenic tissue. For example, a vector was used to transform immature seed targets as described to generate transgenic HPPD soybean plants directly using HPPD inhibitor, such as mesotrione, as selection agent (see U.S. Patent Application Publication No. 20080229447). Optionally, an HPPD gene can be present in the polynucleotide alongside other sequences which provide additional means of selection/identification of transformed tissue including, for example, the known genes which provide resistance to kanamycin, hygromycin, phosphinothricin, butafenacil, or glyphosate. For example, different binary vectors containing PAT or EPSPS selectable marker genes are known in the art (see e.g., U.S. Patent Application Publication No. 20080229447). Alternatively, selectable marker sequences may be present on separate polynucleotides and a process of, for example, co-transformation and co-selection is used. A scorable marker gene such as GU.S. may also be used to identify transformed tissue.

T0 plants were taken from tissue culture to the greenhouse where they were transplanted into water-saturated soil (REDI-EARTH® Plug and Seedling Mix, Sun Gro Horticulture, Bellevue, Wash., or Fafard Germinating Mix) mixed with 1% granular MARATHON® (Olympic Horticultural Products, Co., Mainland, Pa.) at 5-10 g/gal soil in 2" square pots. The plants were covered with humidity domes and placed in a Conviron chamber (Pembina, N. Dak.) with the following environmental conditions: 24° C. day; 20° C. night; 16-23 hours light-1-8 hours dark photoperiod; 80% relative humidity.

After plants became established in the soil and new growth appeared (~1-2 weeks), plants were sampled and tested for the presence of desired transgene by TAQMAN® analysis using appropriate probes for the HPPD genes, or promoters (for example prCMP). Positive plants were transplanted into 4" square pots containing Fafard #3 soil. Sierra 17-6-12 slow release fertilizer was incorporated into the soil at the recommended rate. The plants were then relocated into a standard greenhouse to acclimatize (~1 week). The environmental conditions were: 27° C. day; 21° C. night; 14 hour photoperiod (with supplemental light); ambient humidity. After acclimatizing (~1 week), the plants were sampled and tested in detail for the presence and copy number of inserted transgenes. Transgenic soybean plants were grown to maturity for T1 seed production. T1 plants were grown up, and after TAQMAN® analysis, homozygous plants were grown for seed production. Transgenic seeds and progeny plants were used to further evaluate their herbicide tolerance performance and molecular characteristics. From a population of about 90 transformants, event SYHT0H2 showed a high level of mesotrione tolerance.

Event SYHT0H2 insert and flanking sequences were obtained by a combination of two methods; lambda library generation and GENOMEWALKER™ (Clontech). Sequencing of event SYHT0H2 was carried out using the Sanger method of DNA sequencing. The sequence analysis was done using the sequence analysis program SEQUENCHER® (Gene Codes Corporation). Genomic DNA from soybean event SYHT0H2 was isolated for the purpose of generating a lamda library by isolating genomic DNA and restriction digesting with the restriction enzymes BamHI or EcoRI and KpnI to completion as described by the restriction enzyme supplier (NEB). Partial digest of the genomic DNA was completed using BfuCI at 0.15 U/µg DNA at 37° C. Samples were taken out at 2, 4, 6, 8, and 10 minutes after addition of enzyme. Samples were pooled for gel loading. Digested samples were loaded in a 1% Agarose TAE gel and run overnight at 20V. Fractions were isolated for each digest, BfuCI; 2-4 kb, BamHI; 0.7-3.5 kb and EcoRI-KpnI; 3-6 kb. DNA was recovered from gel using the QIAQUICK® Gel Extraction kit as described by the supplier (Qiagen). Isolated fractions were ligated to Lambda Zap Express vector (Stratagene) cut with either BamHI or EcoRI-KpnI. Ligations were setup using a ratio 1000 ng of vector to 100 ng of insert in 10 µl volume with 200 U ligase incubated overnight at 6° C.

Libraries were packaged using Maxplaq as described by the supplier (Epicentre). Libraries were titered using XL-1MRA (Stratagene) cells. Cells were grown up for 6 hours at 37° C. in NZY broth plus 0.2% maltose. Cells were centrifuged at 4K and resuspended in SM buffer (Stratagene). Phage were diluted 1/100 in SM buffer and 10 µl was mixed with 100 µl cells, incubated at 37° C. for 15 minutes, 3.5 ml NZY Top agarose (50° C.) was added, mixed by inversion and spread across L-agar plates, which were then incubated overnight at 37° C.

The library was screened for individual clones which contained the heterologous inserted sequence. The bacterial cells used for plating the library were XL-1MRA purchased from Stratagene. The XL-1MRA cells were grown in NZY broth plus 0.2% maltose 6 hours before use. Infected bacterial cells were plated onto L-agar plates prepared by pouring L-agar onto 25×150 mm plates pre-warmed at 37° C. before use. Bacterial cells were collected by centrifuging at 4K and resuspending the cells in SM buffer (Stratagene). 300 µl of bacterial cells and 50,000 phage were combined in a 15 ml tube (Fisher Scientific) and incubated at 37° C. for 15 minutes. 9 ml of NZY Top agarose was added and mixed by inversion, and the resulting mixture was spread across the surface of large plates to maintain a smooth surface. 10 plates per library were constructed for a total of 500,000 phage screened per library. Innoculated plates were incubated overnight at 37° C. The following day, the plants were removed and placed at 4° C. for at least 1 hour.

The plaques formed in the inoculated plates were transferred to Hybond NX (GE Amersham) membranes by placing the membrane on the surface of the plate. After the membrane became uniformly wet, it was allowed to incubate for 2 minutes. The orientation of the plate was marked with a needle and India ink by punching needle with ink on it into membrane and agar at three different spots. The marked membrane was removed from the plate and placed membrane phage side up on Whatman paper soaked with 0.5 M NaOH for 5 minutes (Bio-Rad method) followed by transfer to Whatman paper soaked in 2×SSC then air dried, and the DNA and membrane were cross-linked using a Stratalinker (Stratagene) at 160 mJ.

To identify the lambda phage clones which contained the heterologous inserted DNA, the filters from above were probed as follows: filters were pre-hybridized in 7% SDS, 250 mM sodium phosphate pH 7.0, 1% BSA at 62° C. for 4 hours. The pre-hybridization solution was replaced with rest hybridization solution before addition of radioactive probe.

Probes were prepared by PCR with primers MT_SOY_F2 and MT_SOY_R3 using pSYN15764 as template:

P_MTSOY_F2
(SEQ ID NO: 25)
TTTTGTGGTCGTCACTGCGTT

P_MTSOY_R3
(SEQ ID NO: 26)
CAGGATATATTGTGGTGTAAACAAATTGACGCTTAGACAA

Reaction conditions were as follows: 1× Expand buffer, 200 uM dNTP, 50 ng template, 10 pM primers, 1.5 U Expand DNA Polymerase (Roche) in 50 µl reaction volume.

The cycling conditions were 35 cycles at [94° C., 30 seconds; 55° C., 30 seconds, 72° C., 2 minutes].

The amplified fragment was isolated on a 1% agarose-TAE gel. DNA was purified from agarose using QIAQUICK Gel extraction kit (QIAGEN). The probe was random prime labeled using the REDIPRIME™ II kit (GE Amersham) with radioactive dCT$^{32}$P. The probe was separated from unincorporated label using GE Amersham G-50 spin columns. The probe was heated for 5 minutes at 95° C. before addition to hybridization buffer. Hybridization proceeded overnight at 62° C. Filters were washed first with 2×SSC, 0.5% SDS for 30 minutes at 62° C., and then with 0.2×SSC, 0.2% SDS for 30 minutes at 62° C. Filters were wrapped in plastic wrap and exposed to Kodak Biomax XAR film for 16-24 hours at −80° C. with intensifying screens.

Positive spots were plugged with an 8 mm diameter plug and placed in 500 µl SM buffer plus 25 µl chloroform and allowed to elute overnight at 6 degrees C. Phage were diluted 1/500 in SM buffer for 2$^{nd}$ round screening. A total of 1000 pfu (plaque forming units) were screened in the 2$^{nd}$ round. The 2$^{nd}$ round screen replicates the process used for the primary screen. This is done for each positive clone identified in the primary screen. This process may be repeated until a single positive plaque is isolated.

Phage was converted to plasmid using the protocol described in the Zap Express Vector Kit manual (Stratagene). The isolated plasmids were sequenced and the sequence assembled using the program SEQUENCHER® (Gene Codes Corporation).

In addition to the sequencing method described above, the insertion site of the heterologous inserted polynucleotide sequence of soybean event SYHT0H2 was also sequence by using a BD GENOMEWALKER™ Universal Kit. Using the GENOMEWALKER™ kit, the left border 1 (LB1) flanking sequence for the SYHT0H2 event was recovered. As outlined in the kit instructions, genomic DNA from the soybean event SYHT0H2 was isolated and digested to completion by combining 8 µl DNA (~10 ng/µl), 1 µl 10×EcoRV buffer, and 1 µl EcoRV in a sterile microcentrifuge tube and incubating for 37° C. for overnight.

The EcoRV digested DNA was ligated to the BD GENOMEWALKER™ Adaptor as described in the manufacturer's directions. To amplify the DNA which contained the heterologous inserted polynucleotide sequence of soybean event SYHT0H2, two gene specific primers (GSP1 and GSP2) were designed based on sequence of the left border region of the 15954 transformation vector sequence. GSP2 is nested in a PCR product generated by the amplification of GSP1 and a primer designed based upon the sequence of the BD GENOMEWALKER™ Adaptor.

TABLE 4

| Primer Name | Primer sequence |
| --- | --- |
| GSP1/FlkSeq0027 | GAGTCCCGCAATTATACATTTAATACGCGATAGAA SEQ ID NO: 27 |
| GSP2/FlkSeq0005 | GGCCAGCATGGCCGTATCCGCAATGTGTT SEQ ID NO: 28 |

PCR amplicons were generated in two steps consisting of a primary PCR and secondary (nested) PCR according to the manufacturer's directions. The PCR products of the secondary PCR were sequenced.

The sequence information generated by both the lambda library sequence and the GENOMEWALKER™ sequencing were combined to generate the insertion site sequence of the soybean event SYTH0H2. The nucleotide sequence of the complete insert is set forth as SEQ ID NO: 9, and the nucleotide sequence of the insert flanked by genomic DNA is set forth as SEQ ID NO: 10. Additional nucleotide sequences that describe the LB2 and LB 1 junctions of the insert and flanking genomic DNA are set forth as SEQ ID NOs: 1-6 (see Table 1, page 3).

Example 2. Event-Specific PCR Analysis

Genomic DNA from *Glycine max* transformants was used as a template for PCR analysis in a TAQMAN® assay using the primer pairs shown in Table 5 and the cycling conditions shown in Table 6. A typical reaction mixture included 1× JUMPSTART™ READYMIX™, 300 nm Primer 1, 300 nm Primer 2, 100 nm probe, and about 30 ng template DNA in a total volume of 10 µl. For assay A1720, primer P10325 is in the insert and is used to amplify LB1 of the T-DNA insert while primer P12721 is in the genome at the insertion site. Assay A1720 generates a PCR product that is 66 bp long:

(SEQ ID NO: 24)
CGGGCGGCCAGCATGGCCGTATCCGCAATGTGTTATTAAGTTGTCTAA

ACCCTAAACCAATGGCAC.

For assay A1721, primer P10043 is in the insert and is used to detect LB2 of the T-DNA insert while primer P12723 is in the genome at the insertion site). Assay A1721 generates a PCR product that is 70 bp long:

(SEQ ID NO: 25)
GGATGAAGAGATGAGAGAACCATCACAGAATTGACGCTTAGACAACT

TAATAACACATTGCGGATACGGC.

TABLE 5

| Assay ID | Primer/ probe ID | Sequence (5'-to-3') |
| --- | --- | --- |
| A1720 | P10325 (primer) | CGGGCGGCCAGCAT (SEQ ID NO: 11) |
|  | P12721 (primer) | GTGCCATTGGTTTAGGGTTTAGAC (SEQ ID NO: 12) |
|  | P12722 (probe) | FAM-ATCCGCAATGTGTTATTAA-MGB* (SEQ ID NO: 13) |
| A1721 | P10043 (primer) | GCCGTATCCGCAATGTGTTA (SEQ ID NO: 14) |
|  | P12723 (primer) | GGATGAAGAGATGAGAGAACCATCA (SEQ ID NO: 15) |

TABLE 5-continued

| Assay ID | Primer/<br>probe ID | Sequence (5'-to-3') |
|---|---|---|
| | P12724<br>(probe) | FAM-TAAGTTGTCTAAGCGTCAATT-MGB*<br>(SEQ ID NO: 16) |

FAM, 6-carboxyfluorescein

MGB, dihydrocyclopyrroloindole tripeptide minor groove binder

*BGB-labeled probe may also be used

TABLE 6

| Cycle | Step | Temperature<br>(° C.) | Time | Repeated<br>Cycles |
|---|---|---|---|---|
| A | 1 | 95 | 10 minutes | — |
| B | 1 | 95 | 15 seconds | 40 |
| B | 2 | 60 | 1 minute | 40 |

Alternatively, genomic DNA from *Glycine max* transformants was used as a template for gel based assays using the primer pairs shown in Table 7 and the cycling conditions shown in Table 8. A typical reaction mixture included 1× JUMPSTART™ READYMIX™, 10 µM Primer 1, 10 µM Primer 2, 1 µL of 10 ng/µL genomic template DNA in a total volume of 20 µl.

TABLE 7

| Target | Primer 1<br>(T-DNA) | Primer 2 (genome) |
|---|---|---|
| SYHT0H2_LBFS_1 | FE0845<br>(SEQ ID NO: 17) | FE3427<br>(SEQ ID NO: 18) |
| SYHT0H2_LBFS_1 | FE0845<br>(SEQ ID NO: 17) | FE3443<br>(SEQ ID NO: 19) |
| SYHT0H2_LBFS_2 | FE0845<br>(SEQ ID NO: 17) | FE3429<br>(SEQ ID NO: 20) |
| SYHT0H2_LBFS_2 | FE0845<br>(SEQ ID NO: 17) | FE3442<br>(SEQ ID NO: 21) |

TABLE 8

| Cycle | Step | Temperature<br>(° C.) | Time | Repeated<br>Cycles |
|---|---|---|---|---|
| A | 1 | 94 | 3 minutes | — |
| B | 1 | 94 | 30 seconds | 35 |
| B | 2 | 58 | 30 seconds | 35 |
| B | 3 | 68 | 1 minutes | 35 |
| C | 1 | 68 | 7 minutes | — |
| D | 1 | 4 | 10 minutes | — |

Example 3. Field Efficacy of Event SYHT0H2

Event SYHT0H2 soybean plants were tested for efficacy against mesotrione in 5 locations in the United States. The non-transgenic soybean line Jack was used as a control. Soybean plants, both SYHT0H2 and Jack, were treated with 210 g ai/ha of mesotrione at the V2/V3 stage and then assessed for percentage of leaves showing injury at 4-7 days after treatment (DAT), 13-17 DAT, and 25-33 DAT. Results in Table 9 demonstrate the efficacy of 0H2 against mesotrione as compared against a control line.

TABLE 9

| | % Injury | | |
|---|---|---|---|
| Genotype | 4-7 DAT | 13-17 DAT | 25-33 DAT |
| Jack | 46.5 | 81 | 62.4 |
| SYHT0H2 | 13.2 | 4.7 | 0 |

SYHT0H2 soybean plants were tested for efficacy against glufosinate in 8 locations in the United States. The non-transgenic soybean line Jack was used as a control. Soybean plants, both SYHT0H2 and Jack, were treated with 900 g ai/ha of glufosinate at the V2/V3 stage and then a second treatment at the V5-V6 stage. They were then assessed for percentage of leaves showing injury at 4-8 days after treatment (DAT), 13-20 DAT, and 26-35 DAT. Results in Table 10 demonstrate the efficacy of SYHT0H2 against glufosinate as compared against a control line.

TABLE 10

| | % Injury | | |
|---|---|---|---|
| Genotype | 4-8 DAT | 13-20 DAT | 26-35 DAT |
| Jack | 100 | 100 | 100 |
| SYHT0H2 | 9 | 5 | 0 |

Example 4. Markers for Mapping and Breeding Selection

The flanking sequence from LB2 (SEQ ID NO: 7) or flanking sequence of LB 1 (SEQ ID NO: 8) of the insert SYHT0H2 were aligned against the 8× Soybean Genome Database (i.e., the "Phytozome" Database administered by the Joint Genome Institute and the Center for Integrative Genomics available through the World Wide Web; see also Schmutz et al. (2010) *Nature* 463:178-183) using the Basic Local Alignment Search Tool (BLAST; Altschul et al., *J. Mol. Biol.*, 1990, 215:403-410; Altschul et al., *Nucleic Acids Res.*, 1997, 25:3389-3402), also available on the internet. LB2 aligned with chromosome number 8 (linkage group A2) from nucleotide 9,905,212 to 9,905,310. LB1 aligned with chromosome 8 (linkage group A2) from nucleotide 9,905, 326 to 9,905,788. The physical positions were then compared to that of markers listed in the Soybean Consensus Map 4.0 (Hyten et al. *Crop Sci.*, 2010, 50:960-968). The centiMorgan position of the nearest marker was identified and all markers within 10 centiMorgans are listed in Table 9. This data demonstrates that the insertion of heterologous polynucleotide sequence in event SYT0H2 occurred on soybean chromosome 8 at a position between base pairs 9,905,310 and 9,905,326, which corresponds to the sequence between nucleotides 99 and 116 of SEQ ID NO: 24. Upon insertion of the heterologous sequence containing the HPPD sequence, 16 base pairs of the genomic sequence are deleted, which correspond to nucleotides 100-115 of SEQ ID NO: 24.

Event SYHT0H2 is introduced in a soybean plant using one or more of the publicly available markers identified in Table 11 and conventional breeding techniques. Event SYHT0H2 is closest to molecular marker BARC-65571-19573 and is between molecular markers BARC-65571-19573 and BARC-43119-08535. Breeding approaches and techniques are well known in the art. See, e.g., Fehr, in *Breeding Methods for Cultivar Development*, 1987, Wilcos, J. (ed.), American Society of Agronomy, Madison, Wis.;

Welsh J. R., *Fundamentals of Plant Genetics and Breeding*, John Wiley & Sons, NY (1981); Wood D. R. (Ed.), *Crop Breeding*, American Society of Agronomy Madison, Wis. (1983); Mayo O., *The Theory of Plant Breeding*, Second Edition, Clarendon Press, Oxford (1987); Singh, D. P., *Breeding for Resistance to Diseases and Insect Pests*, Springer-Verlag, NY (1986); and Wricke and Weber, *Quantitative Genetics and Selection Plant Breeding*, Walter de Gruyter and Co., Berlin (1986).

TABLE 11

| Public Marker Name | LG | cM | Type |
|---|---|---|---|
| Sat_400 | A2 | 43.8 | SSR |
| BARC-032503-08989 | A2 | 44.5 | SNP |
| BARC-045047-08867 | A2 | 45.6 | SNP |
| BARC-028361-05839 | A2 | 45.7 | SNP |
| BARC-028361-05840 | A2 | 45.7 | SNP |
| BARC-028361-05841 | A2 | 45.7 | SNP |
| BARC-028361-05842 | A2 | 45.7 | SNP |
| BARC-028361-05843 | A2 | 45.7 | SNP |
| BARC-028361-05844 | A2 | 45.7 | SNP |
| BARC-028361-05845 | A2 | 45.7 | SNP |
| BARC-028361-05846 | A2 | 45.7 | SNP |
| BARC-028361-05847 | A2 | 45.7 | SNP |
| BARC-028361-05848 | A2 | 45.7 | SNP |
| BARC-028361-05849 | A2 | 45.7 | SNP |
| BARC-028361-05850 | A2 | 45.7 | SNP |
| BARC-028361-05851 | A2 | 45.7 | SNP |
| BARC-018419-02910 | A2 | 46.0 | SNP |
| BARC-018419-02911 | A2 | 46.0 | SNP |
| BARC-018419-02912 | A2 | 46.0 | SNP |
| BARC-016861-02355 | A2 | 46.1 | SNP |
| Satt632 | A2 | 46.3 | SSR |
| Sat_157 | A2 | 46.4 | SSR |
| BARC-021329-04038 | A2 | 46.4 | SNP |
| BARC-021329-04039 | A2 | 46.4 | SNP |
| BARC-016685-03321 | A2 | 46.4 | SNP |
| Sat_162 | A2 | 46.6 | SSR |
| BARC-018023-02498 | A2 | 46.7 | SNP |
| BARC-018023-02499 | A2 | 46.7 | SNP |
| BARC-028309-05824 | A2 | 46.8 | SNP |
| BARC-028309-05825 | A2 | 46.8 | SNP |
| BARC-028309-05826 | A2 | 46.8 | SNP |
| BARC-040339-07714 | A2 | 47.0 | SNP |
| BARC-040339-07715 | A2 | 47.0 | SNP |
| BARC-030485-06876 | A2 | 47.2 | SNP |
| BARC-050171-09440 | A2 | 47.3 | SNP |
| BARC-012193-01743 | A2 | 47.6 | SNP |
| BARC-010097-00518 | A2 | 47.6 | SNP |
| Sat_215 | A2 | 47.9 | SSR |
| BARC-059853-16139 | A2 | 48.0 | SNP |
| BARC-015419-01822 | A2 | 48.2 | SNP |
| BARC-027690-06633 | A2 | 49.0 | SNP |
| BARC-021831-04219 | A2 | 49.0 | SNP |
| BARC-021831-04220 | A2 | 49.0 | SNP |
| BARC-027726-06646 | A2 | 49.3 | SNP |
| BARC-057257-14650 | A2 | 49.3 | SNP |
| Satt187 | A2 | 49.9 | SSR |
| BARC-027618-06620 | A2 | 50.0 | SNP |
| BARC-027618-06621 | A2 | 50.0 | SNP |
| BARC-027618-06622 | A2 | 50.0 | SNP |
| BARC-027618-06623 | A2 | 50.0 | SNP |
| BARC-027618-06624 | A2 | 50.0 | SNP |
| BARC-026091-05255 | A2 | 50.4 | SNP |
| Sat_212 | A2 | 50.7 | SSR |
| BARC-065571-19573 | A2 | 51.3 | SNP |
| BARC-040029-07638 | A2 | 52.2 | SNP |
| BARC-040029-07639 | A2 | 52.2 | SNP |
| BARC-040029-07640 | A2 | 52.2 | SNP |
| BARC-043119-08535 | A2 | 52.3 | SNP |
| BARC-038631-07266 | A2 | 52.4 | SNP |
| BARC-053809-12037 | A2 | 52.4 | SNP |
| BARC-018083-02511 | A2 | 52.5 | SNP |
| BARC-018083-02512 | A2 | 52.5 | SNP |
| BARC-013857-01257 | A2 | 52.6 | SNP |
| BARC-013857-01258 | A2 | 52.6 | SNP |
| BARC-017983-02492 | A2 | 53.0 | SNP |
| BARC-039145-07456 | A2 | 53.1 | SNP |
| BARC-039145-07457 | A2 | 53.1 | SNP |
| BARC-029007-06050 | A2 | 53.4 | SNP |
| Satt424 | A2 | 53.6 | SSR |
| BARC-020307-04547 | A2 | 55.1 | SNP |
| BARC-020307-04548 | A2 | 55.1 | SNP |
| BARC-020307-04549 | A2 | 55.1 | SNP |
| BARC-020307-04550 | A2 | 55.1 | SNP |
| BARC-020307-04551 | A2 | 55.1 | SNP |
| BARC-045081-08872 | A2 | 55.1 | SNP |
| BARC-019749-04349 | A2 | 56.4 | SNP |
| BARC-019749-04350 | A2 | 56.4 | SNP |
| BARC-019749-04351 | A2 | 56.4 | SNP |
| BARC-019749-04352 | A2 | 56.4 | SNP |
| BARC-019749-04353 | A2 | 56.4 | SNP |
| BARC-019749-04354 | A2 | 56.4 | SNP |
| BARC-019749-04355 | A2 | 56.4 | SNP |
| BARC-019749-04356 | A2 | 56.4 | SNP |
| BARC-019749-04357 | A2 | 56.4 | SNP |
| BARC-019749-04358 | A2 | 56.4 | SNP |
| BARC-019749-04359 | A2 | 56.4 | SNP |
| BARC-019749-04360 | A2 | 56.4 | SNP |
| BARC-019749-04361 | A2 | 56.4 | SNP |
| BARC-013587-01167 | A2 | 56.6 | SNP |
| BARC-013587-01169 | A2 | 56.6 | SNP |
| BARC-013587-01170 | A2 | 56.6 | SNP |
| BARC-029671-06301 | A2 | 56.7 | SNP |
| BARC-029671-06302 | A2 | 56.7 | SNP |
| BARC-029671-06303 | A2 | 56.7 | SNP |
| BARC-029671-06304 | A2 | 56.7 | SNP |
| BARC-029671-06305 | A2 | 56.7 | SNP |
| BARC-029671-06306 | A2 | 56.7 | SNP |
| BARC-029671-06307 | A2 | 56.7 | SNP |
| BARC-029671-06308 | A2 | 56.7 | SNP |
| BARC-029671-06309 | A2 | 56.7 | SNP |
| BARC-029671-06310 | A2 | 56.7 | SNP |
| BARC-029671-06311 | A2 | 56.7 | SNP |
| BARC-039393-07313 | A2 | 56.7 | SNP |
| BARC-027614-06615 | A2 | 56.9 | SNP |
| BARC-027614-06616 | A2 | 56.9 | SNP |
| BARC-027614-06617 | A2 | 56.9 | SNP |
| BARC-027614-06618 | A2 | 56.9 | SNP |
| BARC-027614-06619 | A2 | 56.9 | SNP |
| BARC-016661-02162 | A2 | 57.2 | SNP |
| BARC-016661-02163 | A2 | 57.2 | SNP |
| BARC-044327-08668 | A2 | 58.2 | SNP |
| BARC-044869-08827 | A2 | 58.9 | SNP |
| BARC-044869-08828 | A2 | 58.9 | SNP |
| BARC-018941-03041 | A2 | 59.3 | SNP |
| BARC-018941-03042 | A2 | 59.3 | SNP |
| BARC-030759-06940 | A2 | 60.1 | SNP |
| BARC-030759-06941 | A2 | 60.1 | SNP |
| BARC-030759-06942 | A2 | 60.1 | SNP |
| BARC-014665-01611 | A2 | 61.1 | SNP |
| BARC-014665-01612 | A2 | 61.1 | SNP |
| BARC-014665-01613 | A2 | 61.1 | SNP |
| BARC-014665-01614 | A2 | 61.1 | SNP |
| BARC-014665-01615 | A2 | 61.1 | SNP |
| BARC-014665-01616 | A2 | 61.1 | SNP |
| BARC-014665-01617 | A2 | 61.1 | SNP |
| BARC-014665-01618 | A2 | 61.1 | SNP |
| BARC-029865-06449 | A2 | 61.5 | SNP |
| BARC-044217-08646 | A2 | 61.9 | SNP |
| BARC-013567-01162 | A2 | 62.2 | SNP |
| BARC-013567-01163 | A2 | 62.2 | SNP |

Example 5. Use of Event SYHT0H2 Insertion Site for Targeted Integration in Soybean The event SYHT0H2 flanking sequences disclosed in SEQ ID NO: 7 and SEQ ID NO: 8 are used to search soybean genome databases. Identical matches to both flanking sequences are identified on a BAC clone and molecular markers at the location are identified. Additional markers are developed and used for fine mapping of the insertion site.

Consistent agronomic performance of the transgene of event SYHT0H2 over several generations under field conditions, the integration site of event SYHT0H2 provides a useful genomic locus for integration of transgenes of interest other than the mutant HPPD enzyme of event SYHT0H2. Such targeted integration overcomes the problems with so-called "positions effects," and the risk of creating a mutation in the genome upon integration of the transgene into the host. Further advantages of such targeted integration include, but are not limited to, reducing the large number of transformation events that must be screened and tested before obtaining a transgenic plant that exhibits the desired level of transgene expression without also exhibiting abnormalities resulting from the inadvertent insertion of the transgene into an important locus in the host genome. Moreover, such targeted integration allows for stacking transgenes rendering the breeding of elite plant lines with both genes more efficient.

Using the above disclosed teaching, the skilled person is able to use methods known in the art to target transgenes to the same insertion site as that in SYHT0H2 or to a site in close proximity to the insertion site in SYHT0H2. One such method is disclosed in U.S. Patent Application Publication No. 20060253918, herein incorporated by reference in its entirety. Briefly, up to 20 Kb of the genomic sequence flanking 5' to the insertion site (e.g., SEQ ID NO: 7, genomic sequences comprising SEQ ID NO: 7, and genomic sequences homologous to SEQ ID NO: 7) and up to 20 Kb of the genomic sequence flanking 3' to the insertion site (e.g., SEQ ID NO: 8, genomic sequences comprising SEQ ID NO: 8, and genomic sequences homologous to SEQ ID NO: 8) are used to flank the gene or genes of interest that are intended to be inserted via homologous recombination, which site of integration is at or near the site of event SYHT0H2. These sequences can be further flanked by T-DNA border repeats such as the left border (LB) and right border (RB) repeat sequences and other booster sequences for enhancing T-DNA delivery efficiency. The gene or genes of interest can be placed exactly as in the SYHT0H2 insertion site or can be placed anywhere within the 20 Kb regions around the SYHT0H2 insertion sites to confer consistent level of transgene expression without detrimental effects on the plant. The DNA vectors containing the gene or genes of interest and flanking sequences can be delivered into plant cells via one of the several methods known to those skilled in the art, including but not limited to *Agrobacterium*-mediated transformation. The insertion of the DNA vector into the SYHT0H2 target site can be further enhanced by one of the several methods, including but not limited to the co-expression or up-regulation of recombination enhancing genes or down-regulation of endogenous recombination suppression genes. Furthermore, it is known in the art that cleavage of specific sequences in the genome can be used to increase homologous recombination frequency, therefore insertion into the SYHT0H2 insertion site and its flanking regions can be enhanced by expression of natural or designed sequence-specific endonucleases for cleaving these sequences.

Example 7. Use of Event SYHT0H2 Insertion Site and Flanking Sequences for Stabilization of Gene Expression The genomic sequences flanking the SYHT0H2 insertion site may also be used to stabilize expression of other gene(s) of interest when inserted as a transgene in genomic locations in soybean other than the integration site of SYHT0H2 as well as in other crops. Specifically, up to 20 Kb of the genomic sequence flanking 5' to the insertion site (e.g., SEQ ID NO: 7, genomic sequences comprising SEQ ID NO: 7, and genomic sequences homologous to SEQ ID NO: 7) and up to 20 Kb of the genomic sequence flanking 3' to the insertion site (e.g., SEQ ID NO: 8, genomic sequences comprising SEQ ID NO: 8, and genomic sequences homologous to SEQ ID NO: 8) are used to flank the gene or genes of interest that are intended to be inserted into the genome of plants. These sequences can be further flanked by T-DNA border repeats such as the left border (LB) and right border (RB) repeat sequences and other booster sequences for enhancing T-DNA delivery efficiency. The gene or genes of interest can be placed exactly as in the SYHT0H2 insertion site or can be placed anywhere within the 20 Kb regions on either side of the SYHT0H2 insertion site to confer a consistent level of transgene expression. The DNA vectors containing the gene or genes of interest and SYHT0H2 insertion site flanking sequence can be delivered into plant cells via one of the several methods known to those skilled in the art, including but not limited to protoplast transformation, biolistic bombardment and *Agrobacterium*-mediated transformation. The delivered DNA can be integrated randomly into a plant genome or can also be present as part of the independently segregating genetic units such as artificial chromosome or mini-chromosome. The DNA vectors containing the gene(s) of interest and the SYHT0H2 insertion site flanking sequences can be delivered into plant cells. Thus, by surrounding a gene or genes of interest with the genomic sequence flanking the SYHT0H2 insertion site, the expression of such genes are stabilized in a transgenic host plant, including both monocot and dicot plants.

What is claimed is:

1. A seed of a transgenic soybean plant comprising herbicide tolerance event SYHT0H2, wherein said seed comprises herbicide tolerance event SYHT0H2 and a representative sample of said seed comprising said event has been deposited under ATCC Accession No. PTA-11226.

2. A transgenic herbicide tolerance event SYHT0H2 soybean plant, cells or tissues thereof comprising a nucleic acid molecule comprising nucleotides 793-8764 of SEQ ID NO: 10.

3. A seed of a transgenic soybean plant of claim 2, wherein said seed comprises herbicide tolerance event SYHT0H2 and further comprises one or more additional regions encoding a polypeptide providing the plant with resistance or tolerance to one or more additional herbicides, or one or more insects, fungal, bacterial and/or viral infections.

4. The transgenic soybean seed of claim 3, wherein the one or more additional regions encode a polypeptide providing the plant with resistance or tolerance to one or more additional herbicides selected from group consisting of: glyphosate, glufosinate, dicamba, 2,4-D, phenoxy auxin herbicides, PPO herbicides, aryloxyphenoxypropionate herbicides, imidazolinone, sulfonyl urea, ametryne, triazine herbicides and metribuzin.

5. The transgenic soybean seed of claim 3, wherein the one or more additional regions encode a polypeptide providing the plant with resistance or tolerance to one or more additional herbicides, the polypeptide being selected from the group consisting of: a glyphosate tolerant 5-enol-pyruvylshikimate-3-phosphate synthase (EPSPS), glyphosate N-acetyl transferase (GAT), herbicide tolerant 4-hydroxyphenylpyruvyldioxgenase (HPPD), phosphinothricin actetyl transferase (PAT), cytochrome P450, glutathione S-transferase (GST), herbicide tolerant acetyl-COA-carboxylase (ACCase), herbicide tolerant acetolactate synthase (ALS), herbicide tolerant protoporphyrinogen oxidase (PPO), bromoxynil nitrilase, herbicide tolerant phytoene desaturase, aryloxyalkanoate dioxygenase, homogentisate solanesyltransferase (HST) and dicamba degrading enzymes.

6. The transgenic soybean seed of claim 3, wherein the plant comprises resistance to a combination of an HPPD inhibitor, glyphosate, glufosinate, and dicamba herbicides, wherein the HPPD inhibitor is selected from the group consisting of isoxaflutole, bicyclopyrone, mesotrione, sulcotrione, tembotrione, topramezone pyrasulfatole; and wherein the ALS inhibitor is selected from the group consisting of prosulfuron, primisulfuron, triasulfuron, bensulfuron, nicosulfuron, rimsulfuron, primisulfuron, thifensulfuron, foramsulfuron, chlorsulfuron, halosulfuron, imazaquin, imazapic, imazapyr, imazethapyr, imazamox, iodosulfuron, metsulfuron, mesosulfuron sulfosulfuron trifloxysulfuron tribenuron methyl, thiazopyr, diclosulam, cloransulam-methyl, flucarbazone, flumetsulam, thiencarbazone, and chlorimuron-ethyl.

7. The soybean plant of claim 2, wherein the plant further comprise one or more additional regions encoding a polypeptide providing the plant with resistance or tolerance to one or more additional herbicides, one or more insects, or one or more fungal, bacterial and/or viral infections.

8. A method of weed control comprising applying a combination of at least two herbicides corresponding to the regions encoded by a polypeptide capable of providing the plant with resistance or tolerance to one or more additional herbicides on a field of transgenic soybean plants of claim 2, wherein the transgenic soybean plants comprise herbicide tolerance event SYHT0H2, wherein a representative sample of seed comprising said event has been deposited under ATCC Accession No. PTA-11226, or further comprise one or more additional regions encoding a polypeptide capable of providing the plant with resistance or tolerance to one or more additional herbicides, or one or more insects, fungal, bacterial, and/or viral infections.

9. The method of claim 8, wherein the application is (i) tank mix application, (ii) subsequent sprays, or (iii) pre-mix application.

10. A method of producing a soybean plant resistant to one or both of: an HPPD inhibitor and glufosinate, comprising the steps of: a. crossing a first soybean plant comprising event SYHT0H2, wherein a representative seed comprising said event has been deposited under ATCC Accession No. PTA-11226; and b. selecting at least a first progeny plant that comprises event SYHT0H2 and is resistant to one or both of the following: an HPPD inhibitor and glufosinate.

11. The method of claim 10, further comprising the steps of:
  a. selfing the first progeny plant to produce second generation progeny plants; and
  b. selecting at least a first plant homozygous for event SYHT0H2.

12. A method of controlling weeds at a location comprising soybean plants and weeds, wherein the soybean plants comprise event SYHT0H2, wherein a representative seed comprising said event has been deposited under ATCC Accession No. PTA-11226, and wherein the method comprises applying to the location a weed controlling amount of an herbicidal composition comprising one or more HPPD inhibitors.

13. The method of claim 12, wherein the one or more HPPD inhibitors is selected from the group consisting of bicyclopyrone, mesotrione, sulcotrione, topramezone, tembotrione, pyrasulfatole and isoxaflutole.

14. A method of controlling weeds at a location comprising soybean plants and weeds, said method comprising: a. growing soybean plants comprising event SYHT0H2, wherein a representative seed comprising said event has been deposited under ATCC Accession No. PTA-11226, or further comprising one or more additional regions encoding a polypeptide providing the plant with resistance or tolerance to one or more additional herbicides, the polypeptide being selected from the group consisting of glyphosate tolerant 5-enol-pyruvylshikimate-3-phosphate synthase (EPSPS), glyphosate N-acetyl transferase (GAT), herbicide tolerant 4-hydroxypyruvyldioxgenase (HPPD), phosphinothricin acetyl transferase (PAT), cytochrome P450, glutathione S-transferase (GST), herbicide tolerant acetyl-COA-carboxylase (ACCase), herbicide tolerant acetolactate synthase (ALS), herbicide tolerant protoporphyrinogen oxidase (PPGO), bromoxynil nitrilase, herbicide tolerant phytoene desaturase, aryloxyalkanoate dioxygenase, and dicamba degrading enzymes; b. applying to the location a weed controlling amount of an herbicidal composition comprising one or more HPPD inhibitors, and c. further applying one or more additional fungicide, nematicide, insecticide, or herbicide.

15. The method of claim 14, wherein the one or more additional herbicide from step (c) is an herbicide selected from the group consisting of glyphosate, glufosinate, fomesafen, saflufenacil, lactofen, aciflurofen, cafentrazone-ethyl fluthiacet, oxyfluorfen, flumiclorac sulfentrazone, flumioxazin, metolachlor, S-metolachlor, acetochlor, alachlor, pyroxasulfone, flufenacet, dimethenamid, dimethenamid-P, bromoxynil, bentazon, metribuzin, atrazine, terbuthylazine, diuron, Linuron, ametryn, fluazifop, clethodim, fenoxaprop, haloxyfop, quizalofop, bensulfuron, nicosulfuron, rimsulfuron, primisulfuron, thifensulfuron, foramsulfuron, chlorsulfuron, halosulfuron, imazaquin, imazapic, imazapyr imazethapyr, imazamox, iodosulfuron, metsulfuron, mesosulfuron sulfosulfuron trifloxysulfuron tribenuron methyl, thiazopyr, tebuthiuron, diclosulam, cloransulam-methyl, flucarbazone, flumetsulam amicarbazone, thiencarbazone, chlorimuron-ethyl, dicamba, 2,4-D, 2,4-DB, fluroxypyr, diflufenzopyr, tirclopyr, picloram, quinclorac, clopyralid and aminopyralid; and agrochemically acceptable salts thereof.

16. A method of producing a soybean plant resistant to a glutamine synthetase inhibitor comprising introducing into the genome of the soybean plant event SYHT0H2, wherein a representative seed comprising said event has been deposited under ATCC Accession No. PTA-11226, comprising the steps of:
  a. crossing a first soybean plant comprising event SYHT0H2 with a second soybean plant;
  b. selecting at least a first progeny plant that comprises event SYHT0H2 and is resistant to a glutamine synthetase inhibitor;
  c. selfing the first progeny plant to produce second generation progeny plants; and
  d. selecting at least a first plant homozygous for event SYHT0H2.

17. A method of controlling weeds at a location comprising soybean plants and weeds, wherein the soybean plants comprise event SYHT0H2, wherein a representative seed comprising said event has been deposited under ATCC Accession No. PTA-11226, and wherein the method comprises applying to the location a weed controlling amount of an herbicidal composition comprising one or more glutamine synthetase inhibitors.

18. The method of claim 17, wherein the crop plant further comprises one or more additional regions encoding a polypeptide providing the plant with resistance or tolerance to one or more additional herbicides, insects, fungal, bacterial and/or viral infections.

19. The method of claim 18, wherein the one or more additional regions encode a polypeptide providing the plant with resistance or tolerance to one or more additional herbicides, the polypeptide being selected from the group consisting of: glyphosate tolerant 5-enol-pyruvylshikimate-3-phosphate synthase (EPSPS), glyphosate N-acetyl transferase (GAT), herbicide tolerant 4-hydroxypyruvyldioxgenase (HPPD), phosphinothricin actetyl transferase (PAT), cytochrome P450, glutathione S-transferase (GST), herbicide tolerant acetyl-COA-carboxylase (ACCase), herbicide tolerant acetolactate synthase (ALS), herbicide tolerant protoporphyrinogen oxidase (PPGO), bromoxynil nitrilase, herbicide tolerant phytoene desaturase, aryloxyalkanoate dioxygenase, and dicamba degrading enzymes.

* * * * *